US012698471B2

(12) United States Patent
Brown et al.

(10) Patent No.: US 12,698,471 B2
(45) Date of Patent: Aug. 4, 2026

(54) **LIVE ATTENUATED STRAIN OF *STREPTOCOCCUS PNEUMONIAE* AND PHARMACEUTICAL COMPOSITIONS COMPRISING A LIVE ATTENUATED STRAIN OF *S. PNEUMONIAE***

(71) Applicant: UCL BUSINESS LTD, London (GB)

(72) Inventors: Jeremy Brown, London (GB); Elisa Ramos-Sevillano, London (GB)

(73) Assignee: UCL BUSINESS LTD, London (GB)

( * ) Notice: Subject to any disclaimer, the term of this patent is extended or adjusted under 35 U.S.C. 154(b) by 452 days.

(21) Appl. No.: 18/036,470

(22) PCT Filed: Nov. 12, 2021

(86) PCT No.: PCT/EP2021/081568
§ 371 (c)(1),
(2) Date: May 11, 2023

(87) PCT Pub. No.: WO2022/101436
PCT Pub. Date: May 19, 2022

(65) Prior Publication Data
US 2023/0399604 A1      Dec. 14, 2023

(30) Foreign Application Priority Data
Nov. 12, 2020      (GB) ..................................... 2017877

(51) Int. Cl.
*C12N 1/36* (2006.01)
*A61K 39/00* (2006.01)
*A61P 31/04* (2006.01)

(52) U.S. Cl.
CPC ................. *C12N 1/36* (2013.01); *A61P 31/04* (2018.01); *A61K 2039/522* (2013.01)

(58) Field of Classification Search
None
See application file for complete search history.

(56) References Cited

FOREIGN PATENT DOCUMENTS

WO      02/34773  A2      5/2002
WO      2018220176  A1      12/2018

OTHER PUBLICATIONS

Ramos-Sevillano, et al., "Preclinical Development of Virulence-attenuated *Streptococcus pneumoniae* Strains Able to Enhance Protective Immunity against Pneumococcal Infection", Respir Med Am J Respir Crit Care Med, vol. 203, No. 8, 2020, pp. 1037-1041.
Roche, et al., "Live attenuated *Streptococcus pneumoniae* strains induce serotype-independent mucosal and systemic protection in mice", Infection and Immunity, vol. 75, No. 5, 2007, pp. 2469-2475.
Hill, et al., "A Randomized Controlled Clinical Trial of Nasal Immunization with Live Virulence Attenuated *Streptococcus pneumoniae* Strains Using Human Infection Challenge", Am. J. Respir. Crit. Care Med., 2023, 208 (8):868-878.
Ramos-Sevillano et al., "Preclinical Development of Virulence-attenuated *Streptococcus pneumoniae* Strains Able to Enhance Protective Immunity against Pneumococcal Infection", Am. J. Respir. Crit. Care Med. 203(8):1037-1041 (2021).
Ramos-Sevillano et al., "Essential role of proline synthesis and the one-carbon metabolism pathways for systemic virulence of *Streptococcus pneumoniae*", American Society for Microbiology, 2024, 15(11), 25 pgs.

*Primary Examiner* — Oluwatosin A Ogunbiyi
(74) *Attorney, Agent, or Firm* — ArentFox Schiff LLP; Daniel W. J. Clarke D.

(57) ABSTRACT

A live attenuated strain of *S. pneumoniae* containing at least two genes or operons that have disrupted expression or encode for proteins that have impaired function, the two genes or operons being fhs, piaA, proABC, spxB, Sp_1288 and Sp_1027. Pharmaceutical compositions containing the live attenuated strains are also described. The live attenuated strains and pharmaceutical compositions can be used to boost immunity in a subject and prevent *S. pneumoniae* infection.

24 Claims, 26 Drawing Sheets

Specification includes a Sequence Listing.

A

Pneumonia

B

Pneumonia

A

B

A

B

C

D

G

H

C

D

SEQUENCE LISTING

<160> NUMBER OF SEQ ID NOS: 93

<210> SEQ ID NO 1
<211> LENGTH: 1671
<212> TYPE: DNA
<213> ORGANISM: Streptococcus pneumoniae

<400> SEQUENCE: 1
atgaaaacag atattgaaat cgcacagagt attgagttga agccaattgt tgatgttgta      60
gagaaacttg gtatttctta cgacgatttg gagttgtacg gaaagtacaa ggctaaactc     120
agctttgata aaaattcgggc agttgagagc aatccagtcg gtaaattgat cttggttact     180
gccatcaacc caacacctgc aggtgaagga aagtcgacgc ttaccattgg tcttgcggat     240
gccttgaaca agattggcaa gaaaaccatg attgctatcc gcgaaccgtc tcttggtcca     300

```
gtcatgggga tcaagggtgg tgctgctggt ggtgggtatg cacaagttct gccaatggaa        360
gacatcaacc tccactttac tggagatatg catgctatta caactgccaa caatgccctt        420
tctgccttga ttgacaacca cttgcaccaa gggaatgagc tgggaattga tcaacgtcgt        480
atcctctgga aacgcgttgt ggacttgaac gaccgtgcgc tccgccatgt gactgttggt        540
cttggtggtc ctctaaacgg tattccacgt gaggacggtt ttgatattac agttgcttca        600
gaaatcatgg caattctttg cttggcaacg gacatcgagg acttgaaact tcgtttggcg        660
aatatcgtta ttggttatcg ctatgaccgt acgcctgttt ctgtaggtga tttgcaggtt        720
gagggtgcct tggctttgat tttgaaggat gctattaagc caaacttggt tcagacaatt        780
tacggtacac ctgcctttgt acacggtggt ccatttgcca atatcgctca tggctgtaac        840
tctgttttgg cgacgacaac agcccttcac ttggctgatt acactgttac tgaagctggt        900
tttggtgcgg accttggtgc tgagaaattc cttgatatca agacaccaaa cttgccaaca        960
tctccagatg cagttgttat tgtcgcaacc cttcgtgccc ttaagatgaa tggtggtgtg       1020
gctaaagacg ctctgactga agaaatgta gaggcagttc gtgcaggttt tgctaacttg       1080
aaacgccacg ttgaaaatat ccgtaagttc ggtattccag cagttgtagc tattaacgaa       1140
tttgtatctg atacagaagc tgaaattgca gccttaaaag aactctgtgc ctcaatcgat       1200
gtaccagttg aattggctag tgtctgggct gatggagcag aaggtggagt agcacttgcc       1260
gaaacagttg ttaagacaat tgctgaaaat ccagctaact ataaacgttt gtatgataat       1320
gacctttctg tccaagaaaa gattgaaaaa attgtcactg aaatctatcg tggtagcaaa       1380
gtgaactttg agaagaaagc tcaaacacaa attgctcaaa tcgttcaaaa cggttgggac       1440
aaattgccaa tctgtatggc taaaactcaa tacagtttct cagacaatcc aaatgcgctt       1500
ggagcaccag aaaactttga aattaccatt cgtgaattgg taccaaaatt aggtgcaggc       1560
ttcatcgttg ccttaactgg tgatgttatg accatgccag tcttccaaa acgtccagca       1620 gctctcaaca tggatgttga aagcgatgga actgtactag gcttgttcta g           1671
```

<210> SEQ ID NO 2
<211> LENGTH: 1026
<212> TYPE: DNA
<213> ORGANISM: Streptococcus pneumoniae

<400> SEQUENCE: 2

```
atgaaaaaca aatttttct aatagctatt ttagctatgt gtatagtttt tagcgcttgt         60
tcttctaatt ctgttaaaaa tgaagaaat acttctaaag agcatgcgcc tgataaaata        120
gttttagatc atgctttcgg tcaaactata ttagataaaa aacctgaaag agttgcaact        180
attgcttggg gaaatcatga tgtagcatta gctttaggaa tagttcctgt tggatttcta        240
aaagcaaatt acggtgtaag tgctgataaa ggagtttcac catggacaga agaaaaaatc        300
aaagaactaa atggtaaagc taacctattt gacgatttgg atggacttaa ctttgaagca        360
atatcaaatt ctaaaccaga tgttatctta gcaggttatt ctggtataac taaagaagat        420
tatgacactc tatcaaaaat tgctcctgta gcagcataca atctaaacc ttggcaaact        480 ttatggagag atatgattaa aattgattca aaagccttag gtatggaaaa agaaggtgat        540
gagttaatca aaaatactga agctcgtata tccaaagaat tagaaaaaca tccagaaatc        600
aaaggaaaaa tcaaaggaaa aaagtatta tttactatga ttaatgctgc agatacatca        660
aaattctgga tttatactag caaagatcca agagcaaatt atttaacaga tttaggtcta        720
```

```
gttttccctg aatcattaaa agaatttgag agtgaagata gttttgcaaa ggaaatttct          780
gcagaagaag caaataagat aaatgatgct gatgtaatca taacttatgg tgatgataaa          840
actcttgaag ctttacaaaa agatcctctt ttaggtaaaa taaatgcaat taaaaatggt          900
gccgttgctg taattccaga taatacaccg ttagcagcct catgcactcc aacaccactt          960
tcaataaact atactattga agaataccta aatctttag gaaatgcatg caaaaatgcg         1020
aaataa                                                                    1026
```

```
<210> SEQ ID NO 3
<211> LENGTH: 3171
<212> TYPE: DNA
<213> ORGANISM: Streptococcus pneumoniae

<400> SEQUENCE: 3
atgaaataca aacggattgt ctttaaggtg ggtacttctt ctctgacaaa tgaggatgga           60
agtttatcac gtagtaaggt aaaggatatt acccagcagt tggctatgct gcacgaggct          120
ggtcatgagt tgattttggt gtcttcaggt gccattgcgg ctggttttgg agccttagga          180
tttaaaaagc gtccgactaa gattgctgat aaacaggctt cagcagcggt agggcaaggg          240
cttttgttgg aagaatatac aaccaatctt ctcttgcgtc aaatcgtttc tgcacaaatc          300
ttgctgaccc aagatgattt tgtggataag cgtcgttata aaaatgccca tcaggctttg          360
tcggttttac tcaaccgtgg ggcaattcct atcatcaatg agaatgatag tgtcgttatt          420
gatgaggtca aggttgggga caatgacact ctaagtgccc aagtagcggc gatggtccaa          480
gcagaccttt tggttctctt gacagatgtg gacggtctct atactggaaa tcctaattca          540
gatccaagag ccaaacgctt ggagagaata gagaccatca atcgtgagat tattgatatg          600
gctggtggag ctggttcgtc aaacggaact gggggtatgt taaccaaaat caaggctgca          660
actatcgcga cggaatcagg agttcctgtt tatatctgct catccttgaa atcagattcc          720
atgattgagc ggcagagga gaccgaggat ggttcttact ttgttgctca agagaagggg          780
cttcgtaccc agaaacaatg gcttgccttc tatgctcaga gtcaaggttc tatttgggtt          840
gataaagggc tgcggaagc tctctctcaa catggaaaga gtcttctctt atctggtatt          900
gttgaagcag aaggagcctt ttcttacggt gatatcgtga cagtatttga caaggaaagt          960
ggaaaatcac ttggaaaagg acgcgtgcaa tttggagcat ctgctttgga ggatatattg         1020
cgttctcaaa aagccaaggg tgtcttgatt taccgtgacg actggatttc cattactcct         1080
gaaatccaac tacttttttac agaattttag atggtgagta gacaagaaca atttgaacag         1140
gtacaggctg ttaaaaaatc gattaacaca gctagtgaag aagtgaaaaa tcaagccttg         1200
ctagccatgg ctgatcactt agtggctgct actgaggaaa ttttagcggc taatgccctc         1260
gatatggcag cggctaaggg gaaaatctca gatgtgatgt tggatcgtct ttatttggat         1320
gcagatcgta tagaagcgat ggcaagagga attcgtgaag tggttgcctt accagatcca         1380
atcggtgaag ttttagaaac aagtcagctt gaaaatggtt tggttatcac aaaaaaacgt         1440
gtagctatgg tgtcatcgg tattatctat gaaagccgtc caaatgtgac gtctgatgcg         1500
gctgctttga ctcttaagag tggaaatgcg gttgttcttc gtagtggtaa ggatgcctat         1560
caaacaaccc atgccattgt cacagccttg aagaagggct tggagacgac tactattcac         1620
ccaaatgtga ttcaactggt ggaagatact agccatgaaa gtagttatgc tatgatgaag         1680
gccaagggct atctagacct cctcattcct cgtggaggag ctggcttgat caatgcagtg         1740
gttgagaatg cgattgtacc tgttatcgag acagggactg ggattgtcca tgtctatgtg         1800
```

-continued

```
gataaggatg cagacgaaga caaggcgctg tctatcatca acaatgctaa aaccagtcgt   1860
ccttctgttt gtaatgccat ggaggttctg ctggttcatg aagataaggc agcaagcatc   1920
cttcctcgct tggatcaaat gctggttgca gagcgtaagg aagctggact ggaaccaatt   1980
caattccgct tggatagcaa agcaagccag tttgtttcag gtcaagcagc tgagacccaa   2040
gactttgaca ccgagttttt agactatgtc cttgctgtta aggttgtgag cagtttagaa   2100
gaagcggttg cgcacattga atcccacagc acccatcatt cggatgctat tgtgacggaa   2160
aatgctgaag ctgcagcata ctttacagat caagtggact ctgcagcggt gtatgttaat   2220
gcctcaactc gtttcacaga tggaggacaa tttggtcttg gttgtgaaat ggggatttct   2280
actcagaaat tgcacgcgcg tggtccaatg ggcttgaagg aattgactag ctacaagtat   2340
gtggtcactg gtgatggaca gataagggag taaatgaaga ttggatttat cggtttgggg   2400
aatatgggtg ctagtttagc caagtctgtc ttgcaggcta gaccgtcaga tgagattctc   2460
cttgccaatc gtagtcaagt caaggtggat gctttcatcg ctaacttcgg tggtcagact   2520
tctaacaatg aagaaatatt cgaagaagca gatgtgattt ttctaggtgt taagcctgct   2580
cagttttctg aactgctttc tcaataccag accatccttg aaaaaagaga aagtcttctt   2640
ttgatttcga tggcagctgg attgatctta gaaaaactag caagtcttat cccaagccaa   2700
caccgaatta ttcgtatgat gcctaatacc cctgcttcta tcgggcaagg agtgattagt   2760
tatgccttgt ctcctaattg cagggctgag gacagtgagc tcttttgtca gctttttatcc   2820 aaggctggtc tcttggttga attaggagaa agcttaatca atgcagcgac aggtcttgca   2880
ggctgtggac cagcctttgt ctatctcttt attgaggcct tggcagatgc aggtgttcag   2940
acgggattac cacgagaaac agccttgaaa atggcagccc aaactgtggt aggagctggg   3000
caattggtcc tagaaagcca gcaacatcct ggagttttga aagatcaagt ttgtagtcca   3060
ggcggttcga ctattgctgg cgtagcaagc ctagaagcgc atgcttttcg aggaacggtc   3120
atggaggcag ttcatcaagc ctataaacga acacaagaac taggtaaata a           3171
```

```
<210> SEQ ID NO 4
<211> LENGTH: 1110
<212> TYPE: DNA
<213> ORGANISM: Streptococcus pneumoniae

<400> SEQUENCE: 4
```

```
atgaaataca aacggattgt ctttaaggtg ggtacttctt ctctgacaaa tgaggatgga     60
agtttatcac gtagtaaggt aaaggatatt acccagcagt tggctatgct gcacgaggct    120
ggtcatgagt tgattttggt gtcttcaggt gccattgcgg ctggttttgg agccttagga    180
tttaaaaagc gtccgactaa gattgctgat aaacaggctt cagcagcggt agggcaaggg    240 ctttttgttgg aagaatatac aaccaatctt ctcttgcgtc aaatcgtttc tgcacaaatc    300
ttgctgaccc aagatgattt tgtggataag cgtcgttata aaaatgccca tcaggctttg    360
tcggttttac tcaaccgtgg ggcaattcct atcatcaatg agaatgatag tgtcgttatt    420
gatgaggtca aggttgggga caatgacact ctaagtgccc aagtagcggc gatggtccaa    480
gcagaccttt tggttctctt gacagatgtg gacggtctct atactggaaa tcctaattca    540
gatccaagag ccaaacgctt ggagagaata gagaccatca atcgtgagat tattgatatg    600
gctggtggag ctggttcgtc aaacggaact gggggtatgt taaccaaaat caaggctgca    660
actatcgcga cggaatcagg agttcctgtt tatatctgct catccttgaa atcagattcc    720
```

-continued

```
atgattgagg cggcagagga gaccgaggat ggttcttact ttgttgctca agagaagggg    780
cttcgtaccc agaaacaatg gcttgccttc tatgctcaga gtcaaggttc tatttgggtt    840
gataaagggg ctgcggaagc tctctctcaa catggaaaga gtcttctctt atctggtatt    900
gttgaagcag aaggagcctt ttcttacggt gatatcgtga cagtatttga caaggaaagt    960
ggaaaatcac ttggaaaagg acgcgtgcaa tttggagcat ctgctttgga ggatatattg   1020
cgttctcaaa aagccaaggg tgtcttgatt taccgtgacg actggatttc cattactcct   1080
gaaatccaac tacttttac agaattttag                                     1110
```

```
<210> SEQ ID NO 5
<211> LENGTH: 1263
<212> TYPE: DNA
<213> ORGANISM: Streptococcus pneumoniae

<400> SEQUENCE: 5
atggtgagta gacaagaaca atttgaacag gtacaggctg ttaaaaaatc gattaacaca     60
gctagtgaag aagtgaaaaa tcaagccttg ctagccatgg ctgatcactt agtggctgct    120
actgaggaaa ttttagcggc taatgccctc gatatggcag cggctaaggg gaaaatctca    180
gatgtgatgt tggatcgtct ttatttggat gcagatcgta tagaagcgat ggcaagagga    240
attcgtgaag tggttgcctt accagatcca atcggtgaag ttttagaaac aagtcagctt    300
gaaaatggtt tggttatcac aaaaaaacgt gtagctatgg tgtcatcgg tattatctat    360 gaaagccgtc caaatgtgac gtctgatgcg gctgctttga ctcttaagag tggaaatgcg    420
gttgttcttc gtagtggtaa ggatgcctat caaacaaccc atgccattgt cacagccttg    480
aagaagggct tggagacgac tactattcac ccaaatgtga ttcaactggt ggaagatact    540
agccatgaaa gtagttatgc tatgatgaag gccaagggct atctagacct cctcattcct    600
cgtggaggag ctggcttgat caatgcagtg gttgagaatg cgattgtacc tgttatcgag    660
acagggactg ggattgtcca tgtctatgtg gataaggatg cagacgaaga caaggcgctg    720
tctatcatca caatgctaa aaccagtcgt ccttctgttt gtaatgccat ggaggttctg    780
ctggttcatg aagataaggc agcaagcatc cttcctcgct tggatcaaat gctggttgca    840
gagcgtaagg aagctggact ggaaccaatt caattccgct tggatagcaa agcaagccag    900
tttgtttcag gtcaagcagc tgagacccaa gactttgaca ccgagttttt agactatgtc    960
cttgctgtta aggttgtgag cagtttagaa gaagcggttg cgcacattga atcccacagc   1020
acccatcatt cggatgctat tgtgacggaa aatgctgaag ctgcagcata ctttacagat   1080
caagtggact ctgcagcggt gtatgttaat gcctcaactc gtttcacaga tggaggacaa   1140
tttggtcttg gttgtgaaat ggggatttct actcagaaat tgcacgcgcg tggtccaatg   1200
ggcttgaagg aattgactag ctacaagtat gtggtcactg tgatggaca gataagggag   1260 taa                                                                 1263
```

```
<210> SEQ ID NO 6
<211> LENGTH: 798
<212> TYPE: DNA
<213> ORGANISM: Streptococcus pneumoniae

<400> SEQUENCE: 6
atgaagattg gatttatcgg tttggggaat atgggtgcta gtttagccaa gtctgtcttg     60
caggctagac cgtcagatga gattctcctt gccaatcgta gtcaagtcaa ggtggatgct    120
ttcatcgcta acttcggtgg tcagacttct aacaatgaag aaatattcga agaagcagat    180
```

-continued

```
gtgattttc taggtgttaa gcctgctcag ttttctgaac tgcttctca ataccagacc      240 atccttgaaa aaagagaaag tcttcttttg atttcgatgg cagctggatt gatcttagaa      300
aaactagcaa gtcttatccc aagccaacac cgaattattc gtatgatgcc taatacccct      360
gcttctatcg ggcaaggagt gattagttat gccttgtctc ctaattgcag ggctgaggac      420
agtgagctct tttgtcagct tttatccaag gctggtctct tggttgaatt aggagaaagc      480
ttaatcaatg cagcgacagg tcttgcaggc tgtggaccag cctttgtcta tctctttatt      540
gaggccttgg cagatgcagg tgttcagacg ggattaccac gagaaacagc cttgaaaatg      600
gcagcccaaa ctgtggtagg agctgggcaa ttggtcctag aaagccagca acatcctgga      660
gttttgaaag atcaagtttg tagtccaggc ggttcgacta ttgctggcgt agcaagccta      720
gaagcgcatg cttttcgagg aacggtcatg gaggcagttc atcaagccta taaacgaaca      780
caagaactag gtaaataa                                                   798
```

<210> SEQ ID NO 7
<211> LENGTH: 1776
<212> TYPE: DNA
<213> ORGANISM: Streptococcus pneumoniae

<400> SEQUENCE: 7

```
atgactcaag ggaaaattac tgcatctgca gcaatgctta acgtattgaa aacatggggc       60
gtagatacaa tctacggtat cccatcagga acactcagct cattgatgga cgctttggct      120
gaagacaaag atatccgctt cttacaagtt cgccacgaag agacaggtgc tcttgcagcg      180
gttatgcaag ctaaattcgg cggctcaatc ggggttgcag ttggttcagg tggtccaggt      240
gcgactcact tgattaacgg tgtttacgat gcagctatgg ataacactcc attcctagcg      300
atccttggat cacgtccagt taacgaattg aacatggatg ctttccaaga gcttaaccaa      360
aacccaatgt acaacggtat cgctgtttac aacaaacgtg tagcttacgc tgagcaattg      420
ccaaaagtaa ttgacgaagc ctgccgtgct gcaatttcta aaaaaggtcc agctgttgtt      480
gaaattccag taaacttcgg tttccaagaa atcgatgaaa actcatacta cggttcaggt      540
tcatacgaac gctcattcat cgctcctgct ttgaacgaag ttgaaatcga caaagctgtt      600
gaaatcttga caatgctga acgcccagtt atctatgctg atttggtgg tgttaaagct      660 ggtgaagtga ttactgaatt gtcacgtaaa atcaaagcac caatcatcac aactggtaaa      720
aactttgaag cttttcgaatg gaactatgaa ggtttgacag ttctgctta ccgtgttggt      780 tggaaaccag ccaacgaagt ggtctttgaa gcagacacag ttctttttcct tggttcaaac      840 ttcccatttg ctgaagttta cgaagcattc aagaacactg aaaaattcat ccaagtcgat      900 atcgacctt acaaacttgg taaacgtcat gcccttgacg cttcaatcct tggtgatgct      960
ggtcaagcag ctaaagctat ccttgacaaa gtaaacccag ttgaatcaac tccatggtgg     1020
cgtgcaaacg ttaagaacaa ccaaaactgg cgtgattaca tgaacaaact cgaaggtaaa     1080
actgagggtg aattgcaatt gtatcaagtt tacaatgcaa tcaacaaaca tgctgatcaa     1140
gacgctatct actcaatcga cgtaggtaac actactcaaa catctactcg tcaccttcac     1200
atgacaccta gaacatgtg gcgtacatct ccactctttg cgacaatggg tattgccctt     1260
cctggtggta tcgctgctaa gaaagacaat ccagatcgcc aagtatggaa catcatgggt     1320
gacggagcat tcaacatgtg ctacccagac gttatcacaa cgttcaata cgaccttcca     1380 gttatcaacc ttgtcttctc aaatgctgag tacggcttca tcaagaacaa atacgaagat     1440
```

-continued

```
acaaacaaac acttgtttgg tgtagacttc acaaacgctg actacgctaa aattgcggaa    1500
gctcaaggag ctgttggatt cacagttgac cgtatcgaag acatcgatgc agttgttgca    1560
gaagctgtta aattgaacaa agaaggtaaa actgttgtca tcgatgctcg catcactcaa    1620
caccgtccac ttccagtaga agtacttgaa ttggatccaa aacttcactc agaagaagct    1680
atcaaagcct tcaaggaaaa atacgaagca gaagaactcg taccattccg tctcttcttg    1740
gaagaagaag gattgcaatc acgcgcaatt aaataa                              1776

<210> SEQ ID NO 8
<211> LENGTH: 333
<212> TYPE: DNA
<213> ORGANISM: Streptococcus pneumoniae

<400> SEQUENCE: 8
atggaaatcg aaaaaaccaa tcgtatgaat gcgctctttg aattttatgc ggcgcttttg      60
acagataagc aaatgaatta tatcgagctc tactacgctg atgattacag ccttgctgaa     120
attgccgagg agttcggtgt cagtcgtcag gctgtctatg acaatatcaa gcgaacagaa     180
aagattctgg aagattatga gatgaaattg cacatgtact cggactatat tgtccgcagt     240
cagatttttg atcagatttt ggagcgctat cccaaggata actttctgca ggagcagata     300
gaaattttaa caagcattga taatagagaa taa                                 333

<210> SEQ ID NO 9
<211> LENGTH: 975
<212> TYPE: DNA
<213> ORGANISM: Streptococcus pneumoniae

<400> SEQUENCE: 9
atgagaaaga aactctttct gactagtgct gcggtcttgt gggcagtaac agctatgaat      60
agcgtccatg cagcaacaga tgttcaaaaa gttatcgatg aaacctatgt ccaacctgaa     120
tatgtcctag gttcctccct atctgaagac caaaaaaatc aaactcttaa aaaactgggc     180
tacaatgcct caacagatac caaagaattc aagaccatga cacctgatgt ttattctaaa     240
atcatgaatg tggccaatga ctctagctta cagttgtatt catcagccaa gattcaaaag     300
ctaggtgaca aatcgccact tgaggtcaag attgaaacac cagaaaatat cactaaggtg     360
actcaggata tgtaccgaaa cgcagcagta acgctgggta tggaacatgc caaaatcact     420
gtagcagccc ctattccagt tacaggtgag agtgctttgg ctgggatcta ctattcgcta     480
gaagctaatg gagccaaggt gccgcaagcc aataaagatt tggctcaaga gagctaaag     540 gctttgtcag atatcaatgc tgaaaataag gacaaatcag gctatgatgc taataaatta     600
aacgttgccc tagctgatat caagtcagga ctcgccaaag ctaaagaaag caagggaaat     660
ctgacagaag aagatgtacg caagattgtt gaagatacct taaaaaatta caaacttgat     720
caggtcataa caggaaacca gatcaatatc atcatcaatt ttgccttgaa tctctcaaag     780
agtgatatcc tcagcaatgc agatttcact aaaaccttaa atgaccttaa acaaagcatc     840
gtatcacaag ctggcgacag tttttaaaaat atcaacctta actttgattc ggataaggcg     900
ctagaggacg gtggtaactt cttaagctcc ctctggcaag cccttgtcaa cttcttcaag     960
agttttggtt cttaa                                                     975

<210> SEQ ID NO 10
<211> LENGTH: 20
<212> TYPE: DNA
<213> ORGANISM: Artificial Sequence
```

-continued

```
<220> FEATURE:
<223> OTHER INFORMATION: pspA-UpF

<400> SEQUENCE: 10
ctaatcaacc actttgggca                                                  20

<210> SEQ ID NO 11
<211> LENGTH: 39
<212> TYPE: DNA
<213> ORGANISM: Artificial Sequence
<220> FEATURE:
<223> OTHER INFORMATION: pspA_Upsec_F

<400> SEQUENCE: 11
cagaaaagag gtaaatttag gatcccccgt ttgattttt                             39

<210> SEQ ID NO 12
<211> LENGTH: 41
<212> TYPE: DNA
<213> ORGANISM: Artificial Sequence
<220> FEATURE:
<223> OTHER INFORMATION: pspA_UpspecR

<400> SEQUENCE: 12
aaatcaaacg ggggatccta aatttacctc ttttctgata g                          41

<210> SEQ ID NO 13
<211> LENGTH: 38
<212> TYPE: DNA
<213> ORGANISM: Artificial Sequence
<220> FEATURE:
<223> OTHER INFORMATION: pspA_Downspec_F

<400> SEQUENCE: 13
ggatccattc cgcgtcgccg attaaattaa agcatgtt                              38

<210> SEQ ID NO 14
<211> LENGTH: 42
<212> TYPE: DNA
<213> ORGANISM: Artificial Sequence
<220> FEATURE:
<223> OTHER INFORMATION: pspa_Downspec_R

<400> SEQUENCE: 14
aacatgcttt aatttaatcg gcgacgcgga atggatccaa tt                         42

<210> SEQ ID NO 15
<211> LENGTH: 22
<212> TYPE: DNA
<213> ORGANISM: Artificial Sequence
<220> FEATURE:
<223> OTHER INFORMATION: pspA_DownR

<400> SEQUENCE: 15
catggacggt caccttagag tc                                               22

<210> SEQ ID NO 16
<211> LENGTH: 28
<212> TYPE: DNA
<213> ORGANISM: Artificial Sequence
<220> FEATURE:
<223> OTHER INFORMATION: piaA_UpF

<400> SEQUENCE: 16
gttatggcac aaatgggaaa ggataaac                                         28
```

-continued

```
<210> SEQ ID NO 17
<211> LENGTH: 38
<212> TYPE: DNA
<213> ORGANISM: Artificial Sequence
<220> FEATURE:
<223> OTHER INFORMATION: piaA_UpKanF

<400> SEQUENCE: 17
atgtttaagg agttttttgtc gatactatgt tatacgcc                                   38

<210> SEQ ID NO 18
<211> LENGTH: 38
<212> TYPE: DNA
<213> ORGANISM: Artificial Sequence
<220> FEATURE:
<223> OTHER INFORMATION: PiaA_UpKanR

<400> SEQUENCE: 18
ggcgtataac atagtatcga caaaaactcc ttaaacat                                     38

<210> SEQ ID NO 19
<211> LENGTH: 37
<212> TYPE: DNA
<213> ORGANISM: Artificial Sequence
<220> FEATURE:
<223> OTHER INFORMATION: PiaA_DownKanF

<400> SEQUENCE: 19
tgaagtacat ccgcaacagg aaatgcatgc aaaaatg                                      37

<210> SEQ ID NO 20
<211> LENGTH: 37
<212> TYPE: DNA
<213> ORGANISM: Artificial Sequence
<220> FEATURE:
<223> OTHER INFORMATION: PiaA_DownKanR

<400> SEQUENCE: 20
catttttgca tgcatttcct gttgcggatg tacttca                                      37

<210> SEQ ID NO 21
<211> LENGTH: 24
<212> TYPE: DNA
<213> ORGANISM: Artificial Sequence
<220> FEATURE:
<223> OTHER INFORMATION: PiaA_DownR

<400> SEQUENCE: 21
ctataagacc tacgaagcca atag                                                    24

<210> SEQ ID NO 22
<211> LENGTH: 27
<212> TYPE: DNA
<213> ORGANISM: Artificial Sequence
<220> FEATURE:
<223> OTHER INFORMATION: AdcA_UpF

<400> SEQUENCE: 22
gcatagtatc aagttttttgc acacctg                                               27

<210> SEQ ID NO 23
<211> LENGTH: 43
<212> TYPE: DNA
<213> ORGANISM: Artificial Sequence
<220> FEATURE:
<223> OTHER INFORMATION: AdcA_UpspecF
```

-continued

```
<400> SEQUENCE: 23
tcttatgaac tagtcgattt ctcagatccc ccgtttgatt ttt                     43

<210> SEQ ID NO 24
<211> LENGTH: 49
<212> TYPE: DNA
<213> ORGANISM: Artificial Sequence
<220> FEATURE:
<223> OTHER INFORMATION: AdcA_UpspecR

<400> SEQUENCE: 24
aaaaatcaaa cgggggatct gagaaatcga ctagttcata agagctagt              49

<210> SEQ ID NO 25
<211> LENGTH: 44
<212> TYPE: DNA
<213> ORGANISM: Artificial Sequence
<220> FEATURE:
<223> OTHER INFORMATION: AdcA_DownspecF

<400> SEQUENCE: 25
ggatccattc cgcgtctcct atttgataaa acgtcttact aaac                   44

<210> SEQ ID NO 26
<211> LENGTH: 40
<212> TYPE: DNA
<213> ORGANISM: Artificial Sequence
<220> FEATURE:
<223> OTHER INFORMATION: AdcA_DownspecR

<400> SEQUENCE: 26
agtaagacgt tttatcaaat aggagacgcg gaatggatcc                        40

<210> SEQ ID NO 27
<211> LENGTH: 24
<212> TYPE: DNA
<213> ORGANISM: Artificial Sequence
<220> FEATURE:
<223> OTHER INFORMATION: AdcA_DownR

<400> SEQUENCE: 27
gagcaagggt aaaagctcga gttc                                         24

<210> SEQ ID NO 28
<211> LENGTH: 19
<212> TYPE: DNA
<213> ORGANISM: Artificial Sequence
<220> FEATURE:
<223> OTHER INFORMATION: PsaA_UpF

<400> SEQUENCE: 28
ggaggtgacc tatgattgc                                               19

<210> SEQ ID NO 29
<211> LENGTH: 42
<212> TYPE: DNA
<213> ORGANISM: Artificial Sequence
<220> FEATURE:
<223> OTHER INFORMATION: PsaA_UpspecF

<400> SEQUENCE: 29
gccctaataa attggaggat ctagatcccc cgtttgattt tt                     42

<210> SEQ ID NO 30
```

-continued

```
<211> LENGTH: 42
<212> TYPE: DNA
<213> ORGANISM: Artificial Sequence
<220> FEATURE:
<223> OTHER INFORMATION: PsaA_UpspecR

<400> SEQUENCE: 30
aaaatcaaac gggggatcta gatcctccaa tttattaggg ct                        42

<210> SEQ ID NO 31
<211> LENGTH: 43
<212> TYPE: DNA
<213> ORGANISM: Artificial Sequence
<220> FEATURE:
<223> OTHER INFORMATION: PsaA_DownspecF

<400> SEQUENCE: 31
aaattggatc cattccgcgt cgcctctgaa aaacgtcatt ctc                       43

<210> SEQ ID NO 32
<211> LENGTH: 35
<212> TYPE: DNA
<213> ORGANISM: Artificial Sequence
<220> FEATURE:
<223> OTHER INFORMATION: PsaA_DownspecR

<400> SEQUENCE: 32
atgacgtttt tcagaggcga cgcggaatgg atcca                               35

<210> SEQ ID NO 33
<211> LENGTH: 27
<212> TYPE: DNA
<213> ORGANISM: Artificial Sequence
<220> FEATURE:
<223> OTHER INFORMATION: PsaA_DownR

<400> SEQUENCE: 33
atattatcca cgtattcaac gtagcga                                        27

<210> SEQ ID NO 34
<211> LENGTH: 22
<212> TYPE: DNA
<213> ORGANISM: Artificial Sequence
<220> FEATURE:
<223> OTHER INFORMATION: Spr832_UpF

<400> SEQUENCE: 34
ccaaacgggt atcttgttac ag                                             22

<210> SEQ ID NO 35
<211> LENGTH: 38
<212> TYPE: DNA
<213> ORGANISM: Artificial Sequence
<220> FEATURE:
<223> OTHER INFORMATION: Spr832_UpspecF

<400> SEQUENCE: 35
tgttattcat gttataatgg agatcccccg tttgattt                            38

<210> SEQ ID NO 36
<211> LENGTH: 43
<212> TYPE: DNA
<213> ORGANISM: Artificial Sequence
<220> FEATURE:
<223> OTHER INFORMATION: Spr832_UpspecR

<400> SEQUENCE: 36
```

-continued atccattaaa aatcaaacgg gggatctcca ttataacatg aat                     43

<210> SEQ ID NO 37
<211> LENGTH: 42
<212> TYPE: DNA
<213> ORGANISM: Artificial Sequence
<220> FEATURE:
<223> OTHER INFORMATION: Spr832_DownspecF

<400> SEQUENCE: 37
aaaaattgga tccattccgc gtcagctttg actgcctctt tt                      42

<210> SEQ ID NO 38
<211> LENGTH: 37
<212> TYPE: DNA
<213> ORGANISM: Artificial Sequence
<220> FEATURE:
<223> OTHER INFORMATION: Spr832_DownspecR

<400> SEQUENCE: 38
aaagaggcag tcaaagctga cgcggaatgg atccaat                            37

<210> SEQ ID NO 39
<211> LENGTH: 25
<212> TYPE: DNA
<213> ORGANISM: Artificial Sequence
<220> FEATURE:
<223> OTHER INFORMATION: Spr832_DownR

<400> SEQUENCE: 39
ggaaactacc aatgctgtct tgttt                                         25

<210> SEQ ID NO 40
<211> LENGTH: 23
<212> TYPE: DNA
<213> ORGANISM: Artificial Sequence
<220> FEATURE:
<223> OTHER INFORMATION: Spr1197_UpF

<400> SEQUENCE: 40
tggaaggttt caatgtccgt aat                                           23

<210> SEQ ID NO 41
<211> LENGTH: 43
<212> TYPE: DNA
<213> ORGANISM: Artificial Sequence
<220> FEATURE:
<223> OTHER INFORMATION: Spr1197_UpSpecF

<400> SEQUENCE: 41
aactttcaaa tgccattttt cttgatcccc cgtttgattt tta                     43

<210> SEQ ID NO 42
<211> LENGTH: 43
<212> TYPE: DNA
<213> ORGANISM: Artificial Sequence
<220> FEATURE:
<223> OTHER INFORMATION: Spr1197_UpSpecR

<400> SEQUENCE: 42
taaaaatcaa acgggggatc aagaaaaatg gcatttgaaa gtt                     43

<210> SEQ ID NO 43
<211> LENGTH: 41
<212> TYPE: DNA

<213> ORGANISM: Artificial Sequence
<220> FEATURE:
<223> OTHER INFORMATION: Spr1197_DownSpecF

<400> SEQUENCE: 43
aattggatcc attccgcgtc ttattatacc aaaaattagc c                    41

<210> SEQ ID NO 44
<211> LENGTH: 46
<212> TYPE: DNA
<213> ORGANISM: Artificial Sequence
<220> FEATURE:
<223> OTHER INFORMATION: Spr1197_DownSpecR

<400> SEQUENCE: 44
ggtagattag ctaattttt ggtataataa gacgcggaat ggatcc              46

<210> SEQ ID NO 45
<211> LENGTH: 23
<212> TYPE: DNA
<213> ORGANISM: Artificial Sequence
<220> FEATURE:
<223> OTHER INFORMATION: Spr1197_DownR

<400> SEQUENCE: 45
cggatgcgaa atacaattca gtt                                        23

<210> SEQ ID NO 46
<211> LENGTH: 21
<212> TYPE: DNA
<213> ORGANISM: Artificial Sequence
<220> FEATURE:
<223> OTHER INFORMATION: SpxB - UpF

<400> SEQUENCE: 46
gtagaagtgt ttggattggc a                                          21

<210> SEQ ID NO 47
<211> LENGTH: 40
<212> TYPE: DNA
<213> ORGANISM: Artificial Sequence
<220> FEATURE:
<223> OTHER INFORMATION: SpxB - UpspecF

<400> SEQUENCE: 47
aaaaaattga aggagagtta tgatcccccg tttgattttt                      40

<210> SEQ ID NO 48
<211> LENGTH: 40
<212> TYPE: DNA
<213> ORGANISM: Artificial Sequence
<220> FEATURE:
<223> OTHER INFORMATION: SpxB - UpspecR

<400> SEQUENCE: 48
aaaaatcaaa cggggggatca taactctcct tcaatttttt                     40

<210> SEQ ID NO 49
<211> LENGTH: 34
<212> TYPE: DNA
<213> ORGANISM: Artificial Sequence
<220> FEATURE:
<223> OTHER INFORMATION: SpxB - DownspecF

<400> SEQUENCE: 49
ggatccattc cgcgtctctc gccgaaaatc aaat                            34

-continued

```
<210> SEQ ID NO 50
<211> LENGTH: 31
<212> TYPE: DNA
<213> ORGANISM: Artificial Sequence
<220> FEATURE:
<223> OTHER INFORMATION: SpxB - DownspecR

<400> SEQUENCE: 50
gattttcggc gagagacgcg gaatggatcc a                              31

<210> SEQ ID NO 51
<211> LENGTH: 25
<212> TYPE: DNA
<213> ORGANISM: Artificial Sequence
<220> FEATURE:
<223> OTHER INFORMATION: SpxB - DownR

<400> SEQUENCE: 51
aaacaagaca gcattggtag tttcc                                    25

<210> SEQ ID NO 52
<211> LENGTH: 20
<212> TYPE: DNA
<213> ORGANISM: Artificial Sequence
<220> FEATURE:
<223> OTHER INFORMATION: Fhs_UpF

<400> SEQUENCE: 52
ggcaagtggg taattcttga                                          20

<210> SEQ ID NO 53
<211> LENGTH: 41
<212> TYPE: DNA
<213> ORGANISM: Artificial Sequence
<220> FEATURE:
<223> OTHER INFORMATION: Fhs_UpspecF

<400> SEQUENCE: 53
ctttcaaatc taacatatct ctgatccccc gtttgatttt t                  41

<210> SEQ ID NO 54
<211> LENGTH: 41
<212> TYPE: DNA
<213> ORGANISM: Artificial Sequence
<220> FEATURE:
<223> OTHER INFORMATION: Fhs_UpspecR

<400> SEQUENCE: 54
aaaaatcaaa cgggggatca gagatatgtt agatttgaaa g                  41

<210> SEQ ID NO 55
<211> LENGTH: 41
<212> TYPE: DNA
<213> ORGANISM: Artificial Sequence
<220> FEATURE:
<223> OTHER INFORMATION: Fhs_DownspecF

<400> SEQUENCE: 55
ttggatccat tccgcgtccg cttatttttg tgtacaatag t                  41

<210> SEQ ID NO 56
<211> LENGTH: 41
<212> TYPE: DNA
<213> ORGANISM: Artificial Sequence
<220> FEATURE:
```

-continued

```
<223> OTHER INFORMATION: Fhs_DownspecR

<400> SEQUENCE: 56
actattgtac acaaaaataa gcggacgcgg aatggatcca a                         41

<210> SEQ ID NO 57
<211> LENGTH: 21
<212> TYPE: DNA
<213> ORGANISM: Artificial Sequence
<220> FEATURE:
<223> OTHER INFORMATION: Fhs_DownR

<400> SEQUENCE: 57
caaggaggag ttctgcaatt t                                               21

<210> SEQ ID NO 58
<211> LENGTH: 23
<212> TYPE: DNA
<213> ORGANISM: Artificial Sequence
<220> FEATURE:
<223> OTHER INFORMATION: Cps_UpF

<400> SEQUENCE: 58
ggattgataa aggtattggt ggt                                             23

<210> SEQ ID NO 59
<211> LENGTH: 53
<212> TYPE: DNA
<213> ORGANISM: Artificial Sequence
<220> FEATURE:
<223> OTHER INFORMATION: Cps_UpKanF

<400> SEQUENCE: 59
gctttctgtg tggaattact ataaatattg tcgatactat gttatacgcc aac           53

<210> SEQ ID NO 60
<211> LENGTH: 49
<212> TYPE: DNA
<213> ORGANISM: Artificial Sequence
<220> FEATURE:
<223> OTHER INFORMATION: Cps_UpKanR

<400> SEQUENCE: 60
gttggcgtat aacatagtat cgacaatatt tatagtaatt ccacacaga               49

<210> SEQ ID NO 61
<211> LENGTH: 46
<212> TYPE: DNA
<213> ORGANISM: Artificial Sequence
<220> FEATURE:
<223> OTHER INFORMATION: Cps_DownKanF

<400> SEQUENCE: 61
cttttctgaa gtacatccgc aacgaaaatg atgaaaagtt caaaac                   46

<210> SEQ ID NO 62
<211> LENGTH: 46
<212> TYPE: DNA
<213> ORGANISM: Artificial Sequence
<220> FEATURE:
<223> OTHER INFORMATION: Cps_DownKanR

<400> SEQUENCE: 62
gttttgaact tttcatcatt ttcgttgcgg atgtacttca gaaaag                   46
```

-continued

```
<210> SEQ ID NO 63
<211> LENGTH: 21
<212> TYPE: DNA
<213> ORGANISM: Artificial Sequence
<220> FEATURE:
<223> OTHER INFORMATION: Cps_DownR

<400> SEQUENCE: 63
cagtttgtcc attcaactga g                                          21

<210> SEQ ID NO 64
<211> LENGTH: 30
<212> TYPE: DNA
<213> ORGANISM: Artificial Sequence
<220> FEATURE:
<223> OTHER INFORMATION: MalX_UpF

<400> SEQUENCE: 64
gaaacgtttc accgcttttt ctaaaagagg                                 30

<210> SEQ ID NO 65
<211> LENGTH: 40
<212> TYPE: DNA
<213> ORGANISM: Artificial Sequence
<220> FEATURE:
<223> OTHER INFORMATION: MalX_UpspecF

<400> SEQUENCE: 65
tgctattctt tgggaggaag atcccccgtt tgatttttaa                       40

<210> SEQ ID NO 66
<211> LENGTH: 53
<212> TYPE: DNA
<213> ORGANISM: Artificial Sequence
<220> FEATURE:
<223> OTHER INFORMATION: MalX_UpspecR

<400> SEQUENCE: 66
ccattaaaaa tcaaacgggg gatcttcctc ccaaagaata gcaagtttta ttg        53

<210> SEQ ID NO 67
<211> LENGTH: 38
<212> TYPE: DNA
<213> ORGANISM: Artificial Sequence
<220> FEATURE:
<223> OTHER INFORMATION: MalX_DownspecF

<400> SEQUENCE: 67
aattggatcc attccgcgtc ttgttcaagg ggggtgga                        38

<210> SEQ ID NO 68
<211> LENGTH: 47
<212> TYPE: DNA
<213> ORGANISM: Artificial Sequence
<220> FEATURE:
<223> OTHER INFORMATION: MalX_DownspecR

<400> SEQUENCE: 68
gatttgattt ccacccccct tgaacaagac gcggaatgga tccaatt              47

<210> SEQ ID NO 69
<211> LENGTH: 23
<212> TYPE: DNA
<213> ORGANISM: Artificial Sequence
<220> FEATURE:
<223> OTHER INFORMATION: MalX_DownR
```

-continued

<400> SEQUENCE: 69
caccgacact atcgttaaac atg                                           23

<210> SEQ ID NO 70
<211> LENGTH: 25
<212> TYPE: DNA
<213> ORGANISM: Artificial Sequence
<220> FEATURE:
<223> OTHER INFORMATION: AliA_UpF

<400> SEQUENCE: 70
gttcaaaact aggaagggca attga                                        25

<210> SEQ ID NO 71
<211> LENGTH: 47
<212> TYPE: DNA
<213> ORGANISM: Artificial Sequence
<220> FEATURE:
<223> OTHER INFORMATION: AliA_UpspecF

<400> SEQUENCE: 71
ggagagaaag ttttaaagga gaagatcccc cgtttgattt ttaatgg                47

<210> SEQ ID NO 72
<211> LENGTH: 47
<212> TYPE: DNA
<213> ORGANISM: Artificial Sequence
<220> FEATURE:
<223> OTHER INFORMATION: AliA_UpspecR

<400> SEQUENCE: 72
ccattaaaaa tcaaacgggg gatcttctcc tttaaaactt tctctcc                47

<210> SEQ ID NO 73
<211> LENGTH: 39
<212> TYPE: DNA
<213> ORGANISM: Artificial Sequence
<220> FEATURE:
<223> OTHER INFORMATION: AliA_DownspecF

<400> SEQUENCE: 73
aattggatcc attccgcgtc gcaaaatata agaaaggat                         39

<210> SEQ ID NO 74
<211> LENGTH: 40
<212> TYPE: DNA
<213> ORGANISM: Artificial Sequence
<220> FEATURE:
<223> OTHER INFORMATION: AliA_DownspecR

<400> SEQUENCE: 74
aatcctttct tatattttgc gacgcggaat ggatccaatt               40

<210> SEQ ID NO 75
<211> LENGTH: 23
<212> TYPE: DNA
<213> ORGANISM: Artificial Sequence
<220> FEATURE:
<223> OTHER INFORMATION: AliA_DownR

<400> SEQUENCE: 75
ctatcatcaa cttcaggacc tgt                                          23

<210> SEQ ID NO 76
<211> LENGTH: 21

```
<212> TYPE: DNA
<213> ORGANISM: Artificial Sequence
<220> FEATURE:
<223> OTHER INFORMATION: SEQ ID 76 - GlnPQ_UpF

<400> SEQUENCE: 76
gaaccacctg atagccaatc t                                              21

<210> SEQ ID NO 77
<211> LENGTH: 44
<212> TYPE: DNA
<213> ORGANISM: Artificial Sequence
<220> FEATURE:
<223> OTHER INFORMATION: SEQ ID 76 - GlnPQ_UpspecF

<400> SEQUENCE: 77
tgagagaata ttcggaaaag gaggatcccc cgtttgattt ttaa                     44

<210> SEQ ID NO 78
<211> LENGTH: 47
<212> TYPE: DNA
<213> ORGANISM: Artificial Sequence
<220> FEATURE:
<223> OTHER INFORMATION: SEQ ID 76 - GlnPQ_UpspecR

<400> SEQUENCE: 78
ccattaaaaa tcaaacgggg gatcctcctt ttccgaatat tctctca                  47

<210> SEQ ID NO 79
<211> LENGTH: 35
<212> TYPE: DNA
<213> ORGANISM: Artificial Sequence
<220> FEATURE:
<223> OTHER INFORMATION: SEQ ID 76 - GlnPQ_DownspecF

<400> SEQUENCE: 79
ttggatccat tccgcgtcct gtaaggattt ccttg                               35

<210> SEQ ID NO 80
<211> LENGTH: 40
<212> TYPE: DNA
<213> ORGANISM: Artificial Sequence
<220> FEATURE:
<223> OTHER INFORMATION: SEQ ID 76 - GlnPQ_DownspecR

<400> SEQUENCE: 80
ctgcaaggaa atccttacag gacgcggaat ggatccaatt                          40

<210> SEQ ID NO 81
<211> LENGTH: 22
<212> TYPE: DNA
<213> ORGANISM: Artificial Sequence
<220> FEATURE:
<223> OTHER INFORMATION: SEQ ID 76 - GlnPQ_DownR

<400> SEQUENCE: 81
gcgaaagaag ttgtagagtg tg                                             22

<210> SEQ ID NO 82
<211> LENGTH: 20
<212> TYPE: DNA
<213> ORGANISM: Artificial Sequence
<220> FEATURE:
<223> OTHER INFORMATION: Spr1759_UpF

<400> SEQUENCE: 82
```

-continued ggaaaagacc tgccgtcaaa                                                    20

<210> SEQ ID NO 83
<211> LENGTH: 42
<212> TYPE: DNA
<213> ORGANISM: Artificial Sequence
<220> FEATURE:
<223> OTHER INFORMATION: Spr1759_UpspecF

<400> SEQUENCE: 83
caggaatttt cctacgattg agatcccccg tttgattttt aa                           42

<210> SEQ ID NO 84
<211> LENGTH: 42
<212> TYPE: DNA
<213> ORGANISM: Artificial Sequence
<220> FEATURE:
<223> OTHER INFORMATION: Spr1759_UpspecR

<400> SEQUENCE: 84
taaaaatcaa acgggggatc tcaatcgtag gaaaattcct gc                           42

<210> SEQ ID NO 85
<211> LENGTH: 35
<212> TYPE: DNA
<213> ORGANISM: Artificial Sequence
<220> FEATURE:
<223> OTHER INFORMATION: Spr1759_DownspecF

<400> SEQUENCE: 85
aattggatcc attccgcgtc ctactaacct atcag                                   35

<210> SEQ ID NO 86
<211> LENGTH: 35
<212> TYPE: DNA
<213> ORGANISM: Artificial Sequence
<220> FEATURE:
<223> OTHER INFORMATION: Spr1759_DownspecR

<400> SEQUENCE: 86
ctgataggtt agtaggacgc ggaatggatc caatt                                   35

<210> SEQ ID NO 87
<211> LENGTH: 22
<212> TYPE: DNA
<213> ORGANISM: Artificial Sequence
<220> FEATURE:
<223> OTHER INFORMATION: Spr1759_DownR

<400> SEQUENCE: 87
gaattgctca ttagggaagc ag                                                 22

<210> SEQ ID NO 88
<211> LENGTH: 22
<212> TYPE: DNA
<213> ORGANISM: Artificial Sequence
<220> FEATURE:
<223> OTHER INFORMATION: Spr0931_UpF

<400> SEQUENCE: 88
ggtgcgagaa atgttgagtg aa                                                 22

<210> SEQ ID NO 89
<211> LENGTH: 40
<212> TYPE: DNA
<213> ORGANISM: Artificial Sequence -continued

```
<220> FEATURE:
<223> OTHER INFORMATION: Spr0931_UpspecF

<400> SEQUENCE: 89
catctggcta gaccaggtgt ttgatccccc gtttgatttt                    40

<210> SEQ ID NO 90
<211> LENGTH: 41
<212> TYPE: DNA
<213> ORGANISM: Artificial Sequence
<220> FEATURE:
<223> OTHER INFORMATION: Spr0931_UpspecR

<400> SEQUENCE: 90
aaaaatcaaa cgggggatca aacacctggt ctagccagat g                 41

<210> SEQ ID NO 91
<211> LENGTH: 43
<212> TYPE: DNA
<213> ORGANISM: Artificial Sequence
<220> FEATURE:
<223> OTHER INFORMATION: Spr0931_DownspecF

<400> SEQUENCE: 91
ttggatccat tccgcgtcga gaaaagaatg ttaaagaaaa atg                43

<210> SEQ ID NO 92
<211> LENGTH: 43
<212> TYPE: DNA
<213> ORGANISM: Artificial Sequence
<220> FEATURE:
<223> OTHER INFORMATION: Spr0931_DownspecR

<400> SEQUENCE: 92
catttttctt taacattctt ttctcgacgc ggaatggatc caa                43

<210> SEQ ID NO 93
<211> LENGTH: 22
<212> TYPE: DNA
<213> ORGANISM: Artificial Sequence
<220> FEATURE:
<223> OTHER INFORMATION: Spr0931_DownR

<400> SEQUENCE: 93
aaaccaatgg ttccaatacc ag                                       22
```

LIVE ATTENUATED STRAIN OF *STREPTOCOCCUS PNEUMONIAE* AND PHARMACEUTICAL COMPOSITIONS COMPRISING A LIVE ATTENUATED STRAIN OF *S. PNEUMONIAE*

CROSS-REFERENCE TO RELATED APPLICATIONS

This application is a national stage application, filed under 35 U.S.C. § 371, of International Application No. PCT/EP2021/081568, filed Nov. 12, 2021, which claims the benefit of priority under 35 U.S.C. § 119 to GB Application No: 2017877.8, filed Nov. 12, 2020, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 12, 2021, is named Sequence Listing.txt and is 60 KB in size.

TECHNICAL FIELD

The present disclosure relates to live attenuated strains of *Streptococcus pneumoniae*, and pharmaceutical compositions comprising a live attenuated strain of *S. pneumoniae*. The live attenuated strains and pharmaceutical compositions may be used to prevent infection and boost immunity, and in particular, prevent *S. pneumoniae* infection.

BACKGROUND

*S. pneumoniae* is the dominant bacterial pathogen causing acute lung infections in adults and is responsible for up to 40 to 50% of community acquired pneumonia and 25% of exacerbations of COPD. The majority of adult *S. pneumoniae* infections occur in aged subjects or those with chronic disease, and has a pronounced peak during the winter period.

There are two existing vaccines for treatment of *S. pneumoniae* infection: the pneumococcal polysaccharide vaccine (PPV) and the conjugate vaccine (PCV). Both the PPV and PCV are based on polysaccharide capsular antigen either alone (PPV) or conjugated to a carrier protein (PCV). PPV (Pneumovax) protects against 23 *S. pneumoniae* capsular serotypes and is used in high-risk adults (aged over 65 years of age or with long term health conditions, including chronic lung disease). The conjugated polysaccharide vaccine (PCV) is routinely used for vaccination in infants.

However, these existing *S. pneumoniae* vaccines have significant drawbacks. While the pneumococcal polysaccharide vaccine (PPV) is typically used in adult risk groups, this vaccine only has a limited efficacy for preventing *S. pneumoniae* lung infections. PPV provides some protection against septicaemia, however, it provides limited protection against pneumonia and non-vaccine serotypes or non-serotypable strains; a significant cause of infections in patients with COPD.

PCV also only protects against a limited number of capsular serotypes contained within the vaccine. While PCV provides herd immunity for adults for the vaccine serotypes, a high proportion of adult disease is now increasingly caused by non-vaccine serotypes due to serotype replacement in response to the vaccination of infants.

There therefore remains a strong need for new and cost-effective approaches to prevent both adult pneumonia and infective exacerbations of COPD caused by all *S. pneumoniae* strains.

SUMMARY OF INVENTION

The details, examples and preferences provided in relation to one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

In accordance with a first aspect of the invention, there is provided a live attenuated strain of *S. pneumoniae*, the live attenuated strain comprising at least two genes or operons that have disrupted expression or encode for a protein with impaired function, wherein the at least two genes or operons are selected from fhs, piaA, proABC, spxB, Sp_1288, and Sp_1027. The at least two genes or operons listed above have a different putative function and notably, the live attenuated strains disclosed herein can still successfully colonise the nasopharynx (i.e., which is unexpected despite comprising two mutations of genes which cause reduced virulence). The live attenuated strains are also less virulent as compared with a wild-type strain.

Thus, also disclosed herein is a live attenuated strain of *S. pneumoniae*, the live attenuated strain comprising at least two genes or operons that have disrupted expression or encode for a protein with impaired function, wherein the at least two genes or operons are selected from fhs, piaA, proABC, spxB, Sp_1288, and Sp_1027, characterized in at least that the live attenuated strains can colonise the nasopharynx.

The live attenuated strains of the first aspect or described herein importantly have enhanced safety for use in medicine and human subjects as compared to strains comprising single mutants. Due to the natural competency of *S. pneumoniae* (meaning it can take up exogenous DNA), live attenuated strains comprising two disrupted virulence genes or operons, or two virulence genes or operons that encode for a protein with impaired function, reduces the risk that the attenuated strain can regain full virulence by taking up exogenous DNA. In addition to the above, there is also indication that live attenuated strains with at least two disrupted virulence genes or operons (and/or two virulence genes or operons that encode for proteins having impaired function) may have even further reduced virulence as compared to disruption of impaired function of a single virulence gene, meaning that the use of the strain is safer as compared to the use of single mutant strains. As a result, the live attenuated strains have enhanced safety as compared to single mutants such that they can be used for treatment in humans.

However, importantly, while the live attenuated strains and the live attenuated strains for use according to embodiments of the present invention are severely attenuated in virulence as compared to a wild-type strain, they notably can effectively colonise the nasopharynx to a similar density to that observed for the wild-type strain. This is important, as an inability to colonise the nasopharynx would mean that the live attenuated strain could not grow or grow as well in a patient, meaning that protective immunity would not be established or established as well, reducing the efficacy of the live attenuated strain for use a vaccine. The result is also unexpected, since the ability to colonise the nasopharynx is found to be compromised in certain mutants strains with reduced virulence, for example, ΔpsaA and Δcps mutant strains. This result is also unexpected as strains with severely attenuated virulence would be expected to have compromised or reduced nasopharyngeal colonisation.

The live attenuated strains described herein importantly can stimulate strong adaptive immunity such that the strains or pharmaceutical compositions can protect against future infection with reduced harm of infection or disease in a subject, in particular, *S. pneumoniae* infection. This is demonstrated by the production of antibodies to a similar range of protein antigens as is observed by the colonisation with wild type *S. pneumoniae*. On rechallenge/infection with *S. pneumoniae*, data disclosed herein indicates that previous colonisation with live attenuated strains of the invention leads to protection against sepsis, pneumonia or re-colonisation. Protection against infection is also demonstrated against homologous and heterologous serotypes.

The live attenuated strains of the present invention can additionally be generated in any suitable serotype, including both vaccine and non-vaccine serotypes, and can demonstrate protective immunity against infection of both homologous and heterologous serotypes. The live attenuated strains and pharmaceutical compositions described herein can therefore be used to boost immunity and prevent infection, including against serotypes for which there is less existing or vaccine induced immunity in the population.

The live attenuated strains of the present invention are found to have a high degree of genetic stability even in the absence of antibiotic selection for the mutations.

While RNA-seq data of mutant *S. pneumoniae* grown in complete laboratory media shows loss of expression of the target genes compared to the wild-type strain; no other genes show complete loss of expression. The live attenuated strains and pharmaceutical compositions described herein therefore have a good safety profile for use in boosting immunity or preventing *S. pneumoniae* infection in a subject.

The live attenuated strains of the present invention can be readily synthesised and grown according to the protocols described herein. The live attenuated strains and pharmaceutical compositions described herein may provide a more cost-effective solution for providing immunity against *S. pneumoniae* infection as compared to known PCV and PPV vaccines.

The live attenuated strains and pharmaceutical compositions described herein can be used to protect subjects against infection and boost immunity. In particular, they can be used to prevent *S. pneumoniae* infection or prevent diseases connected with *S. pneumoniae* infection in a subject.

The live attenuated strains and pharmaceutical compositions of the present invention therefore present i) a cost-effective alternative to existing vaccines, ii) protection against multiple serotypes rather than just vaccine specific serotypes and iii) enhanced mucosal immunity to improve prevention of *S. pneumoniae* respiratory tract infection and pneumonia.

Also disclosed herein, and/or in a preferred embodiment of the first aspect, there is provided a live attenuated strain of *S. pneumoniae*, the live attenuated strain comprising at least two genes or operons that have disrupted expression or encode for a protein with impaired function, wherein the at least two genes or operons include fhs. In preferred embodiments, the at least two genes or operons comprise fhs in combination with at least one of piaA, proABC, spxB, Sp_1288 and Sp_1027. In some examples, the at least two genes or operons comprise fhs and piaA. In other examples, the at least two genes or operons comprise fhs and Sp_1288.

In particular, live attenuated strains comprising fhs as one of the at least two genes or operons are found to have a marked attenuation in virulence while the ability of the live attenuated strain to colonise the nasopharynx is not significantly impaired. Disruption of fhs alone is found to severely reduce virulence and protect against pneumonia rechallenge. Double mutant strains comprising comprising fhs as one of the at least two genes or operons are in particular found to show superior results as compared with other double mutants. Live attenuated strains comprising fhs as one of the at least two genes or operons in combination with at least one other gene or operon (as exemplified by piaA) demonstrate good protective immunity against *S. pneumoniae* infection, including in humans. As far as the present inventors are aware, double mutant strains comprising fhs have not previously been reported, let alone in combination with one of the above listed genes. There has also been no suggestion in the prior art that a fhs mutant strain could be used as a live attenuated vaccine to provide protective immunity, for example, against pneumonia and sepsis. In an embodiment and in some examples, the at least two genes or operons are fhs and piaA. In an embodiment and in some examples, the at least two genes or operons are fhs and Sp_1288.

In an embodiment, the at least two genes or operons are deleted and/or mutated. In an embodiment, the at least two genes or operons have disrupted expression. In an embodiment, the expression of the at least two genes or operons is reduced by at least about 50% as compared to a wild-type strain. In an embodiment, the reduction in expression is determined by RNA-seq or by reverse transcriptase PCR. In an embodiment, the disrupted expression of the at least two genes or operons is caused by deletion and/or mutation of the at least two genes or a portion thereof. In an embodiment, the disrupted expression of the at least two genes or operons is caused by biochemical inhibition of expression or function of the at least two genes or operons.

In an embodiment, the at least two genes or operons encode for a protein with impaired function. In an embodiment, the protein with impaired function encoded by the at least two genes or operons is caused by deletion and/or mutation of the at least two genes or a portion thereof.

In accordance with a second aspect of the invention, there is provided a pharmaceutical composition comprising at least one live attenuated strain of *Streptococcus pneumoniae* according to the first aspect. In an embodiment, the pharmaceutical composition further comprises at least one of a pharmaceutically acceptable adjuvant, excipient, diluent or carrier. In an embodiment, the pharmaceutical composition is formulated as a spray, optionally a nasal spray.

In accordance with a third aspect of the invention, there is provided a pharmaceutical composition comprising two or more different live attenuated strains of *Streptococcus pneumoniae* according to the first aspect, wherein the two or more different live attenuated strains are of a different serotype. In an embodiment, the pharmaceutical composition further comprises at least one of a pharmaceutically acceptable adjuvant, excipient, diluent or carrier. In an embodiment, the pharmaceutical composition is formulated as a spray, optionally a nasal spray.

In accordance with a fourth aspect of the invention, there is provided the live attenuated strain according to the first aspect, or the pharmaceutical composition according to the second or third aspects, for use in preventing infection and/or enhancing immunity in a subject.

Also disclosed herein is a method of preventing infection and/or enhancing immunity in a subject, the method comprising administering to a subject in need thereof a therapeutically effective amount of the live attenuated strain according to the first aspect, or a pharmaceutical composition according to the second or third aspect.

Also disclosed herein, is the use of the live attenuated strain according to the first aspect, or a pharmaceutical composition according to the second or third aspect, for the manufacture of a medicament to prevent infection and/or enhance immunity in a subject.

In an embodiment of the fourth aspect, the live attenuated strain, or the pharmaceutical composition for use, prevents nasopharyngeal colonization of *S. pneumoniae*. In an embodiment of the fourth aspect, the *S. pneumoniae* infection is of homologous serotype to the serotype of the live attenuated strain. In an embodiment, the *S. pneumoniae* infection is of heterologous serotype to the serotype of the live attenuated strain. In an embodiment, the method comprises administering the live attenuated strain or the pharmaceutical composition to the upper airway of the subject. In an embodiment, the method comprises administering the live attenuated strain or the pharmaceutical composition intranasally, nasopharyngeally, to the oropharynx, subcutaneously, intradermally, intramuscularly, or a combination thereof. In an embodiment, the subject is a human In accordance with a fifth aspect of the invention, there is provided the live attenuated strain according to the first aspect, or the pharmaceutical composition according to the second or third aspects, for use in a method of preventing i) a *Streptococcus pneumoniae* infection,
    ii) pneumonia connected with *S. pneumoniae*,
    iii) septicemia connected with *S. pneumoniae*,
    iv) meningitis connected with *S. pneumoniae*
    v) an exacerbation of chronic obstructive pulmonary disease (COPD) connected with *S. pneumoniae*
    vi) acute bronchitis connected with *S. pneumoniae*
    vii) acute sinusitis connected with *S. pneumoniae* or
    viii) acute otitis media connected with *S. pneumoniae* in a subject.

Also disclosed herein is a method of preventing
    i) a *Streptococcus pneumoniae* infection,
    ii) pneumonia connected with *S. pneumoniae*,
    iii) septicemia connected with *S. pneumoniae*,
    iv) meningitis connected with *S. pneumoniae*
    v) an exacerbation of chronic obstructive pulmonary disease (COPD) connected with *S. pneumoniae*
    vi) acute bronchitis connected with *S. pneumoniae*
    vii) acute sinusitis connected with *S. pneumoniae* or
    viii) acute otitis media connected with *S. pneumoniae*
wherein the method comprises administering to a subject in need thereof a therapeutically effective amount of the live attenuated strain according to the first aspect, or a pharmaceutical composition according to the second or third aspect.

Also disclosed herein, is the use of the live attenuated strain according to the first aspect, or a pharmaceutical composition according to the second or third aspect, for the manufacture of a medicament to prevent
    i) a *Streptococcus pneumoniae* infection,
    ii) pneumonia connected with *S. pneumoniae*,
    iii) septicemia connected with *S. pneumoniae*,
    iv) meningitis connected with *S. pneumoniae*
    v) an exacerbation of chronic obstructive pulmonary disease (COPD) connected with *S. pneumoniae*
    vi) acute bronchitis connected with *S. pneumoniae*
    vii) acute sinusitis connected with *S. pneumoniae* or viii) acute otitis media connected with *S. pneumoniae* in a subject.

In embodiments of the fifth aspect, the *S. pneumoniae* infection is of homologous serotype to the serotype of the live attenuated strain for use. In an embodiment, the *S. pneumoniae* infection is of heterologous serotype to the serotype of the live attenuated strain for use. In an embodiment, the method comprises administering the live attenuated strain or the pharmaceutical composition to the upper airway of the subject. In an embodiment, the method comprises administering the live attenuated strain or the pharmaceutical composition intranasally, nasopharyngeally, to the oropharynx, subcutaneously, intradermally, intramuscularly, or a combination thereof. In an embodiment, the subject is a human.

In accordance with a sixth aspect, there is provided a live attenuated strain for use in a method of preventing
    i) a *Streptococcus pneumoniae* infection,
    ii) pneumonia connected with *Streptococcus pneumoniae*
    iii) septicemia connected with *Streptococcus pneumoniae*,
    iv) meningitis connected with *S. pneumoniae*
    v) an exacerbation of chronic obstructive pulmonary disease (COPD) connected with *Streptococcus pneumoniae*
    vi) acute bronchitis connected with *S. pneumoniae*
    vii) acute sinusitis connected with *S. pneumoniae* or
    viii) acute otitis media connected with *S. pneumoniae* in a subject, wherein the live attenuated strain comprises at least one gene or operon that has disrupted expression or encodes for a protein with impaired function, wherein the at least one gene or operon is selected from fhs, proABC, Sp_1288 or Sp_1027, preferably fhs. In a preferred embodiment, the live attenuated strain comprises at least two genes or operons that have disrupted expression or encodes for a protein with impaired function, wherein at least one of the at least two genes or operons is fhs.

Also disclosed herein is a method of preventing
    i) a *Streptococcus pneumoniae* infection,
    ii) pneumonia connected with *S. pneumoniae*,
    iii) septicemia connected with *S. pneumoniae*,
    iv) meningitis connected with *S. pneumoniae*
    v) an exacerbation of chronic obstructive pulmonary disease (COPD) connected with *S. pneumoniae*
    vi) acute bronchitis connected with *S. pneumoniae*
    vii) acute sinusitis connected with *S. pneumoniae* or
    viii) acute otitis media connected with *S. pneumoniae*
wherein the method comprises administering to a subject in need thereof a therapeutically effective amount of a live attenuated strain that comprises at least one gene or operon that has disrupted expression or encodes for a protein with impaired function, wherein the at least one gene or operon is selected from fhs, proABC, Sp_1288 or Sp_1027, preferably fhs. In a preferred embodiment, the live attenuated strain comprises at least two genes or operons that have disrupted expression or encodes for a protein with impaired function, wherein at least one of the at least two genes or operons is fhs.

Also disclosed herein, is the use of a live attenuated strain for the manufacture of a medicament to prevent
    i) a *Streptococcus pneumoniae* infection,
    ii) pneumonia connected with *S. pneumoniae*,
    iii) septicemia connected with *S. pneumoniae*,
    iv) meningitis connected with *S. pneumoniae*
    v) an exacerbation of chronic obstructive pulmonary disease (COPD) connected with *S. pneumoniae*
    vi) acute bronchitis connected with *S. pneumoniae* vii) acute sinusitis connected with *S. pneumoniae* or viii) acute otitis media connected with *S. pneumoniae* wherein the live attenuated strain comprises at least one gene or operon that has disrupted expression or encodes for a protein with impaired function, and wherein the at least one gene or operon is selected from fhs, proABC, Sp_1288 or Sp_1027, preferably fhs. In a preferred embodiment, the live attenuated strain comprises at least two genes or operons that have disrupted expression or encodes for a protein with impaired function, wherein at least one of the at least two genes or operons is fhs.

In an embodiment, the least one gene is deleted and/or mutated. In an embodiment, the at least one gene or operon has disrupted expression. In an embodiment, the expression of the at least one gene or operon is reduced by at least about 50% as compared to a wild-type strain. In an embodiment, the reduction in expression is determined by RNA-seq or by reverse transcriptase PCR. In an embodiment, the disrupted expression of the at least one gene or operon is caused by deletion and/or mutation of the at least one gene or a portion thereof. In an embodiment, the disrupted expression of the at least one gene or operon is caused by biochemical inhibition of expression or function of the at least one gene or operon. In an embodiment, the at least one gene or operon encodes for a protein with impaired function. In an embodiment, the impaired function of the protein encoded by the at least one gene or operon is caused by deletion and/or mutation of the at least one gene or a portion thereof. In an embodiment, the live attenuated strain further comprises an antibiotic resistance cassette, optionally a spectinomycin or kanamycin resistance cassette. In some embodiments, the gene deletion cassette does not contain an antibiotic resistance cassette.

In embodiments of sixth aspect, the *S. pneumoniae* infection is of homologous serotype to the serotype of the live attenuated strain for use. In an embodiment, the *S. pneumoniae* infection is of heterologous serotype to the serotype of the live attenuated strain for use. In an embodiment, the method comprises administering the live attenuated strain or the pharmaceutical composition to the upper airway of the subject. In an embodiment, the method comprises administering the live attenuated strain or the pharmaceutical composition intranasally, nasopharyngeally, to the oropharynx, subcutaneously, intradermally, intramuscularly, or a combination thereof. In an embodiment, the subject is a human.

Also disclosed herein, is a method of making the live attenuated strain of *S. pneumoniae* of the first aspect, the method comprising providing a wild-type strain of *S. pneumoniae*, and deleting and/or mutating at least two genes or operons, wherein the at least two genes or operons are selected from fhs, piaA, proABC, spxB, Sp_1288, and Sp_1027. Also disclosed herein, is a live attenuated strain obtained by this method. The live attenuated strain obtained by this method may be used in the second, third, fourth or fifth aspects.

Also disclosed herein, is a method of making the live attenuated strain of *Streptococcus pneumoniae* for use according to the sixth aspect, the method comprising providing a wild-type strain of *S. pneumoniae*, and deleting and/or mutating at least one gene or operon, wherein the at least one gene or operon is selected from fhs, proABC, Sp_1288, and Sp_1027. Also disclosed herein, is the live attenuated strain obtained by this method, which may be used in the sixth aspect.

Also disclosed herein, is the live attenuated strain of the first aspect, or the pharmaceutical compositions of the second or third aspect, for use in a method of preventing nasopharyngeal colonization of *S. pneumoniae* in a subject.

Also disclosed herein, is a method of preventing nasopharyngeal colonization of *S. pneumoniae* in a subject, wherein the method comprises administering to a subject in need thereof a therapeutically effective amount of the live attenuated strain according to the first aspect, or a pharmaceutical composition according to the second or third aspect.

Also disclosed herein, a live attenuated strain for use in a method of preventing nasopharyngeal colonization of *S. pneumoniae* in a subject, wherein the live attenuated strain comprises at least one gene or operon that has disrupted expression or encodes for a protein with impaired function, and wherein the at least one gene or operon is selected from fhs, proABC, Sp_1288 or Sp_1027.

Also disclosed herein is a method of preventing nasopharyngeal colonization of *S. pneumoniae* in a subject, wherein the method comprises administering to a subject in need thereof a therapeutically effective amount of a live attenuated strain that comprises at least one gene or operon that has disrupted expression or encodes for a protein with impaired function, and wherein the at least one gene or operon is selected from fhs, proABC, Sp_1288 or Sp_1027.

BRIEF DESCRIPTION OF FIGURES

Embodiments of the present invention may be described with the reference, by way of example only, to the following figures.

*pneumoniae* strains protects against pneumonia and systemic infection after challenge with a wild type 6B *S. pneumoniae* strain.

FIG. 9 shows how nasopharynx colonisation with the example ΔproABC/piaA or Δfhs/piaA live attenuated *S. pneumoniae* strains protects against recolonisation with the homologous 6B or the heterologous TIGR4 strains.

Figure 10A:
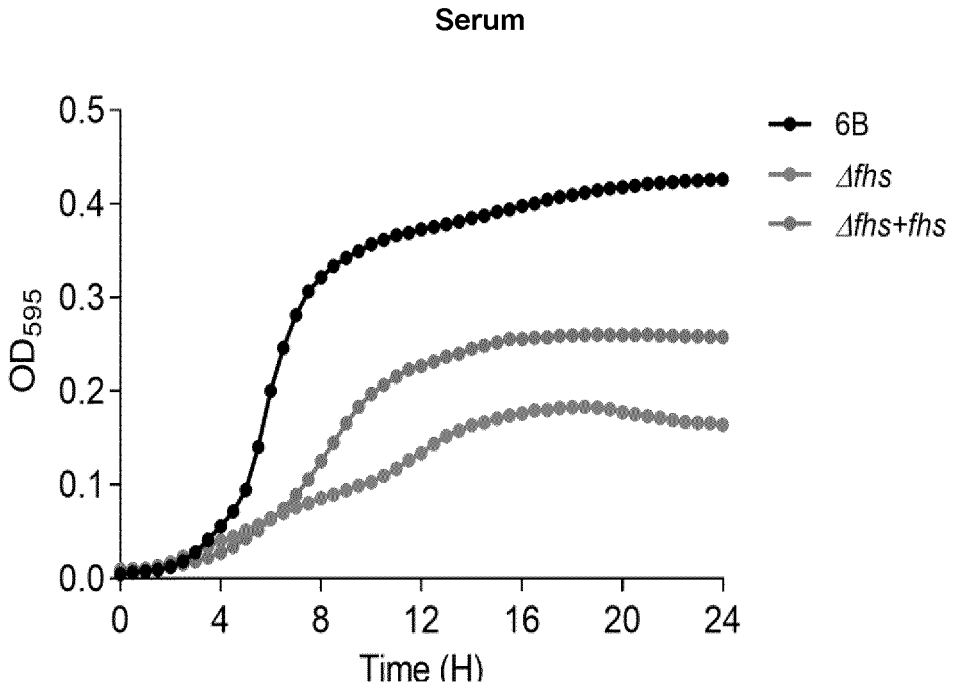
Figure 10A:
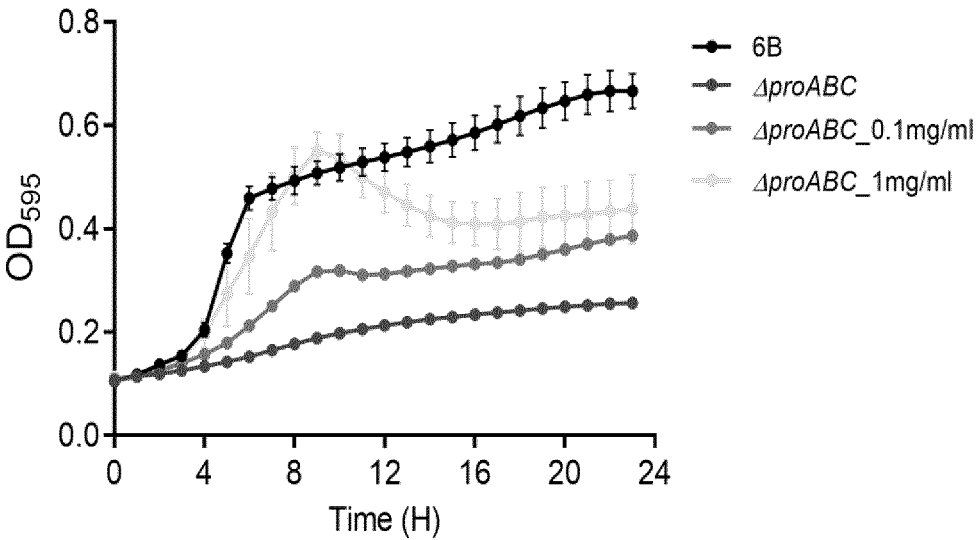
Figure 10B:
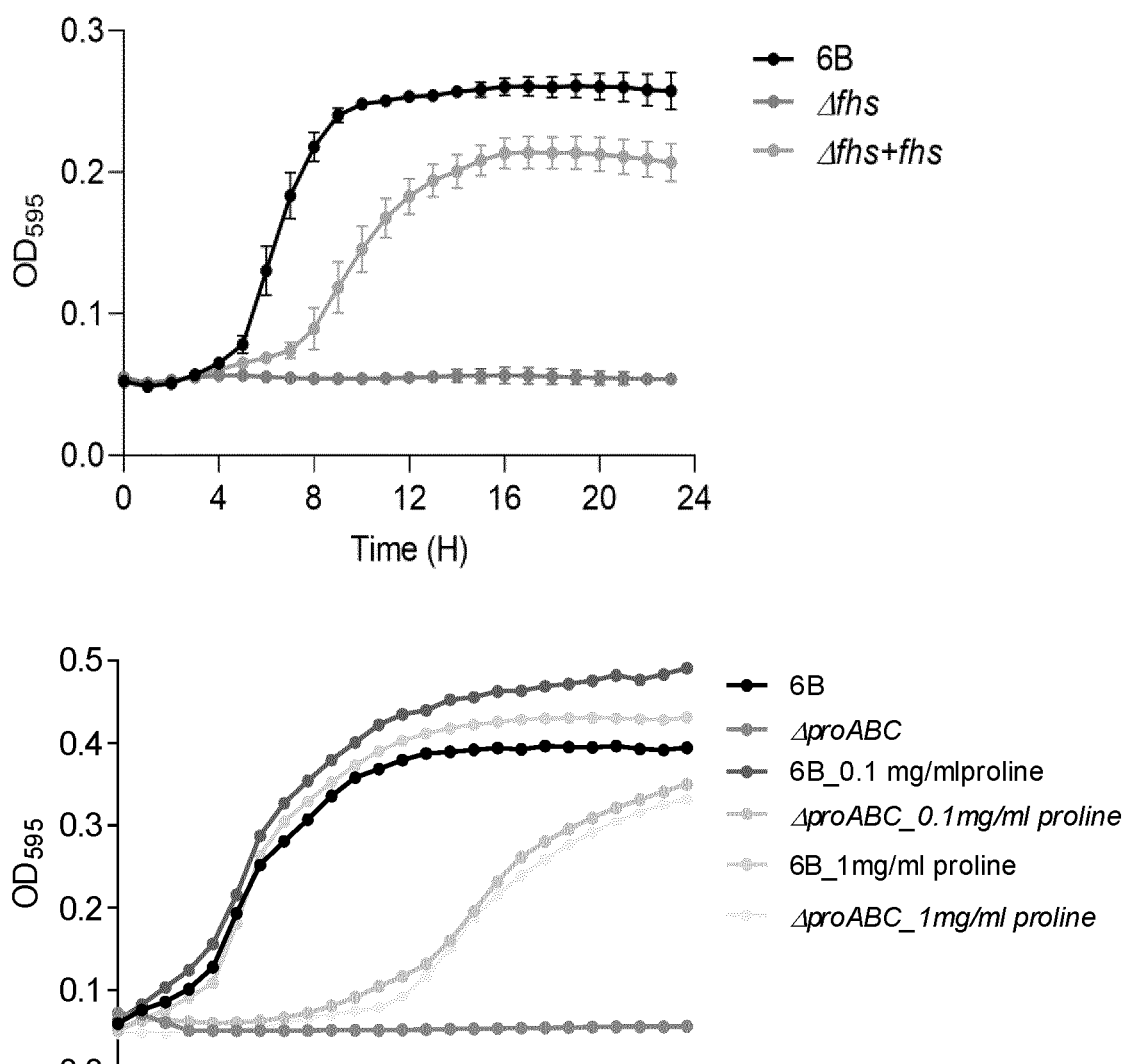

FIG. 10 shows the replicaton of *S. pneumoniae* strains (6B, Δfhs mutant strains, or ΔproABC mutant strains) in human sera obtained from healthy volunteers or cerebrospinal fluid (CSF) from patients with normal pressure hydrocephalus was determined by inoculating with $\kappa \times 10^6$ CFU/well in a 200 μl volume and monitoring growth by measuring optical density ($OD_{595}$) every 30 minutes for 24 hours using a TECAN Spark® plate reader.

Figure 11:
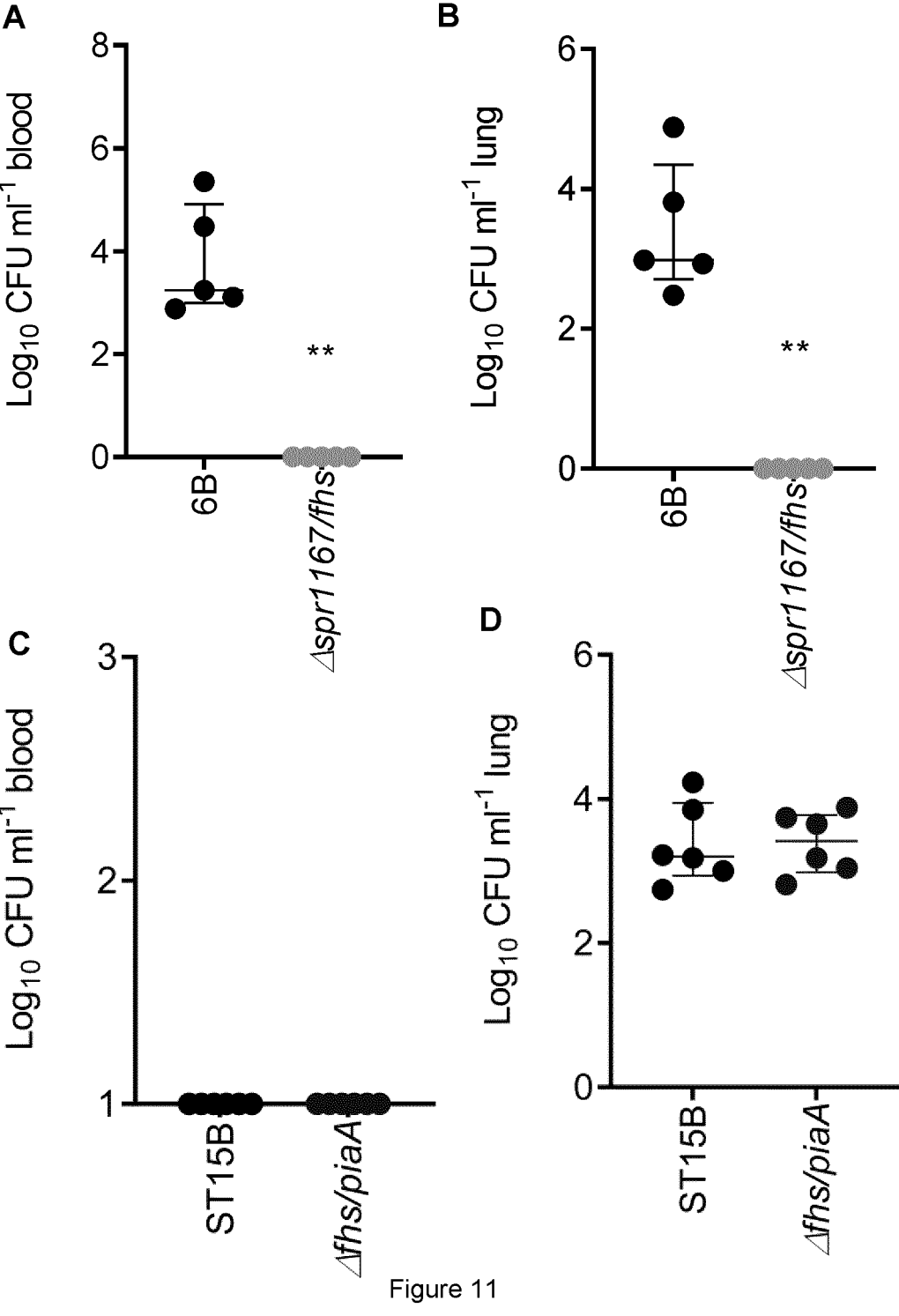

FIG. 11 shows the virulence of double mutant strains in murine pneumonia model. (A, B) CFU obtained from blood (A) and lung (B) of CD1 mice 24 h post intranasal inoculation with $1 \times 10^7$ CFU of wild type 6B or double mutant ΔSp_1288/fhs (i.e., otherwise referred to and shown in the Figure as spr1167/fhs). (C, D) CFU in blood (C) or lung (D) of CD1 mice 24 h post intranasal inoculation with $1 \times 10^7$ CFU of wild type 15B or double mutant Δfhs/piaA. Each symbol represents CFU data from a single mouse, horizontal bars represent median values, error bars represent interquartile range and asterisks represent statistical significance compared to the wild type strain (Kruskal-Wallis with Dunn's post hoc test to identify significant differences between groups, * p<0.05; ** p<0.01).

Figure 12:
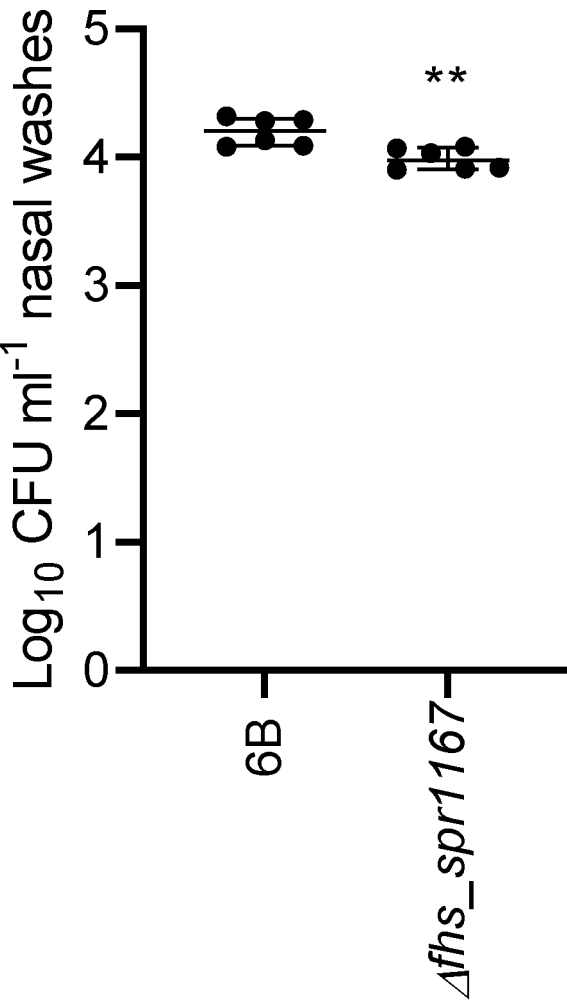

FIG. 12 shows a colonisation model; nasal wash CFU 7 days post colonisation of CD1 mice with $1 \times 10^7$ CFU of wild type 6B or the double mutant *S. pneumoniae* ΔSp_1288/fhs 6B strain (i.e., otherwise referred to and shown in the Figure as Δspr1167/fhs 6B strain). Each symbol represents CFU data from a single mouse, horizontal bars represent median values, error bars represent interquartile range and asterisks represent statistical significance compared to the wild type strain (Mann Whitney U test; ** p<0.01).

Figure 13:
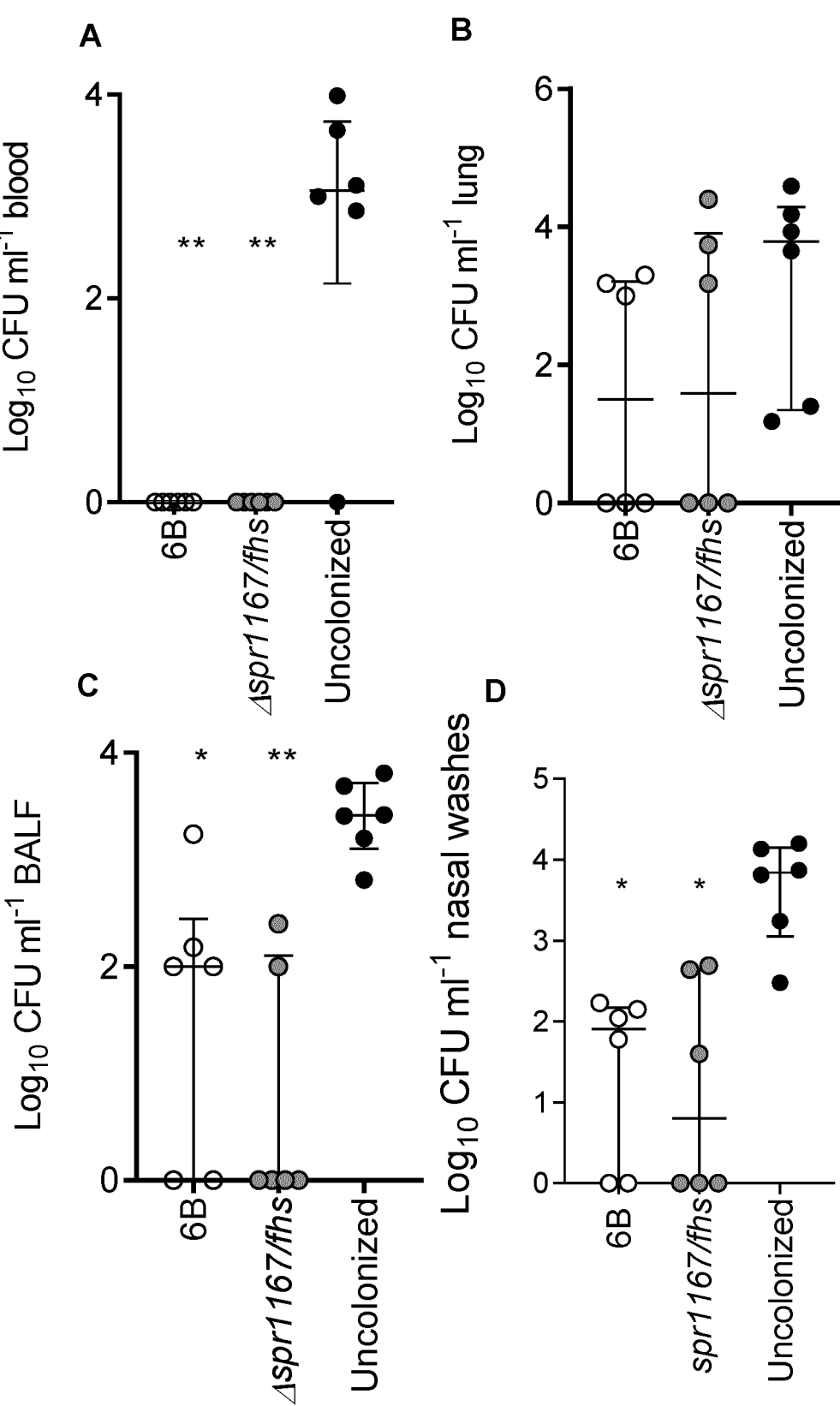

FIG. 13 shows the rechallenge of mice previously colonised with 6B and the double mutant attenuated strain ΔSp_1288/fhs (otherwise referred to and shown in the Figure as Δspr1167/fhs) using wild type 6B and pneumonia and colonisation models. (A-C) Target organ CFU for sham-colonised, 6B colonised, or double mutant strain colonised CD1 mice challenged 30 days after colonisation by intranasal inoculation of $1 \times 10^7$ CFU wild type 6B *S. pneumoniae*. (A) Blood, (B) lung homogenate and (C) BALF *S. pneumoniae* CFU (log 10 ml-1) 24 hours following the pneumonia challenge. (D) Nasal wash CFU 7 days after intranasal recolonisation challenge of CD1 mice with $1 \times 10^7$ CFU of the *S. pneumoniae* 6B strain 42 days after two episodes of colonisation with the wild type 6B or double mutant strain. Each symbol represents data from a single mouse, horizontal bars represent median values, error bars represent interquartile range and asterisks represent statistical significance compared to sham colonised group (Kruskall-Wallis with Dunn's post hoc test; *, p<0.05; **, p<0.01).

Figure 14:
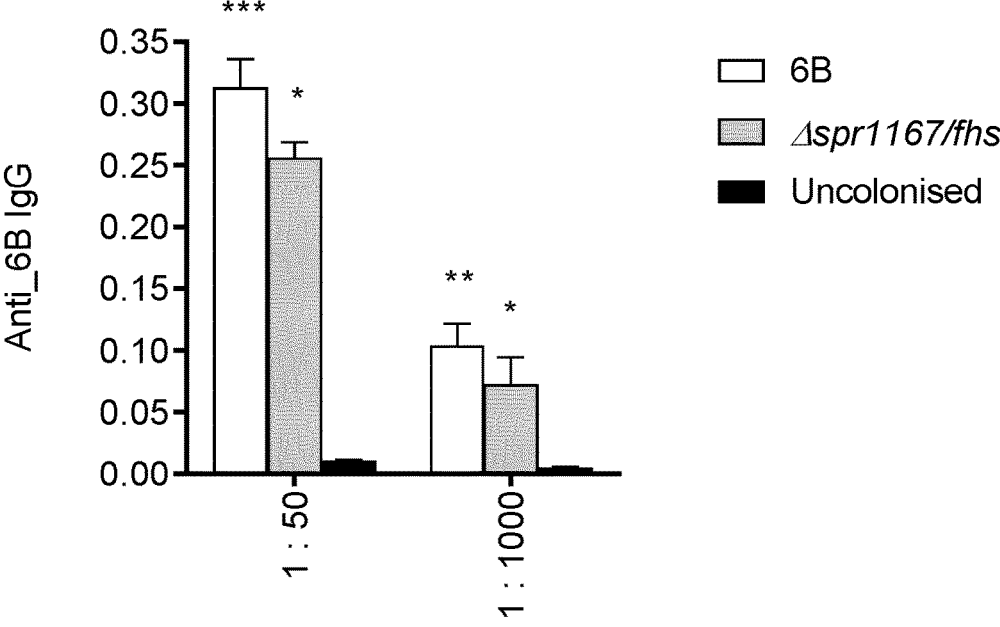

FIG. 14 shows wild type 6B and the double mutant strain Δ Sp_1288/fhs (otherwise referred to and shown in the Figure as Δspr1167/fhs) induce a systemic antibody response after nasopharynx colonisation. (A) Whole-cell enzyme-linked immunosorbent assay (ELISA) anti-6B immunoglobulin (Ig) G responses in mouse sera 28 days post-colonisation with the corresponding strain 6B (white bars), ΔSp_1288/fhs mutant (grey bars), compared with uncolonised controls (black bars).

N=6 for each group and the data analysed using Kruskal-Wallis with Dunn's post hoc test to identify significant differences between selected groups; *, p<0.05; , p<0.01 **, p<0.0001.

Figure 15:
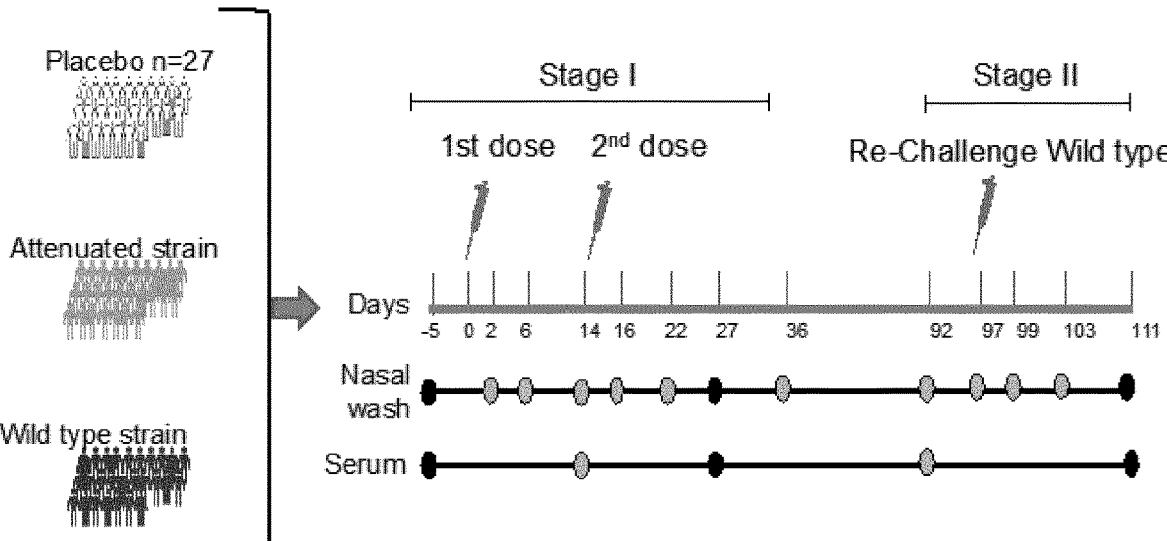

FIG. 15 shows the design of the human challenge study using *S. pneumoniae* mutant stains.

DETAILED DESCRIPTION

The terms "treatment" and "treating" herein refer to an approach for obtaining beneficial or desired results in a subject, which includes a prophylactic benefit and optionally also a therapeutic benefit.

"Prophylactic benefit" refers to delaying or eliminating the appearance of a disease or condition, delaying or eliminating the onset of symptoms of a disease or condition, slowing, halting, or reversing the progression of a disease or condition, or any combination thereof. In the context of the present invention, the prophylactic benefit or effect may involve the prevention of infection, for example, *S. pneumoniae* infection. The live attenuated strain or pharmaceutical composition may be administered to a subject at risk of developing a particular disease, or to a subject reporting one or more of the physiological symptoms of a disease, even though a diagnosis of this disease may not have been made.

"Therapeutic benefit" refers to eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the patient may still be afflicted with the underlying disorder.

The term "effective amount" or "therapeutically effective amount" refers to the amount of the live attenuated strain or pharmaceutical composition needed to bring about an acceptable outcome of the therapy as determined by reducing the likelihood of disease as measurable by clinical, biochemical or other indicators that are familiar to those trained in the art. The therapeutically effective amount may vary depending upon the infection, the subject, e.g., the weight and age of the subject and the mode of administration and the like, which can readily be determined by one of ordinary skill in the art.

The term "subject" refers to any suitable subject, including any animal, such as a mammal. In an embodiment, the subject is a human.

The term "comprising" (and related terms such as "comprise" or "comprises" or "having" or "including") includes those embodiments, for example, an embodiment of any composition of matter, composition, method, or process, or the like, that "consist of" or "consist essentially of" the described features. The term "comprises" or "comprising" can be used interchangeably with "includes".

The term "sequence identity" refers to the relatedness between nucleotide sequences as determined by comparing the sequences, and identical matches between nucleotides in correspondingly identical positions in the sequences being compared. Levels of identity between genes can be calculated using known methods, for example, sequence identity can be determined using BLAST (i.e. Basic Local Alignment Search Tool).

The term "wild-type" or "wild-type strain" referred to herein, relates to the phenotype of the typical form of a strain as it occurs in nature, for example, with no genetic modification. Unless otherwise described herein, when comparing the live attenuated strains of the present invention to that of the wild type strain, the live attenuated strains and the wild-type strains have been treated or cultured under the same growth conditions.

The "D39" strain as referred to herein may otherwise refers to a strain of *S. pneumoniae* of serotype 2.

The "TIGR4" strain as referred to herein strain may otherwise refers to a strain of *S. pneumoniae* of serotype 4.

The term "RNA-seq" referred to herein, otherwise known as "RNA sequencing", refers to a next-generation sequencing technology which reveals the presence and quantity of RNA in a sample which can be used to analyse the cellular transcriptome.

When ranges are used herein, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range may vary. Typical experimental variabilities may stem from, for example, changes and adjustments necessary during scale-up from laboratory experimental and manufacturing settings to large scale.

The features of any dependent claim may be readily combined with the features of any of the independent claims or other dependent claims.

It must be noted that as used herein and in the appended claims, the singular forms "a", "an", and "the" include plural referents unless the context clearly dictates otherwise.

Unless defined otherwise, all technical and scientific terms used herein have the same meanings as commonly understood by one of ordinary skill in the art to which this invention belongs. Abbreviations used herein have their conventional meaning within the chemical and biological arts, unless otherwise indicated.

Live Attenuated Strains
*Streptococcus pneumoniae*

*Streptococcus pneumoniae* as described herein refers to a species of gram-positive bacteria of the genus Streptococcus. *S. pneumoniae* is otherwise known as and may otherwise be described in herein as *S. pneumoniae*. *S. pneumoniae* is also otherwise known as pneumococcus.

The live attenuated strain of *S. pneumoniae* as described herein is a strain *S. pneumoniae* that has reduced virulence and pathogenicity as compared to a wildtype strain (i.e. rendering it less harmful to a host or subject), while maintaining its viability (i.e. the strain is alive and replication-competent). In an embodiment, the live attenuated strain is a genetically modified variant or a mutant of the wildtype.

The *S. pneumoniae* strain may be any suitable serotype, of which there are over 90 serotypes currently known. In an embodiment, the live attenuated strain may be of vaccine serotype (e.g. 1, 3, 4, 5, 6A, 6B, 7F, 9V, 14, 18C, 19A, 19F, and 23F) or of non-vaccine serotype. In some embodiments, the live attenuated strain may provide protective immunity against vaccine serotypes (for example, at least as well as existing vaccines), while also providing protective immunity against non-vaccine serotypes.

In some embodiments, the *S. pneumoniae* serotype may be selected from 1, 2, 3, 4, 5, 6A, 6B 6C, 6C, 6D, 6E, 6F, 6G, 6H, 7A, 7B, 7C, 7F, 8, 9A, 9L, 9N, 9V, 10F, 10A, 10B, 10C, 11F, 11A, 11B, 11C, 11D, 11E, 12F, 12A, 12B, 13, 14, 15F, 15A, 15B, 15C, 16F, 16A, 17F, 17A, 18F, 18A, 18B, 18C, 19F, 19A, 19B, 19C, 20A, 20B, 21, 22F, 22A, 23F, 23A, 23B, 23C, 24F, 24A, 24B, 25F, 25A, 27, 28F, 28A, 29, 31, 32F, 32A, 33F, 33A, 33B, 33C, 33D, 33E, 34, 35F, 35A, 35B, 35C, 36, 37, 38, 39, 40, 41F, 41A, 42, 43, 44, 45, 46, 47F, 47A, 48. In an embodiment, the serotype is 15B. In an embodiment, the serotype is 6B.

In an embodiment, the strain may be a capsulated or non-capsulated serotype. In an embodiment, the strain is of a capsulated serotype. In some examples, capsulated serotypes are found to more successfully colonise the nasopharynx as compared to non-capsulated serotypes.

The live attenuated strains described herein may demonstrate any suitable degree of attenuation such that the live attenuated strain is safe to use in a host or subject while providing protective immunity.

In some embodiments, the live attenuated strain is less virulent as compared to a wild-type strain. In some embodiments, the live attenuated strain may be present in the blood in an amount 10× less compared to the wild-type strain 24-48 hours after intranasal inoculation of the strain, or at least 50× less, or at least 100× less, or the live attenuated strain is present in the blood in an amount 1000× less as compared to the wild-type strain 24-48 hours after intranasal inoculation of the strain. In an embodiment, this is measured by comparing the CFU/ml in the blood 28 hours after intranasal inoculation of the strain in a pneumonia mouse model.

In some embodiments, the live attenuated strain is present in the lung in an amount at least 3× less compared to the wild-type strain 24-48 hours after intranasal inoculation of the strain, or at least 4× less, or at least 5× less, or at least 6× less, or at least 7× less, or at least 8× less, or at least 9× less, or the live attenuated strain is present in the lung in an amount at least 10× less compared to the wild-type strain 24-48 hours after intranasal inoculation of the strain. In an embodiment, this is determined by comparing the CFU/ml in the lung 28 hours after intranasal inoculation of the strain in a pneumonia mouse model.

In some embodiments, the live attenuated strain is present in the blood in an amount at least 10× less compared to the wild-type strain 24-48 hours after intraperitoneal inoculation of the strain, or at least 50× less, or at least 100× less, or at least 250× less, or the live attenuated strain is present in the blood in an amount at least 1000× less as compared to the wild-type strain 24-48 hours after intraperitoneal inoculation of the strain. In an embodiment, this is determined by comparing the CFU/ml in the blood 24 hours, post intraperitoneal inoculation in a sepsis mouse model.

In some embodiments, the live attenuated strain is present in the spleen at least 10× less compared to the wild-type strain 24-48 hours after intraperitoneal inoculation of the strain, or at least 50× less, or at least 100× less, or at least 250× less, or the live attenuated strain is present in the spleen in an amount at least 1000× less compared to the wild-type strain 24-48 hours after intraperitoneal inoculation of the strain. In an embodiment, this is determined by comparing the CFU/ml in the spleen 24 hours post intraperitoneal inoculation in a sepsis mouse model.

The live attenuated strains described herein are able to effectively colonise the nasopharynx. In some embodiments, the live attenuated strain can colonise the nasopharynx to a level which is at least 25% of the level observed for the wild-type strain, or at least 30%, or at least 35%, or at least 40%, or at least 45%, or at least 50%, or at least 55%, or at least 60%, or at least 65%, or at least 70% or at least 75%, or at least 80%, or at least 85%, or at least 90%, or at least 95%, or at least 99%, or the live attenuated strain can colonise the nasopharynx at least to the level as observed for the wild-type strain. In an embodiment, this may be determined by comparing the CFU in nasal washes of mice (e.g.

CD1 mice) 7 days post colonisation with either the live attenuated or wild-type strain.

The live attenuated strains described herein may provide immunity or protective efficacy to *S. pneumoniae* infection when administered to a subject. In some embodiments, prior colonisation of the nasopharynx with the live attenuated strain leads to at least a 10-fold reduction in *S. pneumoniae* infection in the blood when subsequently challenged or infected with a virulent form of *S. pneumoniae* (e.g. the wildtype) as compared to an uncolonised negative control, or at least a 100-fold reduction in infection, or at least an 1000-fold reduction in *S. pneumoniae* infection, or at least a 10000-fold reduction in *S. pneumoniae* infection in the blood when subsequently challenged or infected with a virulent form of *S. pneumoniae* (e.g. the wildtype) as compared to an uncolonised negative control. In some embodiments, prior colonisation of the nasopharynx with the live attenuated strain leads to at least a 5-fold reduction in *S. pneumoniae* infection in the lung when subsequently challenged or infected with a virulent form of *S. pneumoniae* (e.g. the wildtype) as compared to an uncolonised negative control, or at least a 10-fold reduction in *S. pneumoniae* infection, or at least a 50-fold reduction in *S. pneumoniae* infection, or at least an 100-fold reduction in *S. pneumoniae* infection in the lung when subsequently challenged or infected with a virulent form of *S. pneumoniae* (e.g. the wildtype) as compared to an uncolonised negative control. In some embodiments, prior colonisation of the nasopharynx with the live attenuated strain leads to at least a 10-fold reduction in *S. pneumoniae* infection in bronchoalveolar lavage fluid (BALF) when subsequently challenged or infected with a virulent form of *S. pneumoniae* (e.g. the wildtype) as compared to an uncolonised negative control, or at least a 100-fold reduction in infection, or at least an 1000-fold reduction in *S. pneumoniae* infection in bronchoalveolar lavage fluid (BALF) as compared to an uncolonised negative control when subsequently challenged or infected with a virulent form of *S. pneumoniae* (e.g. the wildtype). In all such embodiments, this may be determined by measuring CFU/ml 24 hours post infection in a mouse model. In some embodiments, the virulent form of *S. pneumoniae* used in the challenge is of homologous serotype. In some embodiments, the virulent form of *S. pneumoniae* used in the challenge is of heterologous serotype.

Prior-colonisation of the live attenuated strain described herein may provide a protective immunological response against infection in the form of antibodies. The live attenuated strain described herein may provide a protective immunological response against *S. pneumoniae* infection in the form of antibodies. In an embodiment, prior-colonisation provides a protective effect of at least 2 years after colonisation, or at least 1 year, or at least 6 months, or at least 3 months, or at least 30 days after colonisation.

In some embodiments, cells colonised with the live attenuated strain demonstrate a larger IgG response as compared to uncolonised cells after challenge or infection with a virulent form of *S. pneumoniae* (e.g. the wildtype).

In some embodiments, cells colonised with the live attenuated strain demonstrate an IgG response which is at least 30% of the IgG response observed when colonised with the wildtype strain after challenge or infection with a virulent form of *S. pneumoniae*, or at least 40%, or at least 50%, or at least 60%, or at least 70%, or at least 80%, or at least 90%, or at least 95%, or at least 100% of the IgG response observed when colonised with the wildtype strain after challenge or infection with a virulent form of *S. pneumoniae*. In some embodiments, the virulent form of *S. pneumoniae* used in the challenge is of homologous serotype. In some embodiments, the virulent form of *S. pneumoniae* used in the challenge is of heterologous serotype. In an embodiment, IgG levels are measured by whole-cell ELISA IgG post colonisation with the strain in a mouse model. In an embodiment, the IgG levels are measured 28 days after colonisation.

In some embodiments, cells colonised with the live attenuated strain demonstrate a larger IgG response as compared to uncolonised cells in response to non-capsular antigens. In some embodiments, cells colonised with the live attenuated strain demonstrate an IgG response which is at least 30%, or at least 40%, or at least 50%, or at least 60%, or at least 70%, or at least 80%, or at least 90%, or at least 95%, or at least 100% of the IgG response observed when colonised with the wildtype strain in response to non-capsular antigens. In an embodiment, the non-capsular antigens include PsaA, StkP; Mlt; SP_1174, BgaA; PspA F2, RrgA T4, PiuA, PiaA, Ply, RrgB T4 RrgB 6B or a combination thereof. In an embodiment, IgG levels are measured by whole-cell ELISA IgG post colonisation with the strain in a mouse model. In an embodiment, the IgG levels are measured 28 days after colonisation.

The live attenuated strains described herein may provide a protective cellular immunological response against infection. The live attenuated strains described herein may provide a protective cellular immunological response against *S. pneumoniae* infection. In some embodiments, the protective cellular response includes include macrophages and neutrophils, T cells, CD4+ cells or CD8+ cells, for example, CD4+ cells.

Genes

According to the first aspect, the live attenuated strain of *Streptococcus pneumoniae* comprises at least two genes or operons that have disrupted expression or encode for a protein with impaired function, wherein the at least two genes or operons are selected from fhs, piaA, proABC, spxB, Sp_1288, and Sp_1027. Since disrupted expression of fhs, piaA, proABC, spxB, Sp_1288, and Sp_1027 are each individually found to reduce virulence of the live attenuated strain as compared to a wildtype, the selection of at least two of these genes or operons can result in a live attenuated strain that has even further reduced virulence as compared to a wild-type strain, meaning the live attenuated strain is less harmful to a host. The at least two genes or operons have a different putative function such that their effect on virulence may be additive or even synergistic. Furthermore, disruption of or impaired function of fhs, piaA, proABC, spxB, Sp_1288, and Sp_1027 individually are found not to impact the ability of the live attenuated strain to colonize the nasopharynx (see single mutant model data), thus the at least two genes or operons with disrupted expression or impaired function are both selected such that the colonisation and viability of the live attenuated strain is minimally impaired. The at least two disrupted genes or operons (or at least two gene or operons that encode for proteins with impaired function) being selected from fhs, piaA, proABC, spxB, Sp_1288, and Sp_1027 can also improve the safety of the live attenuated strain for use in a host or subject, since there is reduced likelihood that the live attenuated strain will revert (e.g. by taking up exogenous DNA) to its harmful virulent (e.g. wildtype) form.

In an embodiment, the at least two genes or operons comprise fhs in combination with at least one gene or operon selected from piaA, proABC, spxB, Sp_1288 or Sp_1027. In an embodiment, the at least two genes or operons comprise fhs in combination with piaA. In an embodiment, the at least two genes or operons comprise fhs in combination with Sp_1288. In an embodiment, the at least two genes or operons comprise fhs in combination with proABC. Live attenuated strains comprising fhs as one of the at least two genes or operons are found to have a marked attenuation in virulence with the ability of the live attenuated strain to colonise the nasopharynx is not significantly impaired. Disruption of fhs alone is found to severely reduce virulence and protect against pneumonia rechallenge. Live attenuated strains comprising fhs as one of the at least two genes or operons in combination with at least one other gene or operon (as exemplified by piaA) demonstrate good protective immunity against S. pneumoniae infection.

In an embodiment, the at least two genes or operons comprise piaA in combination with at least one gene or operon selected from fhs, proABC, spxB, Sp_1288 or Sp_1027. In an embodiment, the at least two genes comprise piaA in combination with at least one gene or operon selected from fhs or proABC. Live attenuated strains comprising piaA as one of the at least two genes or operons are found to have a marked attenuation in virulence with the ability of the live attenuated strain to colonise the nasopharynx not significantly impaired. Live attenuated strains comprising piaA as one of the at least two genes or operons in combination with at least one other gene or operon (as exemplified by fhs or proABC) demonstrate good protective immunity against S. pneumoniae infection.

In an embodiment, the at least two genes or operons comprise proABC in combination with at least one gene selected from fhs, piaA, spxB, Sp_1288 or Sp_1027. In an embodiment, the at least two genes or operons comprise proABC in combination with piaA. In an embodiment, the at least two genes or operons comprise proABC in combination with fhs. Live attenuated strains comprising proABC as one of the at least two genes or operons are found to have a marked attenuation in virulence with the ability of the live attenuated strain to colonise the nasopharynx not significantly impaired. Disruption of proABC alone is found to severely reduce virulence. Live attenuated strains comprising proABC as one of the at least two genes or operons in combination with at least one other gene or operon (as exemplified by piaA) demonstrate good protective immunity against S. pneumoniae infection. In an embodiment, the at least two genes or operons include proABC in combination with at least one of fhs, piaA, spxB, Sp_1288 and Sp_1027.

In an embodiment, the at least two genes or operons include spxB in combination with at least one of fhs, spxB, proABC, Sp_1288 and Sp_1027. In an embodiment, the at least two genes or operons include Sp_1288 in combination with at least one of fhs, piaA, proABC, spxB and Sp_1027. In an embodiment, the at least two genes or operons include Sp_1027 in combination with at least one of fhs, piaA, proABC, spxB and Sp_1288. In an embodiment, the at least two genes or operons are piaA and proABC.

In an embodiment, the at least two genes or operons comprise spxB in combination with at least one gene or operon selected from fhs, piaA, proABC, Sp_1288 or Sp_1027. Live attenuated strains comprising disrupted spxB show reduced virulence yet are still able to colonise the nasopharynx.

In an embodiment, the at least two genes or operons comprise Sp_1288 in combination with at least one gene or operon selected from fhs, piaA, proABC, spxB or Sp_1027. Live attenuated strains comprising disrupted Sp_1288 show reduced virulence yet are still able to colonise the nasopharynx. Disruption of Sp_1288 is found to both reduce virulence and protect against pneumonia rechallenge.

In an embodiment, the at least two genes or operons comprise Sp_1027 in combination with at least one gene or operon selected from fhs, piaA, proABC, Sp_1288 or spxB. Live attenuated strains comprising disrupted Sp_1027 show reduced virulence yet are still able to colonise the nasopharynx.

In an example, the at least two genes or operons comprise piaA in combination with fhs. This combination of genes is found to strongly reduce virulence in both pneumonia and sepsis models. Prior colonization of a live attenuated strain with a piaA and fhs double mutant protected against rechallenge with wild type S. pneumoniae and recolonization models, indicating that the live attenuated strain provides good protective immunity.

In an example, the at least two genes or operons comprise piaA in combination with proABC. This combination of gene and operon is found to strongly reduce virulence in a pneumonia model and partly reduce virulence in a sepsis model. Prior colonization of a live attenuated strain with a piaA and proABC double mutant protected against rechallenge with wild type S. pneumoniae and recolonization models, indicating that the live attenuated strains provides good protective immunity. fhs described herein refers to the gene encoding the formate dehydrogenate ligase. fhs may otherwise be known as Formyltetrahydrofolate synthetase or Fhsts. The fhs gene corresponds to gene number Spn_01764 in the 6B BHN418 strain; SP_1229 in the TIGR4 strain and SPD_1087 in the D39 strain. The fhs gene encodes for a protein that has formate dehydrogenate ligase activity and is putatively involved with purine synthesis. In an embodiment, the fhs gene in a wild-type strain may have at least 70% nucleotide sequence identity, or at least 75%, or at least 80%, or at least 85%, or at least 90%, or at least 92.5%, or at least 95%, or at least 97.5%, or at least 99%, or 100% nucleotide sequence identity with SEQ ID 1.

piaA described herein refers to the gene encoding the membrane permease PiaA. piaA may otherwise be known as Pneumococcal Iron Acquisition A. The piaA gene encodes for a lipoprotein component of the dominant S. pneumoniae uptake ABC transporter which is a transmembrane permease protein associated with iron acquisition. The piaA gene may otherwise be known as SPR_082. The piaA gene corresponds to gene number Spn_01563 in the 6B BHN418 strain, SP_1032 in the TIGR4 strain and SPD_0915 in the D39 strain. In an embodiment, the piaA gene in a wildtype strain may have at least 70% nucleotide sequence identity, or at least 75%, or at least 80%, or at least 85%, or at least 90%, or at least 92.5%, or at least 95%, or at least 97.5%, or at least 99% or 100% nucleotide sequence identity with SEQ ID 2.

ProABC described herein refers to the genes within the L-proline synthesis operon which includes proB, proA and proC genes. The proABC genes encode for proteins involved in proline synthesis. The proABC operon and gene(s) corresponds to gene numbers Spn_01479-Spn_01481 in the 6B BHN418 strain (proB: Spn_01479; proA: Spn_01480 and proC: Spn-01481) SP_0931-SP_0933 in the TIGR4 strain (proB: SP_931; proA: SP_0932 and proC: SP_0933) and SPD_0822-0824 in the D39 strain (proB: SPD_0822; proA SPD_0823; and proC: SPD_0824). In an embodiment, the proABC operon in a wildtype strain may have at least 70% nucleotide sequence identity, or at least 75%, or at least 80%, or at least 85%, or at least 90%, or at least 92.5%, or at least 95%, or at least 97.5%, or at least 99%, or 100% nucleotide sequence identity with SEQ ID 3 (or SEQ ID 4 and SEQ ID 5 and SEQ ID 6). In an embodiment, the proB gene in the wildtype strain may have at least 70% nucleotide sequence identity, or at least 75%, or at least 80%, or at least 85%, or at least 90%, or at least 92.5%, or at least 95%, or at least 97.5%, or at least 99%, or 100% nucleotide sequence identity with SEQ ID 4. In an embodiment, the proA gene in the wildtype strain may have at least 70% nucleotide sequence identity, or at least 75%, or at least 80%, or at least 85%, or at least 90%, or at least 92.5%, or at least 95%, or at least 97.5%, or at least 99%, or 100% nucleotide sequence identity with SEQ ID 5. In an embodiment, the proC gene in the wildtype strain may have at least 70% nucleotide sequence identity, or at least 75%, or at least 80%, or at least 85%, or at least 90%, or at least 92.5%, or at least 95%, or at least 97.5%, or at least 99%, or 100% nucleotide sequence identity with SEQ ID 6. Each of proB, proA and proC encode for proteins involved in proline synthesis. Disruption of genes or impaired function of proteins encoded by the proABC operon as described herein may refer to disruption or impaired function of one or more of the proB, proA or proC genes or all of the proB, proA and proC genes.

spxB described herein refers to the gene encoding the pyruvate oxidase SpxB. SpxB may otherwise be known as pyruvic oxidase or POX. The spxB gene encodes for a protein that has pyruvate oxidase activity and is involved in the oxidative stress response. In some embodiments, the spxB gene encodes the protein that has the functions of pyruvate oxidase activity, magnesium ion binding and thiamine pyrophosphate binding. The spxB gene corresponds to gene number Spn_01272 in the 6B BHN418 strain; SP_0730 in the TIGR4 strain and SPD_0636 in the D39 strain. In an embodiment, the spxB gene in a wildtype strain may have at least 70% nucleotide sequence identity, or at least 75%, or at least 80%, or at least 85%, or at least 90%, or at least 92.5%, or at least 95%, or at least 97.5%, or at least 99% or 100% nucleotide sequence identity with SEQ ID 7.

The Sp_1288 gene refers to the gene encoding the UPF0122 protein. The function of Sp_1288 is putatively linked with the signal recognition pathway and encodes for a protein that may have a DNA-binding function. The Sp_1288 gene corresponds to gene number Spn_01821 in the 6B BHN418 strain; SP_1288 in the TIGR4 strain and SPD_1143 in the D39 strain and spr1167 in the R6 strain. In an embodiment, the Sp_1288 gene in a wildtype strain may have at least 70% nucleotide sequence identity, or at least 75%, or at least 80%, or at least 85%, or at least 90%, or at least 92.5%, or at least 95%, or at least 97.5%, or at least 99% or 100% nucleotide sequence identity with SEQ ID 8.

The Sp_1027 gene corresponds to gene number Spn_01560 in the 6B BHN418 strain, SP_1027 in the TIGR4 strain; SPD_0913 in the D39 strain and spr931 in the R6 strain. In an embodiment, the Sp_1027 gene in a wildtype strain may have at least 70% nucleotide sequence identity, or at least 75%, or at least 80%, or at least 85%, or at least 90%, or at least 92.5%, or at least 95%, or at least 97.5%, or at least 99% or 100% nucleotide sequence identity with SEQ ID 9.

In some embodiments, the at least two genes or operons consist of two genes or operons. In some embodiments, the at least two genes or operons may comprise two, three, four or more disrupted genes or operons that have disrupted expression or encode for a protein with impaired function, wherein the genes or operons are selected from fhs, piaA, proABC, spxB, Sp_1288, and Sp_1027. In some embodiments, the live attenuated strain may further comprise one or more genes or operons that has disrupted expression or encodes for a protein that has impaired function different to fhs, piaA, proABC, spxB, Sp_1288, and Sp_1027 In an embodiment, the live attenuated strain may further comprise deletion and/or mutation of a gene different to fhs, piaA, proABC, spxB, Sp_1288, and Sp_1027.

In an embodiment, the at least two genes or operons have disrupted expression. In an embodiment, the at least two genes or operons encode for a protein with impaired function. In an embodiment, one of the at least two genes has disrupted expression, and the other of the at least two genes encodes for a protein with impaired function.

According to the sixth aspect of the present invention, there is provided a live attenuated strain for use comprising at least one gene or operon that has disrupted expression or encodes for a protein with impaired function, the at least one gene or operon being selected from fhs, proABC, Sp_1288 or Sp_1027. The live attenuated strain for use has reduced virulence as compared to a wildtype strain and is able to successfully colonise the nasopharynx. In some embodiments, the live attenuated strain may comprise one or more further genes or operons with disrupted expression different to fhs, proABC, Sp_1288 or Sp_1027. In some embodiments, the live attenuated strain may further comprise one or more genes or operons that encodes for a protein with impaired function different to fhs, proABC, Sp_1288 or Sp_1027. In some embodiments, the live attenuated strain may further comprise one or more gene that has disrupted expression, wherein the one or more gene is selected from piaA, or spxB. In some embodiments, the live attenuated strain may further comprise one or more gene or operon that encodes for a protein with impaired function, wherein the one or more gene or operon is selected from piaA or spxB.

In an embodiment of the live attenuated strains and the live attenuated strains for use described herein, the live attenuated strain does not contain a disrupted piuA gene. In an embodiment, the live attenuated strain does not contain a piuA gene that encodes for a protein with impaired function. In an embodiment, the live attenuated strain comprises a wildtype piuA gene (i.e. a non mutated or non-deleted piuA gene). piuA described herein refers to the hydroxamate-type ferrisiderophore receptor, which may otherwise be known as Iron Transport Protein Piu. The piuA gene corresponds to gene number Spn_0139 in the 6B BHN418 strain and SP_1872 in the TIGR4 strain. Previous studies (not shown) suggest that disrupted piuA has a weaker effect on virulence showing only mild attenuation in a pulmonary infection model and limited attenuation in a systemic infection model. Disrupted piuA may have reduced ability to colonise the nasopharynx, e.g., as compared to piaA.

In an embodiment of the live attenuated strains and the live attenuated strains for use described herein, the live attenuated strain does not comprise a disrupted cps locus nor an impaired cps locus that encodes for one or more proteins with impaired function. In an embodiment, the live attenuated strain comprises a wildtype cps locus (i.e. a non-mutated or non-deleted cps locus). The cps locus described herein corresponds to gene number Spn_00899-913 in the 6B BHN418 strain and SP_0346-60 in the TIGR4 strain. In some examples, disrupted expression of the cps locus was found to affect the ability of the live attenuated strain to colonise the nasopharynx, and live attenuated strains with disrupted cps induced weaker immunity at the mucosal level with minimal effect on lung CFU after pneumonia rechallenge or nasal wash CFU after infection/rechallenge, making such strains less attractive for use in boosting immunity and/or preventing infection. Cps described herein refers to the capsule polysaccharide locus. In an embodiment, the cps locus is defined as any gene located between dexB and aliA genes.

In an embodiment of the live attenuated strains and the live attenuated strains for use described herein, the live attenuated strain does not comprise a disrupted psaA gene. In an embodiment, the live attenuated strain does not contain a psaA gene that encodes for a protein with impaired function. In an embodiment, the live attenuated strain comprises a wildtype psaA gene (i.e. a non-mutated or non-deleted psaA gene). psaA described herein refers to the Manganese ABC transporter substrate-binding lipoprotein. The psaA gene corresponds to gene number Spn_2120 in the 6B BHN418 strain and SP_1650 in the TIGR4 strain. In some examples, disrupted expression of the psaA gene was found effect the ability of the live attenuated strain to colonise the nasopharynx.

In an embodiment of the live attenuated strains and the live attenuated strains for use described herein, the live attenuated strain does not comprise a disrupted pspA gene. In an embodiment, the live attenuated strain does not contain a pspA gene that encodes for a protein with impaired function. In an embodiment, the live attenuated strain comprises a wildtype pspA gene (i.e. a non-mutated or non-deleted pspA gene). pspA described herein refers to the Surface protein pspA. The psaA gene corresponds to gene number Spn_2120 in the 6B BHN418 strain and SP_1650 in the TIGR4 strain.

Deletion and/or Mutation of Genes or Operons

In an embodiment of the first aspect, the at least two genes or operons may be deleted and/or mutated. In an embodiment of the sixth aspect, the at least one gene or operon may be deleted and/or mutated.

Deletion and/or mutation of genes or operons as referred to herein may be effected by any suitable method. Deletion and/or mutation of genes or operons as referred to herein may be the whole of the genes or operons or a portion thereof.

In an embodiment, the deletion and/or mutation of genes or operons may be a portion thereof. In some embodiments, the portion thereof may be a gene promoter or a transcriptional start site.

In an embodiment, the deletion is the whole of the gene or operon. In an embodiment, the gene or operon is completely replaced in frame by a gene deletion cassette. In some embodiments, the deletion by gene deletion cassette is performed using overlap extension PCR. In some embodiments, the gene deletion cassette is an antibiotic resistance cassette. In some embodiments, the antibiotic resistant cassette is a spectinomycin resistant or kanamycin resistance cassette. Live attenuated strains comprising an antibiotic resistant cassette demonstrate resistance towards antibiotics. In some embodiments, the gene deletion cassette is not an antibiotic resistance cassette.

In some embodiments, competence stimulating peptides are used to induce single- or double-cross over integration of a gene deletion plasmid or cassette. In alternative embodiments, the deletion is by cre/recombinase techniques, for example, Cre-Lox techniques. In alternative embodiments, the deletion is by Janus or a modified Janus cassette.

In alternative embodiments, the deletion and/or mutation of a gene or operon is obtained by point mutation or CRISPR/Cas9 techniques.

Genes Having Disrupted Expression

In an embodiment of the first aspect, the at least two genes or operons have disrupted expression Disrupted expression referred to herein refers to disrupted expression of any gene product as compared to a wild-type strain. Gene product described herein refers to any product of transcription or translation (e.g. gene transcripts (e.g.

mRNA), or encoded protein). Live attenuated strains comprising at least two genes or operons with disrupted expression can in some embodiments be used interchangeably with live attenuated strains comprising at least two genes or operons that are deleted and/or mutated.

In an embodiment, the expression of the at least two genes or operons is reduced by at least about 50% as compared to a wild-type strain, or by at least 55%, or by at least 60%, or by at least 65%, or by at least 70%, or by at least 75%, or by at least 80%, or by at least 85%, or by at least 87.5%, or by at least 90%, or by at least 91%, or by at least 92%, or by at least 93%, or by at least 94%, or by at least 95%, or by at least 96%, or by at least 97%, or by at least 98%, or by at least 99%, or by at least 99.5%, or by at least 99.9% as compared to the wild-type strain. In an embodiment, the expression of one of the at least two genes or operons is reduced by at least 50% as compared to a wild-type strain, or by at least 55%, or by at least 60%, or by at least 65%, or by at least 70%, or by at least 75%, or by at least 80%, or by at least 85%, or by at least 87.5%, or by at least 90%, or by at least 91%, or by at least 92%, or by at least 93%, or by at least 94%, or by at least 95%, or by at least 96%, or by at least 97%, or by at least 98%, or by at least 99%, or by at least 99.5%, or by at least 99.9% as compared to the wild-type strain; and the other of the at least two genes is reduced by at least at 50% as compared to a wild-type strain, or by at least 55%, or by at least 60%, or by at least 65%, or by at least 70%, or by at least 75%, or by at least 80%, or by at least 85%, or by at least 87.5%, or by at least 90%, or by at least 91%, or by at least 92%, or by at least 93%, or by at least 94%, or by at least 95%, or by at least 96%, or by at least 97%, or by at least 98%, or by at least 99%, or by at least 99.5%, or by at least 99.9% as compared to the wild-type strain. The wild-type strain refers to a live non-attenuated strain of the same serotype.

In an embodiment, disrupted expression of the least two genes or operons refers to the gene expression (e.g. mRNA expression) of the at least two genes or operons being reduced as compared to a wild-type strain.

In an embodiment, the reduction in expression is measured by comparing the number of gene transcripts for the at least two genes in the live attenuated strain as compared to the wild-type strain. This may otherwise be known as mRNA quantification. As defined herein "gene transcripts" refers to the mRNA produced by transcription of the gene. In an embodiment, the comparing is determined after culturing the live attenuated strain and the wildtype strain under the same growth conditions, e.g., in the same growth media. In an embodiment, the laboratory media is THY broth. In an embodiment, the live attenuated strain and wild type strains are both cultured in THY broth up to an $OD_{595}$ of 0.4 to 0.5.

In some embodiments, comparing the number of gene transcripts for the at least two genes is determined by any suitable technique. In an embodiment, the reduction in expression of the at least two genes is measured by RNA-seq. The RNA for sequencing may be extracted using any suitable technique. In some embodiments, the RNA is extracted using column purification, guanidinium thiocyanate-phenol-chloroform extraction (or similar) or any combination thereof. In some embodiments, the column purification involves a glass-fibre filter. In an embodiment, the RNA may be treated with DNAse prior to sequencing and/or ribosomal RNA may be removed from the sample prior to sequencing. In an embodiment, the RNA may be amplified by RT-PCR prior to sequencing, for example, for at least 4 cycles, or at least 6 cycles, or less than 15 cycles, or less than 12 cycles, or less than 10 cycles, or about 8 cycles.

RNA-seq may be performed using next-generation sequencing technology, for example, a NextSeq 500 desktop sequencer with a 75 cycle high-output kit. The sequencing data may be mapped and quantified with respect to the reference using any suitable algorithm, for example, the Salmon algorithm. The expression or reduction in expression may be determined using any suitable technique, for example, the rlog method using, for example, the DEseq2 package.

In an alternative embodiment, the expression or reduction of expression of the at least two genes is measured by reverse transcription PCR (e.g. quantitative reverse transcription-PCR).

In an alternative embodiment, disrupted expression of the at least two genes or operons may refer to the proteins encoded by the at least two genes or operons having reduced expression as compared to a wild-type strain. In an embodiment, the reduction in expression of the at least two genes or operons is determined by quantifying the level of translated protein encoded by the at least two genes or operons.

In an embodiment, the reduction in expression of translated protein encoded by the at least two genes or operons is determined by any suitable technique, for example, ELISA or western blotting. In an embodiment, the reduction in expression of translated protein encoded by the at least two genes or operons is determined after culturing the live attenuated strain and the wildtype strain under the same growth conditions, e.g., in the same growth media. In an embodiment, the laboratory media is THY broth. In an embodiment, the live attenuated strain and wild type strains are both cultured in THY broth up to an $OD_{595}$ of 0.4 to 0.5.

In an embodiment, the disrupted expression of the at least two genes or operons is caused by deletion and/or mutation of the at least two genes or operons or a portion thereof. In an embodiment, the disrupted expression of the at least two genes or operons is caused by a deletion of the at least two genes or operons or a portion thereof. In an embodiment, the disrupted expression of the at least two genes or operons is caused by a mutation of the at least two genes or operons or a portion thereof. The deletion or mutation of the at least two genes or operons may be via any suitable method including any method described herein. In an embodiment, the at least two genes or operons are deleted and/or mutated via the same method. In an alternative embodiment, the at least two genes or operons are deleted and/or mutated via a different method.
i In an alternative embodiment, the disrupted expression of the at least two genes or operons is caused by biochemical inhibition of expression or function the at least two genes or operons. The biochemical inhibition of expression or function may be via any suitable method. In an embodiment, the biochemical inhibition may be effected by treatment with chemical reagents. In an embodiment, the biochemical inhibition may be effected by treatment with nucleic acid reagents that have a sequence complementary to the at least two genes or a sequence that is complementary to mRNA transcripts thereof.

In an alternative embodiment, the disrupted expression of the at least two genes or operons is not caused by deletion and/or mutation in the genes or operons themselves. In some embodiments, the deletion or mutation may be made upstream of the at least two genes or operons or to the gene regulatory systems.

In an embodiment of the sixth aspect, the at least one gene or operon has disrupted expression. In an embodiment, the expression of the at least one gene or operon is reduced by at least about 50% as compared to a wild-type strain, or by at least 55%, or by at least 60%, or by at least 65%, or by at least 70%, or by at least 75%, or by at least 80%, or by at least 85%, or by at least 87.5%, or by at least 90%, or by at least 91%, or by at least 92%, or by at least 93%, or by at least 94%, or by at least 95%, or by at least 96%, or by at least 97%, or by at least 98%, or by at least 99%, or by at least 99.5%, or by at least 99.9% as compared to the wild-type strain. Disrupted expression may be measured in the same manner as described for the first aspect.

In an embodiment, the disrupted expression of the at least one gene or operon is caused by deletion and/or mutation of the at least one gene or operon or a portion thereof. The deletion or mutation of the at least one gene or operon may be via any suitable method including any method described herein.

In an alternative embodiment, disrupted expression of the at least one gene or operon is caused biochemical inhibition of expression or function of the at least one gene or operon. The biochemical inhibition of the at least one gene or operon may be as described for the biochemical inhibition of expression or function of the at least two genes or operons in the first aspect.

In an alternative embodiment, the disrupted expression of the at least one gene or operon is not caused by deletion and/or mutation in the gene or operon itself. In some embodiments, the deletion or mutation may instead be made upstream of the at least one gene or operon or to the gene regulatory systems.

In an embodiment of the first and the sixth aspect, the live attenuated strain or live attenuated strains for use described herein do not show increased expression of the pspA gene, ply gene or pspC gene as compared to a wild-type strain. The expression is the pspA gene, ply gene or pspC gene may be measured as outlined above. The pspA gene, ply gene or pspC gene are key virulence genes and hence a lack of upregulation indicates that the live attenuated strains are safe for use in subjects to boost immunity and prevent infection.
Genes Having Impaired Function In an embodiment of the first aspect, the at least two genes or operons may encode for a protein with impaired function. In an embodiment, the at least two genes or operons encode for a protein that is non-functional.

Proteins with impaired function refer to any protein with reduced protein activity as compared to a wild-type strain. Live attenuated strains comprising at least two genes or operons that encode for a protein with impaired function can in some embodiments be used interchangeably with live attenuated strains comprising at least two genes or operons that are deleted and/or mutated.

In an embodiment, impaired function may be determined by comparing protein activity of the live attenuated strain compared to the wildtype strain.

In an embodiment, the % protein activity of the proteins encoded by the at least two genes or operons is reduced by at least about 50% as compared to a wild-type strain, or by at least 55%, or by at least 60%, or by at least 65%, or by at least 70%, or by at least 75%, or by at least 80%, or by at least 85%, or by at least 87.5%, or by at least 90%, or by at least 91%, or by at least 92%, or by at least 93%, or by at least 94%, or by at least 95%, or by at least 96%, or by at least 97%, or by at least 98%, or by at least 99%, or by at least 99.5%, or by at least 99.9% as compared to the wild-type strain. In an embodiment, the % protein activity of one of the proteins encoded by the at least two genes or operons is reduced by at least about 50% as compared to a wild-type strain, or by at least 55%, or by at least 60%, or by at least 65%, or by at least 70%, or by at least 75%, or by at least 80%, or by at least 85%, or by at least 87.5%, or by at least 90%, or by at least 91%, or by at least 92%, or by at least 93%, or by at least 94%, or by at least 95%, or by at least 96%, or by at least 97%, or by at least 98%, or by at least 99%, or by at least 99.5%, or by at least 99.9% as compared to the wild-type strain; and the % protein activity of the other protein encoded by the at least two genes is reduced by at least at 50% as compared to a wild-type strain, or by at least 55%, or by at least 60%, or by at least 65%, or by at least 70%, or by at least 75%, or by at least 80%, or by at least 85%, or by at least 87.5%, or by at least 90%, or by at least 91%, or by at least 92%, or by at least 93%, or by at least 94%, or by at least 95%, or by at least 96%, or by at least 97%, or by at least 98%, or by at least 99%, or by at least 99.5%, or by at least 99.9% as compared to the wild-type strain. The wild-type strain refers to a live non-attenuated strain of the same serotype.

In an embodiment, % protein activity is determined by any suitable method, for example, by functional ELISA or cell proliferation assay.

In an embodiment, the impaired function of the protein encoded by the at least two genes or operons is caused by deletion and/or mutation of the at least two genes or operons a portion thereof. The deletion and/or mutation of the at least two genes or operon may be obtained by any suitable method, including any method as described herein.

In an embodiment of the sixth aspect, the at least one gene or operon encodes for a protein with impaired function. In an embodiment, the at least one genes or operon encodes for a protein that is non-functional. In an embodiment, the protein activity of proteins encoded by the at least one gene or operon is reduced by at least about 50% as compared to a wild-type strain, or by at least 55%, or by at least 60%, or by at least 65%, or by at least 70%, or by at least 75%, or by at least 80%, or by at least 85%, or by at least 87.5%, or by at least 90%, or by at least 91%, or by at least 92%, or by at least 93%, or by at least 94%, or by at least 95%, or by at least 96%, or by at least 97%, or by at least 98%, or by at least 99%, or by at least 99.5%, or by at least 99.9% as compared to the wild-type strain. In an embodiment, the impaired function of the protein encoded by the at least one genes or operon is caused by deletion and/or mutation of the at least one gene or operon or a portion thereof. The deletion and/or mutation of the at least one gene or operon may be obtained by any suitable method, including any method as described herein Genome Sequence The live attenuated strain, or the live attenuated strain for use, as described herein may have a genome that lacks one or more of, or lacks a functional one or more of, a gene or operon selected from fhs, piaA, proABC, spxB, Sp_1288, Sp_1027 or a combination thereof. The live attenuated strain, or the live attenuated strain for use, as described herein may have a genome that lacks two or more of, or lacks a functional two or more of, genes selected from fhs, piaA, proABC, spxB, Sp_1288 and Sp_1027 or a combination thereof. In an example, the genome of the live attenuated strain lacks the piaA and the fhs genes. In an example, the genome of the live attenuated strain lacks the piaA gene and the proABC operon. In an example, the genome of the live attenuated strain lacks the fhs gene and the Sp_1288 gene.

The live attenuated strain, or the live attenuated strain for use, as described herein may have a genome that lacks one or more sequences selected from SEQ ID 1, SEQ ID 2, SEQ ID 3, SEQ ID 4, SEQ ID 5, SEQ ID 6, SEQ ID 7, SEQ ID 8, SEQ ID 9 or a combination thereof. The live attenuated strain, or the live attenuated strain for use, as described herein may have a genome that lacks one or more sequences with at least 70% DNA sequence identity, or at least 72.5%, or at least 75%, or at least 80%, or at least 85%, or at least 87.5%, or at least 90%, or at least 92.5%, or at least 95%, or at least 97.5%, or at least 99%, or at least 99.5%, or 100% sequence identity with SEQ ID 1, SEQ ID 2, SEQ ID 3, SEQ ID 4, SEQ ID 5, SEQ ID 6, SEQ ID 7, SEQ ID 8 or SEQ ID 9, or a combination thereof.

The live attenuated strain, or the live attenuated strain for use, as described herein may have a genome that lacks two or more sequences selected from SEQ ID 1, SEQ ID 2, SEQ ID 3, SEQ ID 4, SEQ ID 5, SEQ ID 6, SEQ ID 7, SEQ ID 8, SEQ ID 9 or a combination thereof. The live attenuated strain, or the live attenuated strain for use, as described herein may have a genome that lacks two or more sequences with at least or at least 72.5%, or at least 75%, or at least 80%, or at least 85%, or at least 87.5%, or at least 90%, or at least 92.5%, or at least 95%, or at least 97.5%, or at least 99%, or at least 99.5%, or 100% sequence identity with SEQ ID 1, SEQ ID 2, SEQ ID 3, SEQ ID 4, SEQ ID 5, SEQ ID 6, SEQ ID 7, SEQ ID 8, SEQ ID 9, or a combination thereof.

The genome (i.e. genome sequence) may be determined by any suitable method, for example, whole genome sequencing.

Methods of Making

Herein is also disclosed, is a method of making the live attenuated strain of S. pneumoniae of the first aspect, the method comprising providing a wild-type strain of Streptococcus pneumoniae, and deleting and/or mutating at least two genes or operons, wherein the at least two genes or operons are selected from fhs, piaA, proABC, spxB, Sp_1288, and Sp_1027.

Herein is also disclosed, is a method of making the live attenuated strain of S. pneumoniae used in the sixth aspect, the method comprising providing a wild-type strain of S. pneumoniae, and deleting and/or mutating at least one gene or operon, wherein the at least one gene or operon is selected from fhs, proABC, Sp_1288, and Sp_1027.

The genes or operons (i.e. the at least one gene or operon, or the at least two genes or operons) are deleted and/or mutated using any suitable method. In an embodiment, the at least two genes or operons or the at least one gene or operon is deleted and/or mutated by mutagenesis, for example, by overlap extension PCR.

In an embodiment, piaA is deleted or mutated. In an embodiment, the piaA gene is deleted using overlap extension PCR. In an embodiment, the piaA gene is deleted using overlap extension PCR using primers. In an example, the primers comprise one or more of, or all of, SeqID 16, SeqID 17, SeqID 18, SeqID 19, SeqID 20 or SeqID 21.

In an embodiment spxB is deleted or mutated. In an embodiment, the spxB gene is deleted using overlap extension PCR. In an embodiment, the spxB gene is deleted using overlap extension PCR using primers. In an example, the primers comprise one or more of, or all of, Seq-ID 46, SeqID 47, SeqID 48, SeqID 49, SeqID 50 or SeqID 51.

In an embodiment, fhs is deleted or mutated. In an embodiment, the fhs gene is deleted using overlap extension PCR. In an embodiment, the fhs gene is deleted using overlap extension PCR using primers. In an example, the primers comprise one or more of, or all of SeqID 52, SeqID 53, SeqID 54, Seq ID 55, Seq ID 56 or Seq ID 57.

In an embodiment, proABC is deleted or mutated. In an embodiment, the proABC operon is deleted using overlap extension PCR. In an embodiment, the proABC gene is deleted using overlap extension PCR using primers. In an example, the primers comprise one or more of, or all of, SeqID 34, SeqID 35, SeqID 36, SeqID 37, SeqID 38 or SeqID 39.

In an embodiment, Sp_1288 is deleted or mutated. In an embodiment, the Sp_1288 gene is deleted using overlap extension PCR. In an embodiment, the spr1167 gene is deleted using overlap extension PCR using primers. In an example, the primers comprise one or more of, or all of, SeqID 40, SeqID 41, SeqID 42, SeqID 43, SeqID 44 or SeqID 45.

In an embodiment, Sp_1027 is deleted or mutated. In an embodiment, the Sp_1027 gene is deleted using overlap extension PCR. In an embodiment, the spr931 gene is deleted using overlap extension PCR using primers. In an example, the primers comprise at least one of SeqID 88, SeqID 89, SeqID 90, SeqID 91, SeqID 92 or SeqID 93.

Pharmaceutical Composition

In accordance with a second aspect of the invention, there is provided a pharmaceutical composition comprising at least one live attenuated strain of *Streptococcus pneumoniae* according to the first aspect. In an embodiment, the live attenuated strain is of the same serotype as a *S. pneumoniae* strain that causes infection. In an embodiment, the live attenuated strain is selected such that it is a different serotype to a *S. pneumoniae* strain that causes infection. In some embodiments, the live attenuated strain is of a vaccine or a non-vaccine serotype.

In accordance with a third aspect of the invention, there is provided a pharmaceutical composition comprising two or more different live attenuated strains of *Streptococcus pneumoniae* according to the first aspect, wherein the two or more different live attenuated strains are of a different serotype. In some embodiments, the pharmaceutical composition comprises three or more, four or more, five or more, six or more, seven or more, eight or more, nine or more, or ten or more different live attenuated strains, wherein the strains are of a different serotype. In an embodiment, the live attenuated strain is of the same or different serotype to a strain that causes *S. pneumoniae* infection.

In an embodiment of the sixth aspect of the invention, the live attenuated strain for use is formulated as a pharmaceutical composition, as may be described herein.

In some embodiments, the two or more different live attenuated strains comprise the same at least two genes or operons that have disrupted expression or encode for a protein with impaired function. For example, in an embodiment, the at least two genes or operons are fhs and piaA in all of the two or more live attenuated strains. In another embodiment, the at least two genes or operons are proABC and piaA in all of the two or more live attenuated strains. In another embodiment, the at least two genes or operons are fhs and Sp_1288 in all of the two or more live attenuated strains In another embodiment, one or more of the two live attenuated strains comprises at least two genes or operons that have disrupted expression or encode for a protein with impaired function that is different from another of the two or more live attenuated strains. For example, the at least two genes or operons may be proABC and piaA in one or more live attenuated strains, and the at least two genes or operons may be fhs and piaA in another of the two or more live attenuated strains.

In some embodiments of the second and third aspects, the pharmaceutical composition may otherwise be referred to, or have the same purpose, as a vaccine, booster-dose vaccine or immune-boosting composition. As used herein, vaccine refers to a composition that provides exposure to an immunizing antigen leading to active acquired immunity to that antigen in a subject. Booster vaccine or immune-boosting composition refers to a composition that provides re-exposure to an immunizing antigen after initial immunization leading to boosted immunity after re-exposure to that antigen in a subject.

In some embodiments, the pharmaceutical composition further comprises at least one of a pharmaceutically acceptable adjuvant, excipient, diluent or carrier.

The adjuvant, excipient, diluent or carrier may be any suitable additive. In an embodiment, the adjuvant may be selected from alum (aluminium salts, e.g., aluminium phosphate, aluminium hydroxide or aluminium hydroxyphosphate sulfate), monophosphoryl lipid A, an oil in water emulsion (e.g. squalene oil), or a liposome. The adjuvant may enhance an immune response in a subject when administered.

The excipient may be selected from stabilizers, disintegrants, salts, pH modifiers, buffers, emulsifiers, lubricants, flavorants, aldehydes or combinations thereof. In an embodiment, the excipient may be selected from gelatin, sorbitol, lactose, mannitol, glycerol, urea, sucrose, mannose, fructose, dextrose, human or bovine serum albumin, phosphate salts (e.g. magnesium phosphate), sulfate salts (e.g. magnesium sulfate), microcrystalline cellulose, stearic acid or salts thereof (e.g. magnesium stearate), citric acid or salts thereof, glutamatic acid or salts thereof, salts (e.g. sodium chloride or magnesium chloride), carbonates (e.g. magnesium carbonate), bicarbonates, amino acids (e.g. asparagine and arginine), polysorbate, trometamol or combinations thereof. The excipient may be used to stabilize and/or improve the storage and/or improve the taste of the pharmaceutical composition.

In some embodiments, the pharmaceutical composition is formulated as a spray, optionally a nasal spray. The pharmaceutical composition is easy to use and can be easily administered in a non-invasive manner.

Live Attenuated Strains and Pharmaceutical Compositions for Use

According to the fourth aspect, there is provided the live attenuated strain according to the first aspect and the pharmaceutical composition according to the second or third aspect for use in preventing infection and/or enhancing immunity in a subject.

Also disclosed herein, is a live attenuated strain of *S. pneumoniae* for use in preventing infection and/or enhancing immunity in a subject, the live attenuated strain comprising at least one gene or operon that has disrupted expression or encodes for a protein with impaired function, and wherein the at least one gene or operon is selected from fhs, proABC, Sp_1288 or Sp_1027.

In embodiments of the live attenuated strains or pharmaceutical compositions described herein, the live attenuated strains or pharmaceutical compositions may be used to prevent a bacterial infection. In some embodiments, the bacterial infection may be caused by a gram-negative or a gram-positive bacteria. In some embodiments, the bacterial infection may be caused by any bacteria that colonizes the nasal mucosa. In an embodiment, the bacterial infection may be caused by any bacteria that colonizes the lungs, mouth, throat, or upper respiratory tract. The live attenuated strains and pharmaceutical compositions for use as described herein may therefore be used to boost innate immunity.

In an embodiment, the bacterial infection may be selected of genus *Streptococcus*. In an embodiment, the bacterial infection may be caused by *Streptococcus* group A, *Strep-*

*tococcus* group B, or a combination thereof. In an embodiment, the bacterial infection may be caused by *S. pyogenes, S. dysgalactiae, S. agalactiae,* S. pnemoniae, S. gallolyticus, *S. sanguinis, S. suis, S. mitis. S. mutans* or a combination thereof. In an embodiment, the bacterial infection may be caused by *S. pyogenes, S. agalactiae, S. pneumoniae* or, *S. suis* or a combination thereof. In some embodiments, the live attenuated strains or pharmaceutical compositions described herein may prevent bacterial infection in the lungs, mouth, throat or upper respiratory tract for at least 1 week, at least 1 month, at least 6 months, after administration.

In an embodiment, the live attenuated strain for use, or the pharmaceutical composition for use, prevents nasopharyngeal colonization of *S. pneumoniae.* In an embodiment the *S. pneumoniae* is of homologous serotype to the serotype of the live attenuated strain. In an alternative embodiment, the *S. pneumoniae* is of heterologous serotype to the serotype of the live attenuated strain.

Nasopharyngeal colonization by *S. pneumoniae* refers to the asymptomatic presence as detected by culture or by recovery of *S. pneumoniae* DNA in the nasopharynx. In some embodiments, the live attenuated strain or pharmaceutical compositions described herein prevent(s) nasopharyngeal colonisation by *S. pneumoniae* for at least 1 week, at least 1 month, at least 6 months, at least 1 year, or at least 5 years after administration.

According to the fifth aspect, there is provided the live attenuated strain according to the first aspect and the pharmaceutical composition according to the second or third aspect, for use in a method of preventing
   i) a *Streptococcus pneumoniae* infection,
   ii) pneumonia connected with *S. pneumoniae*
   iii) septicemia connected with *S. pneumoniae,*
   iv) meningitis connected with *S. pneumoniae*
   v) an exacerbation of chronic obstructive pulmonary disease (COPD) connected with *S. pneumoniae*
   vi) acute bronchitis connected with *S. pneumoniae*
   vii) acute sinusitis connected with *S. pneumoniae* or
   viii) acute otitis media connected with *S. pneumoniae* in a subject.

The *S. pneumoniae* infection is an infection caused by or connected with *S. pneumoniae.* In some embodiments, the infection is invasive or non-invasive. In some embodiments, the infection is an infection of the blood causing bacteraemia. In some embodiments, the live attenuated strain or pharmaceutical compositions described herein may prevent *S. pneumoniae* infection for at least 1 month, at least 6 months, at least 1 year, at least 2 years, at least 5 years after administration.

Pneumonia connected with *S. pneumoniae* is a lung infection that is otherwise known as pneumococcal pneumonia. Symptoms may include a fever, chills, a cough, shortness of breath, rapid breathing, chest pain, with secondary symptoms including nausea, vomiting, headache, fatigue, and muscle aches. In some embodiments, the live attenuated strain or pharmaceutical compositions described herein prevents pneumonia connected with *S. pneumoniae* for at least 1 week, at least 1 month, at least 6 months, at least 1 year, at least 5 years after administration.

Septicemia connected with *S. pneumoniae* is otherwise known as pneumococcal septicaemia. Septicaemia is otherwise known as sepsis. Symptoms may include confusion and/or disorientation, shortness of breath, high heart rate, fever, chills, extreme pain and/or discomfort and clammy or sweaty skin, tissue damage, organ failure and death. In some embodiments, the live attenuated strain or pharmaceutical compositions described herein prevents septicemia connected with *S. pneumoniae* for at least 1 week, at least 1 month, at least 6 months, at least 1 year, at least 5 years after administration.

Meningitis connected with *S. pneumoniae* is an infection of the brain and spinal cord otherwise known as Pneumococcal meningitis. Symptoms may include stiff neck, fever, headache, photophobia and confusion. In some embodiments, the live attenuated strain or pharmaceutical compositions described herein prevents meningitis connected with with *S. pneumoniae* for at least 1 week, at least 1 month, at least 6 months, at least 1 year, at least 5 years after administration.

Exacerbation of chronic obstructive pulmonary disease (COPD) connected with *S. pneumoniae* refers to when COPD symptoms get worse or flare up due to a *S. pneumoniae* infection. COPD is a type of obstructive lung disease characterized by long-term breathing problems and poor airflow. Symptoms of exacerbated COPD may include increased coughing, increased wheezing, increased shortness of breath, changes in colour, thickness and/or amount of mucus, tiredness, swelling of legs and/or ankles, trouble sleeping, and reduced oxygen level. In some embodiments, the live attenuated strain or pharmaceutical compositions described herein prevent(s) exacerbation of chronic obstructive pulmonary disease (COPD) connected with *S. pneumoniae* for at least 1 week, at least 1 month, at least 6 months, at least 1 year, at least 5 years after administration.

Acute bronchitis connected with *S. pneumoniae* refers to an infection and inflammation of the bronchi caused by *S. pneumoniae* infection. Symptoms may include coughing and the production of mucus. In some embodiments, the live attenuated strain or pharmaceutical compositions described herein prevent(s) acute bronchitis connected with *S. pneumoniae* for at least 1 week, at least 1 month, at least 6 months, at least 1 year, at least 5 years after administration.

Acute sinusitis connected with *S. pneumoniae* refers to inflammation of the sinuses caused by *S. pneumoniae* infection. Symptoms may include nasal congestion, sore throat, headache and pain or pressure in the sinus region. In some embodiments, the live attenuated strain or pharmaceutical compositions described herein prevent(s) acute sinusitis connected with *S. pneumoniae* for at least 1 week, at least 1 month, at least 6 months, at least 1 year, at least 5 years after administration.

Acute otitis media connected with *S. pneumoniae* refers to inflammation of the middle ear caused by *S. pneumoniae* infection. Symptoms may include fluid in the middle ear, swelling of the eardrum, and earache. In some embodiments, the live attenuated strain or pharmaceutical compositions described herein prevent(s) acute otitis media connected with *S. pneumoniae* for at least 1 week, at least 1 month, at least 6 months, at least 1 year, at least 5 years after administration.

In an embodiment of the live attenuated strain or the pharmaceutical composition according to the fifth aspect, or the live attenuated strain for the use according to the sixth aspect, the *S. pneumoniae* infection is of homologous serotype to the serotype of the live attenuated strain. For example, if the *S. pneumoniae* infection is caused by serotype 6B, the live attenuated strain or the pharmaceutical composition is of or comprises a live attenuated strain of serotype 6B.

In an alternative embodiment, the live attenuated strain or the pharmaceutical composition for the use according to the fifth aspect, or the live attenuated strain for the use according to the sixth aspect, the *S. pneumoniae* infection is of heterologous serotype to the serotype of the live attenuated strain. For example, if the *S. pneumoniae* infection is caused by serotype 6B, the live attenuated strain or the pharmaceutical composition is of or comprises a live attenuated strain different to serotype 6B.

In an embodiment of the live attenuated strain or the pharmaceutical composition for the use according to the fourth or fifth aspects, or the live attenuated strain for use according to the sixth aspect, the method comprises administering the live attenuated strain or the pharmaceutical composition to the upper airway of the subject. This may ensure that the live attenuated strain can effectively colonise the nasopharynx. In an embodiment of the live attenuated strain or the pharmaceutical composition for the use according to the fourth or fifth aspects, or the live attenuated strain for use according to the sixth aspect the method comprises administering the live attenuated strain or the pharmaceutical composition using any suitable method. In an embodiment, the method comprises administering the live attenuated strain or the pharmaceutical composition intranasally, nasopharyngeally, to the oropharynx, subcutaneously, intradermally, intramuscularly, or a combination thereof. In a preferred embodiment, the method of administration is nasopharyngeally.

In an embodiment of the live attenuated strain or the pharmaceutical composition for the use according to the fourth or fifth aspects, or the live attenuated strain for use according to the sixth aspect, the method comprises administering the live attenuated strain or the pharmaceutical composition to a subject every 5 years, or every 2 years, or every year, or every 6 months in a subject. In an embodiment, the method comprises administering the live attenuated strain or the pharmaceutical composition in a single dose, or a multiple dose. In an embodiment, the multiple dose comprises two, three, or four or more doses. In an embodiment, the multiple doses are administered at different time-points. In an embodiment, the multiple doses are administered at least 1 month apart, or at least 3 months apart, or at least 6 months apart.

In an embodiment of the live attenuated strain or the pharmaceutical composition for the use according to the fourth or fifth aspects, or the live attenuated strain for use according to the sixth aspect, the subject is a mammal subject. In a preferred embodiment, the subject is human. The human subject is any suitable age, for example, an infant (less than 1 year of age) a child (younger than 18 years of age) including adolescents (10 to 18 years of age inclusive), or adults (older than 18 years of age) including elderly subjects (older than 65 years of age). In some embodiments, the human subject is an elderly subject. In some embodiments, the human subject has a lung, heart, renal, liver or neurological morbidity.

Examples

The following illustrates examples of the live attenuated strain of the present invention and other aspects described herein. Thus, these examples should not be considered as limitations of the present disclosure, but are merely in place to each how to make examples of the present disclosure. While the live attenuated strains, and related aspects have been described with reference to certain examples, various modifications, changes, omissions, and substitutions can be made without departing from the spirit and scope of the present disclosure. It is intended, therefore, that the live attenuated strain and related aspects only be limited only by the scope of the following claims and their equivalents. It should be noted that the above-mentioned examples illustrate rather than limit what is described herein, and that those skilled in the art will be able to design many alternative implementations without departing from the scope of the appended claims.

Single Mutant Strains

Fourteen genes or operons were screened for initial investigation: the capsule locus, pspA, psaA, piaA, adcA, spxB, glnPQ, aliA, malX, fhs, proABC, Sp_1027, Sp_1288 and spr1759. Deletion mutant strains of each target gene were made in the 6B BHN418 capsular serotype 6B *S. pneumoniae* background. Their phenotype was assessed in mouse models of pneumonia (see Table 1).

TABLE 1

Data are $\log_{10}$ CFU/ml recovered from target organs in a mouse model of pneumonia 28 hours after infection, with n = 5 or 6 mice per group and standard deviations given in parentheses. Results in bold are statistically significantly different to the wild type 6B strain data (Kruskall-Wallis test to identify significant differences between groups, p < 0.05).

| Strain | Gene function | CFU ml$^{-1}$ Blood | CFU ml$^{-1}$ Lungs |
|---|---|---|---|
| | | Experiment 1 | |
| 6B | — | 3.79(1.18) | 3.65(0.63) |
| ΔpspA | Complement inhibition | 1.90 (1.91) | 3.75 (0.49) |
| ΔpiaA | Iron uptake | 2.28 (1.03) | 3.65 (0.65) |
| ΔadcA | Zinc uptake | 1.79 (2.45) | 3.66 (0.92) |
| ΔpsaA | Manganese uptake | 0 (0) | 3.72 (0.95) |
| | | Experiment 2 | |
| 6B | — | 4.64(1.13) | 4.73(0.51) |
| ΔproABC | Proline synthesis | 1(1.68) | 3.33(1.27) |
| ΔSp_1288 | Unknown | 2.34(2.28) | 3.62(0.54) |
| ΔspxB | Oxidative stress response | 1.84(2.2) | 3.84(1.24) |
| Δfhs | Formate tetrahydrofolate ligase | 0 (0) | 3.25(1.36) |
| ΔSp_1027 | Unknown | 2.38 (2.26) | 4.72 (1.08) |
| | | Experiment 3 | |
| 6B | — | 2.49(0.94) | 4.72(0.37) |
| Δcps | Capsule synthesis | 0(0) | 3.52(0.91) |
| | | Experiment 4 | |
| 6B | — | 2.73(0.74) | 3.65(1.19) |
| ΔmalX | Maltose uptake | 2.75(1.21) | 4.49(0.75) |
| ΔaliA | Oligopeptide uptake | 3.05(1.96) | 3.88(1.11) |
| ΔglnPQ | Glutamine/glutamate metabolism | 1.81(1.69) | 3.46(1.8) |
| Δspr1759 | Transcriptional regulator | 1.26 (1.16) | 4.36(1.01) |

A number of mutant strains were significantly attenuated in virulence in a pneumonia model, including mutations affecting the genes Δfhs, ΔproABC, ΔSp_1288 and ΔSp_1027. Δfhs, ΔproABC, ΔpsaA and Δcps mutant strains showed particularly marked reductions in blood CFU, compared to the wild type. No single mutant showed statistically significant differences in lung CFU compared to wild type 6B.

However, only some mutant strains attenuated in virulence were able to colonise the nasopharynx to a similar density as the wild type strain, the exceptions being ΔpsaA and Δcps (see Table 2). An ability to colonise the nasopharynx is considered key for a live attenuated strain to be able to be used as a vaccine to establish protective immunity.

Prior colonisation with either the 6B wild type and a number of the mutant strains completely prevented bacteraemia after 6B strain pneumonia challenge 30 days post-colonisation, and for some mutant strains (e.g. piaA, fhs, Sp_1288) also reduced lung or BALF CFU (Table 2).

From this screen, multiple gene mutations were therefore identified which reduced *S. pneumoniae* virulence but importantly still preserved induction of protection against reinfection after colonisation.

TABLE 2

Nasopharyngeal colonisation and protective ability of single gene *S. pneumoniae* mutant strains at 7 days post inoculation. Colonisation was assessed from the $\log_{10}$ CFU/ml recovered from nasal washes after 7 days (n = 20 mice wild type groups, 5 to 6 for mutant strains). Protection was assessed using $\log_{10}$ CFU/ml recovered from target organs in a mouse model of pneumonia 28 hours after infection. Results in bold are statistically significantly different to the wild type 6B strain data (Kruskall-Wallis test to identify significant differences between groups, p < 0.05).

| | COLONISATION | RECHALLENGE WITH 6B | | |
|---|---|---|---|---|
| Mutant | $\text{CFU ml}^{-1}$ Nasal wash | $\text{CFU ml}^{-1}$ Blood | $\text{CFU ml}^{-1}$ Lung | $\text{CFU ml}^{-1}$ BALF |
| PBS control | n/a | 3.08(1.95) | 5.29(0.97) | 3.42(1.01) |
| 6B | 3.57(0.44) | 0(0) | 4.15(1.24) | 1.88(0.95) |
| ΔpspA | 3.83(0.48) | 0(0) | 4.59(0.19) | 1(0) |
| ΔpiaA | 4.08(0.65) | 0(0) | 2.93(2.69) | 1.25(1.71) |
| ΔadcA | 3.49(1.43) | 0(0) | 5.15(0.62) | 2.68(1.92) |
| ΔpsaA | 1.97(0.83) | 0(0) | 5.10(0.45) | 2.29(2.18) |
| ΔproABC | 3.62(0.36) | 0(0) | 4.50(0.91) | 2.59(1.64) |
| ΔSp_1288 | 3.97(0.82) | 0(0) | 3.40(0.49) | 1.20(1.10) |
| ΔspxB | 3.67(0.20) | 0(0) | 4.18(0.60) | 1.62(1.55) |
| Δfhs | 3.60(0.46) | 0(0) | 3.58(0.54) | 1.77(1.67) |
| Δcps | 1.31(0.93) | 0.91(2.0) | 5.19(1.33) | 2.43(2.26) |

Double Mutants

To minimise the chance of revertants leading to recovery of virulence when used in human studies, double mutant strains were made using virulence genes selected from the single mutant screening. Two example live attenuated double mutant encapsulated (Δfhs/piaA and ΔproABC/piaA) strains were created, along with two comparative double mutant unencapsulated strains (Δcps/psaA and Δcps/proABC). All mutations were stable during growth without antibiotic selective pressure (data not shown). Whole genome sequencing identified a limited number of new SNPs in the double mutant strains but no unexpected insertions or deletions compared to the parental wild type strain (see Annex Table 1).

FIG. 1 shows the phenotype of example live attenuated double mutant strains in murine pneumonia, sepsis and colonisation models as compared to a wildtype strain. (A) and (B) shows pneumonia model; CFU obtained from blood (A) and lung (B) of CD1 mice 28 hours post intranasal inoculation with 1×10' CFU of wild type 6B or example live attenuated *S. pneumoniae* double mutant strains. (C) is a sepsis model; CFU in blood of CD1 mice 24 hours post intraperitoneal inoculation with $5×10^6$ CFU of wild type 6B or example live attenuated *S. pneumoniae* strains. (D) Colonisation model; CFU in nasal washes of CD1 mice 7 days post colonisation with $1×10^7$ CFU of wild type 6B or example live attenuated *S. pneumoniae* double mutant strains. Each symbol represents data from a single mouse, horizontal bars represent median values, error bars represent interquartile range and asterisks represent statistical significance compared to the wild type strain (Kruskall-Wallis with Dunn's post hoc test to identify significant differences between groups, *, p<0.05; *, p<0.01; *, p<0.001).

Figure 1A:
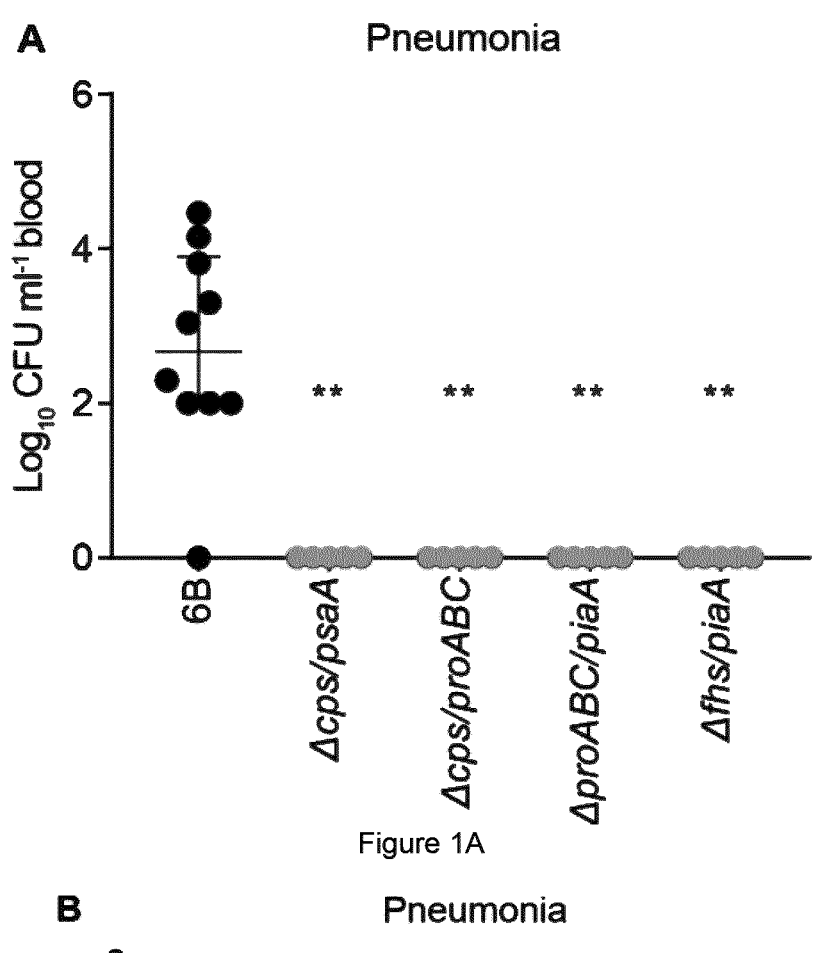
FIG. 1 shows the virulence phenotype in comparison to the wild type *S. pneumoniae* strain of example ΔproABC/piaA or Δfhs/piaA live attenuated *S. pneumoniae* strains in murine pneumonia, sepsis, and colonisation models.
Figure 1B:
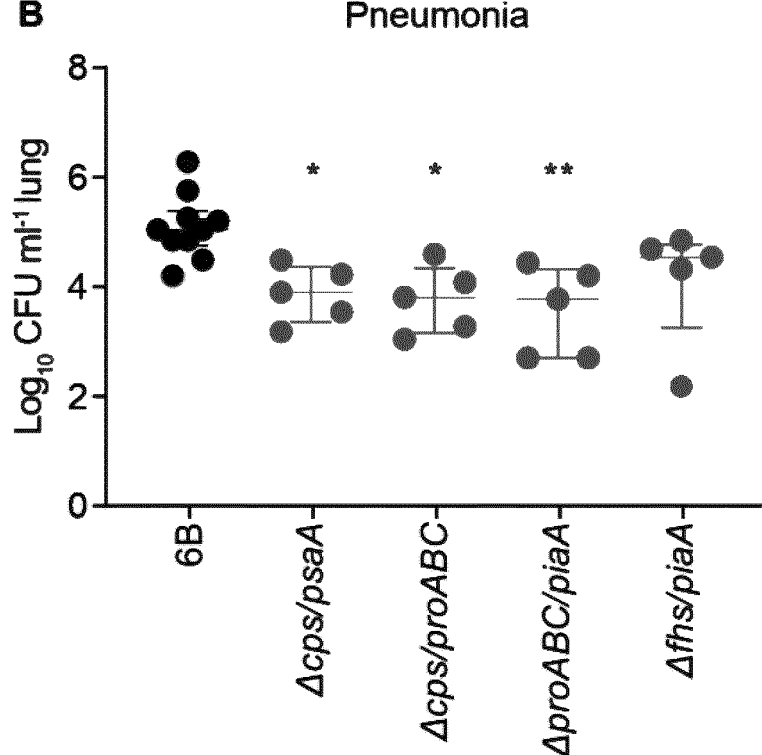
Figure 1C:
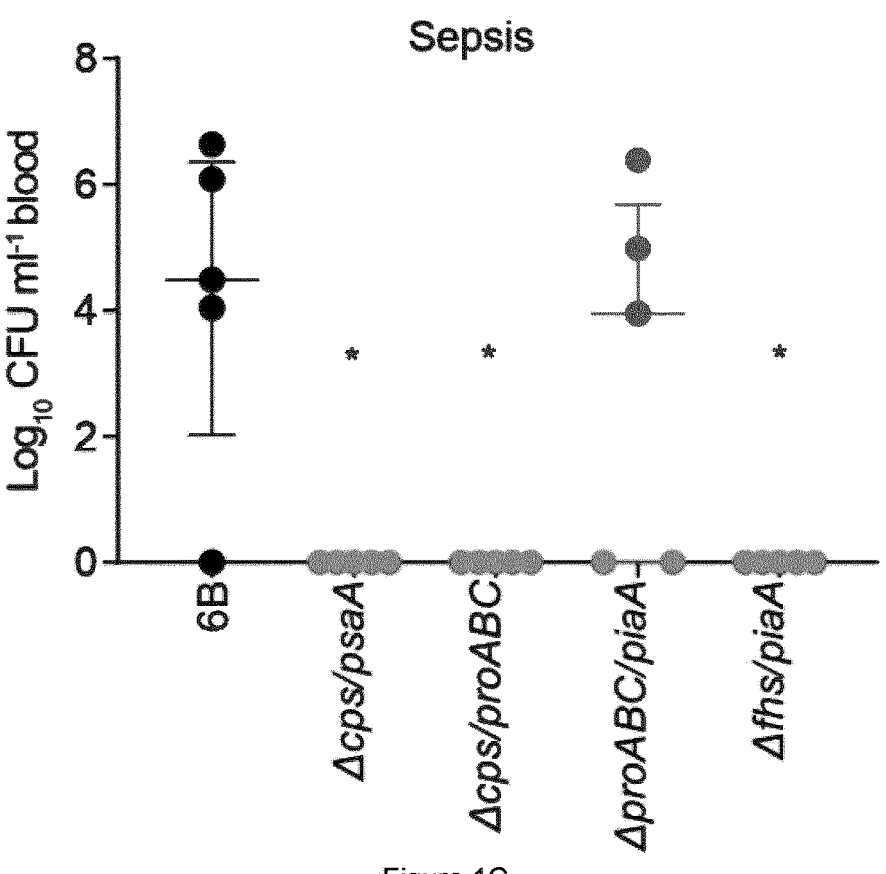
Figure 1D:
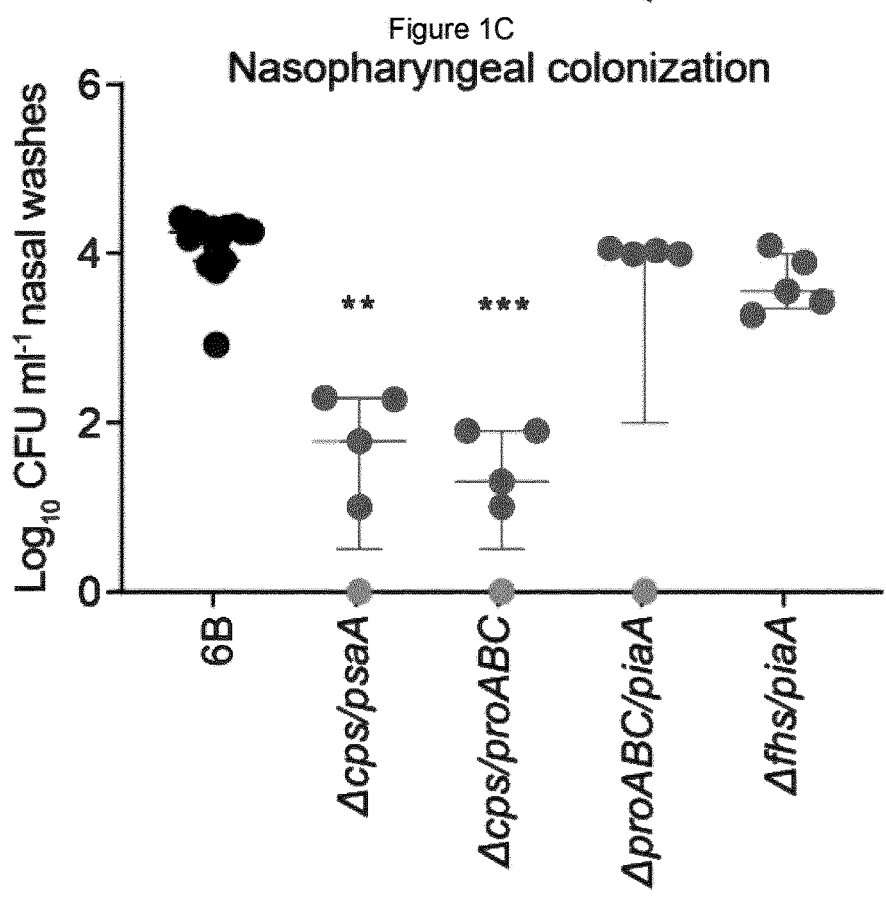

The double mutant strains Δfhs/piaA and ΔproABC/piaA were strongly reduced in virulence in mouse models of both pneumonia and sepsis, with significant reductions in lung CFU (pneumonia model) (FIG. 1B) and marked reductions in CFU recovered from blood (both pneumonia and sepsis model) compared to the parent 6B (FIG. 1A, 1C). In the colonisation model, nasal wash CFU for the ΔproABC/piaA and Δfhs/piaA strains were similar to mice infected with the wild type 6B, whereas >2 $\log_{10}$ lower CFU were recovered from mice infected with Δcps/psaA or Δcps/proABC (FIG. 1D). These results confirmed all four double mutant strains were highly attenuated in virulence. While Δfhs/piaA and ΔproABC/piaA were able to successfully colonise the nasopharynx, the unencapsulated double mutant strains were impaired in colonising ability, which is believed to reduce adaptive immune responses to colonisation.

RNAseq identified significant up- and down-regulation of multiple genes in the double mutant strains, but importantly did not show increased expression of key virulence genes (eg pneumolysin, pspA, or pspC) that might affect their safe use in humans (see Annex Table 2)

Immunological Response to Colonisation with Double Mutant Strains

FIG. 2 shows the serological responses to colonisation with the wild type 6B or example live attenuated *S. pneumoniae* strains Δfhs/piaA and ΔproABC/piaA. (A) and (B) Whole-cell ELISAs for IgG responses to the 6B (A) or capsular serotype 4 TIGR4 and capsular serotype 2 D39 (B) strains in mouse sera 28 days post colonisation with the corresponding strain, wild type or example live attenuated strains compared with uncolonised controls. (C) Whole-cell ELISA IgG responses to 6B (white) or Δcsp 6B mutant (grey) strains in mouse sera 28 days post colonisation with the wild type 6B or example live attenuated encapsulated strains compared with uncolonised controls. (D) and (E) Flow cytometry analysis of IgG binding (presented as MFIs of IgG deposition, panel D) to live *S. pneumoniae* wild type 6B, TIGR4 and D39 strains in 25% mouse sera 28 days post colonisation with the wild type 6B or example live attenuated encapsulated strains compared with uncolonised controls. (E) Example of a flow cytometry histogram for IgG binding to the wild D39 strain. Error bars represent standard deviation and asterisks represent statistical significance compared to uncolonised controls (panels A, B and D) or between wild-type and unencapsulated strains (panel C) (Kruskal-Wallis test with Dunn's correction for multiple comparisons) *p<0.05;  p<0.05; * p<0.001; **** p<0.0001).

Figure 2A:
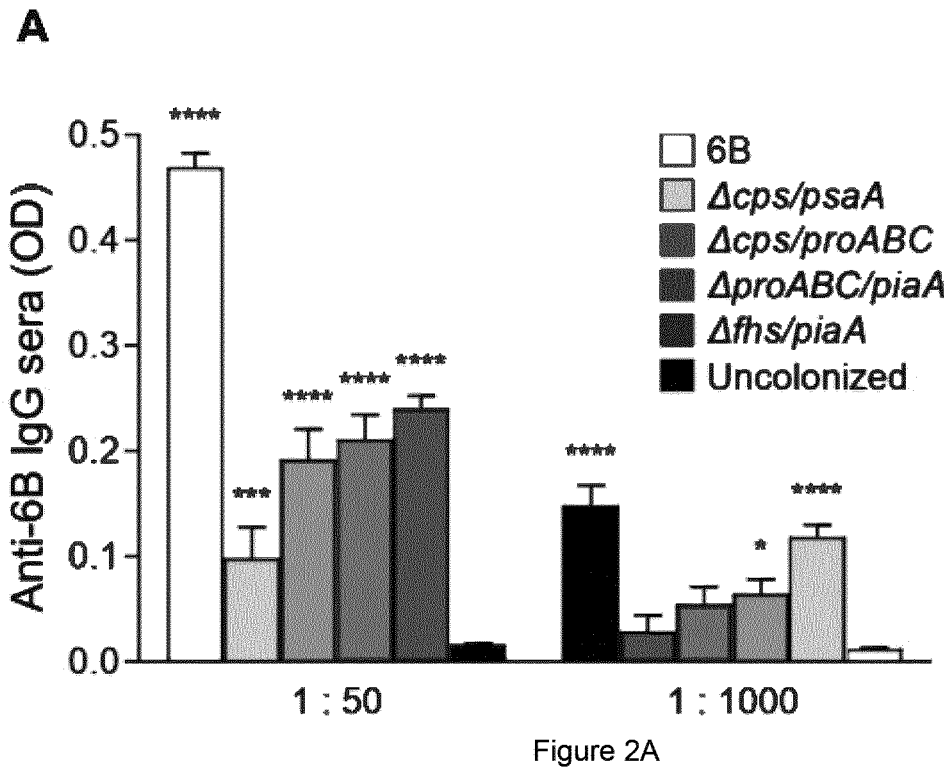
FIG. 2 shows the serological responses to colonisation with the wild type *S. pneumoniae* strain or example live attenuated *S. pneumoniae* strains in mice.
Figure 2B:
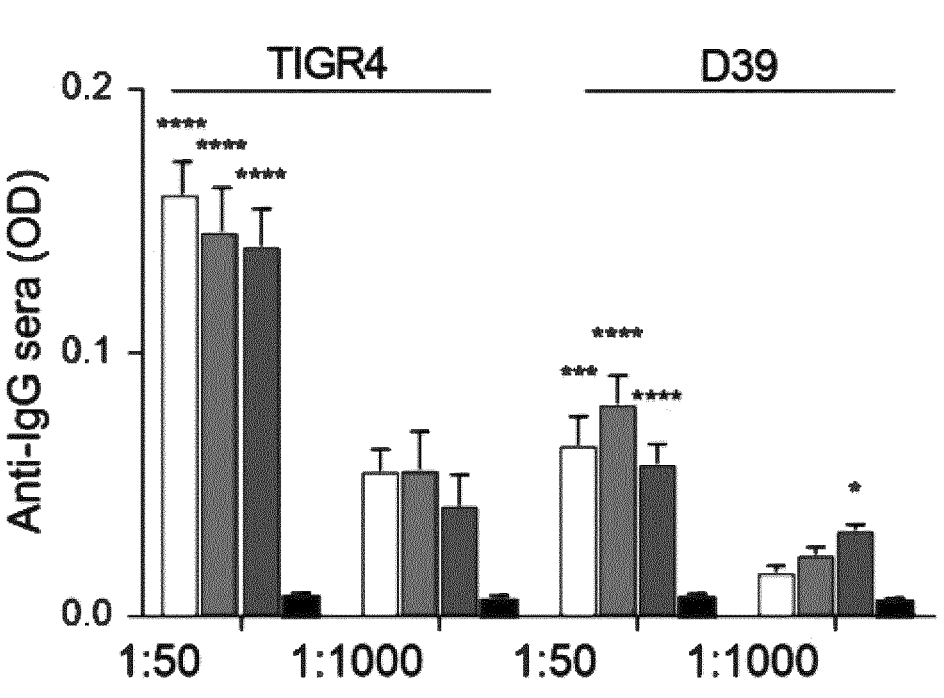
Figure 2C:
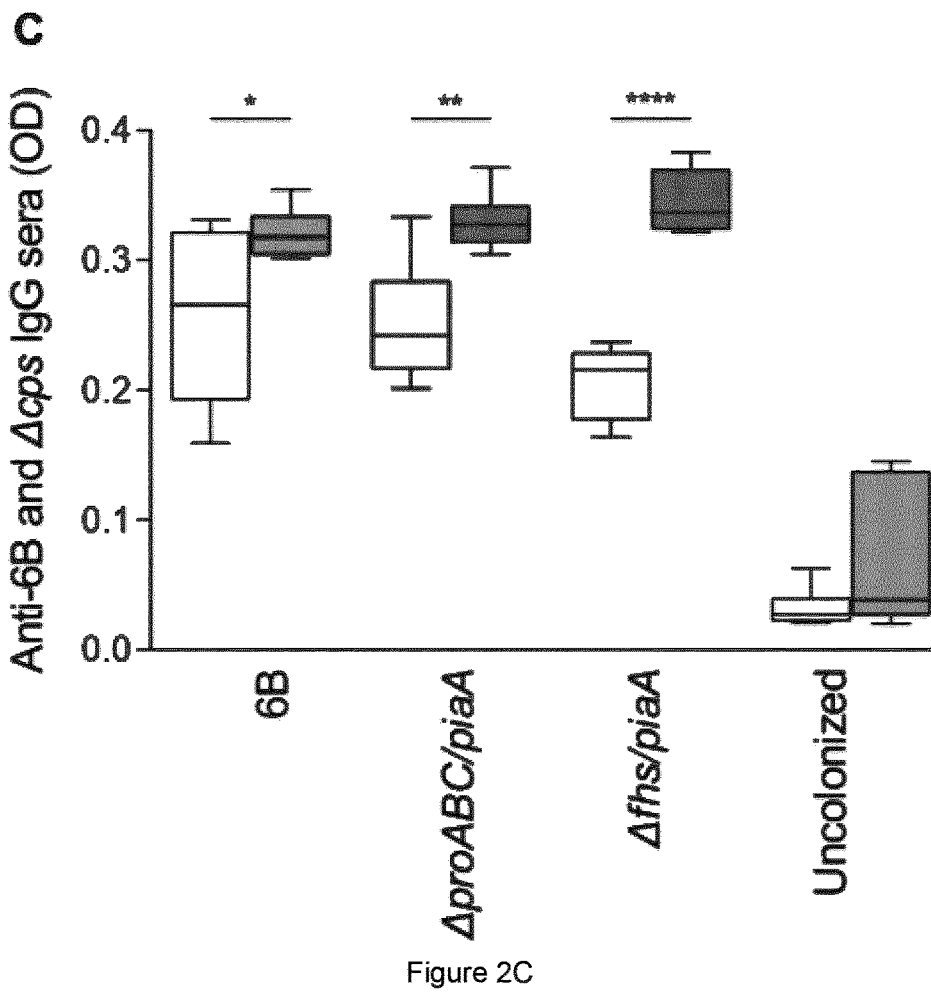
Figure 2D:
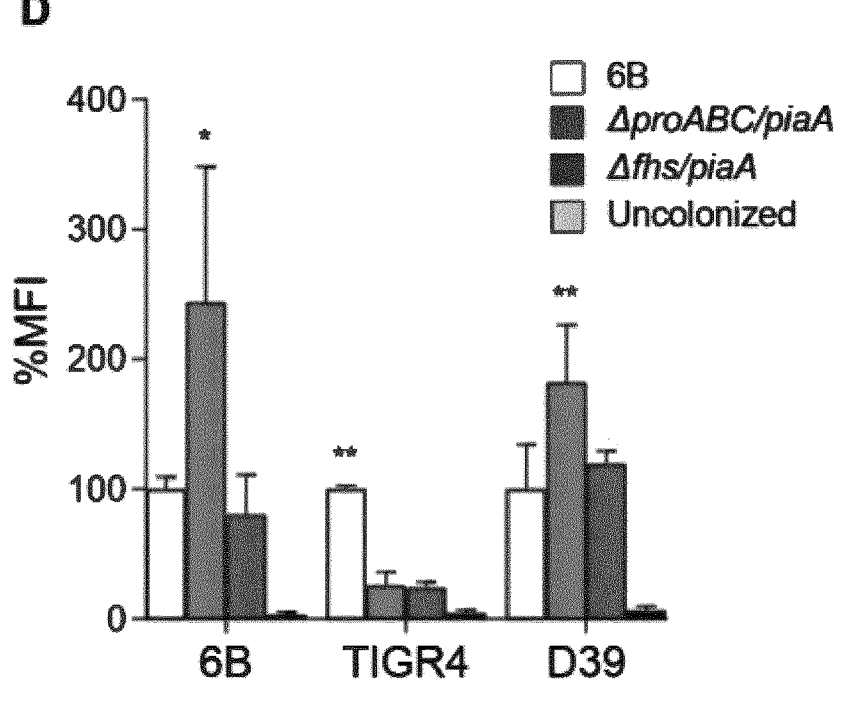
Figure 2E:
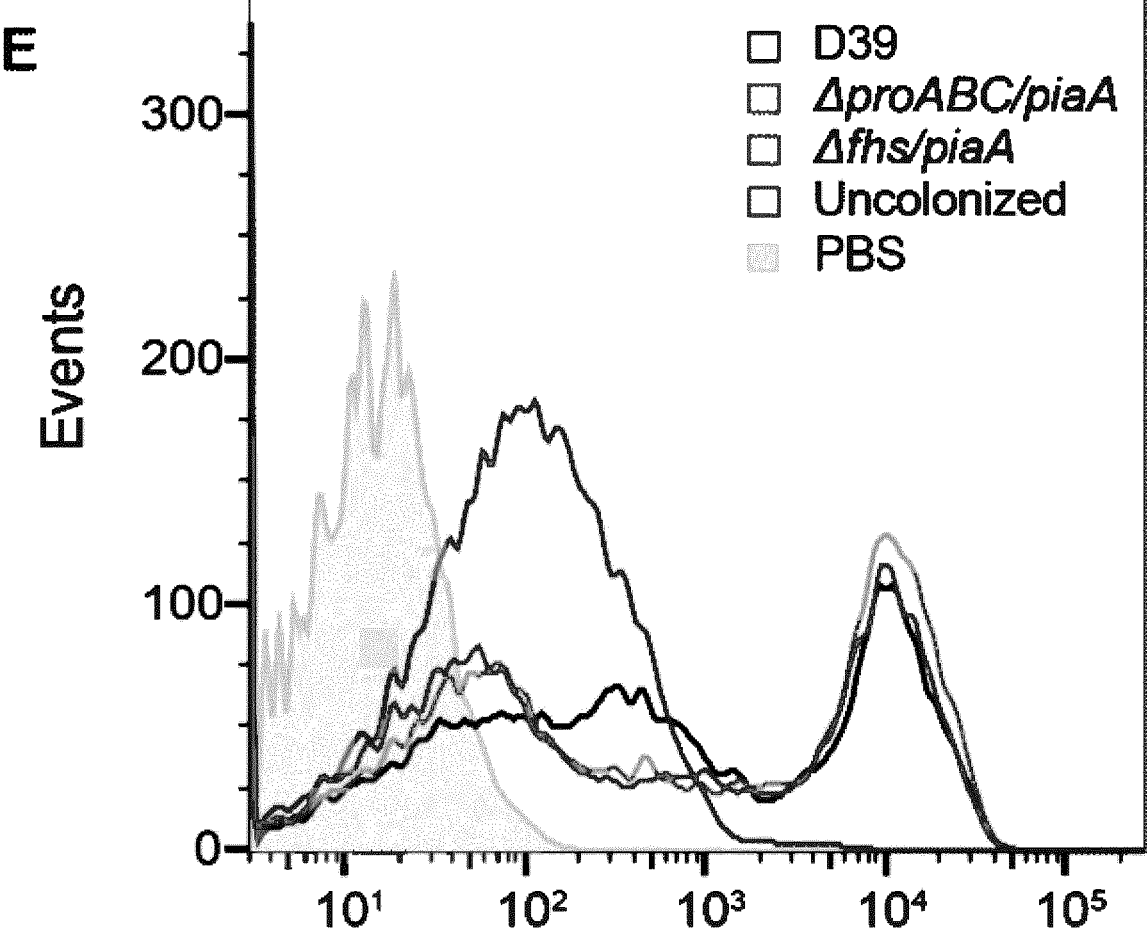

Whole cell ELISAs using serum recovered 21 days after two episodes of colonisation with the double mutant strains demonstrated significant serum IgG responses to the homologous 6B strain, although these were generally weaker than responses for mice colonised with the wild type strain (FIG. 2A). Serum IgG from mice colonised with the ΔproABC/piaA and Δfhs/piaA strains also recognised two heterologous *S. pneumoniae* strains, TIGR4 and D39, (FIG. 2B) and had higher whole cell ELISA IgG responses to the unencapsulated mutant 6B strain compared to encapsulated 6B (FIG. 2C). Flow cytometry IgG deposition assays also confirmed that serum IgG from mice colonised with wild type, ΔproABC/piaA or Δfhs/piaA strains recognised and opsonised live homologous 6B and heterologous TIGR4 and D39 *S. pneumoniae* strains (FIG. 2D, 2E). Together, these data suggest colonisation with the virulence-attenuated strains induced significant antibody responses and particularly against non-capsular antigens.

Global Assessment of Antibody Responses to Protein Antigens

Figures 3A, 3B, 3C, 3D, 3E, 3F:
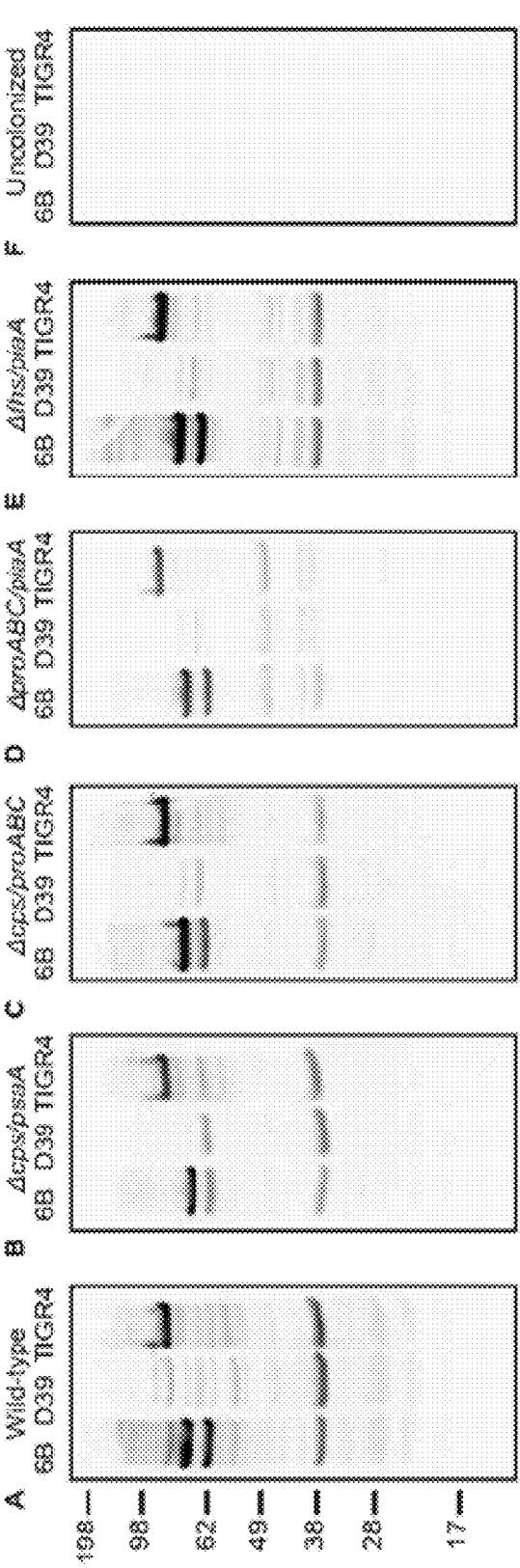
FIG. 3 shows the identification of the protein antigens recognized by IgG in serum from mice colonised with either a wild type *S. pneumoniae* strain or example ΔproABC/piaA or Δfhs/piaA live attenuated *S. pneumoniae* strains.
Figures 3G, 3H:
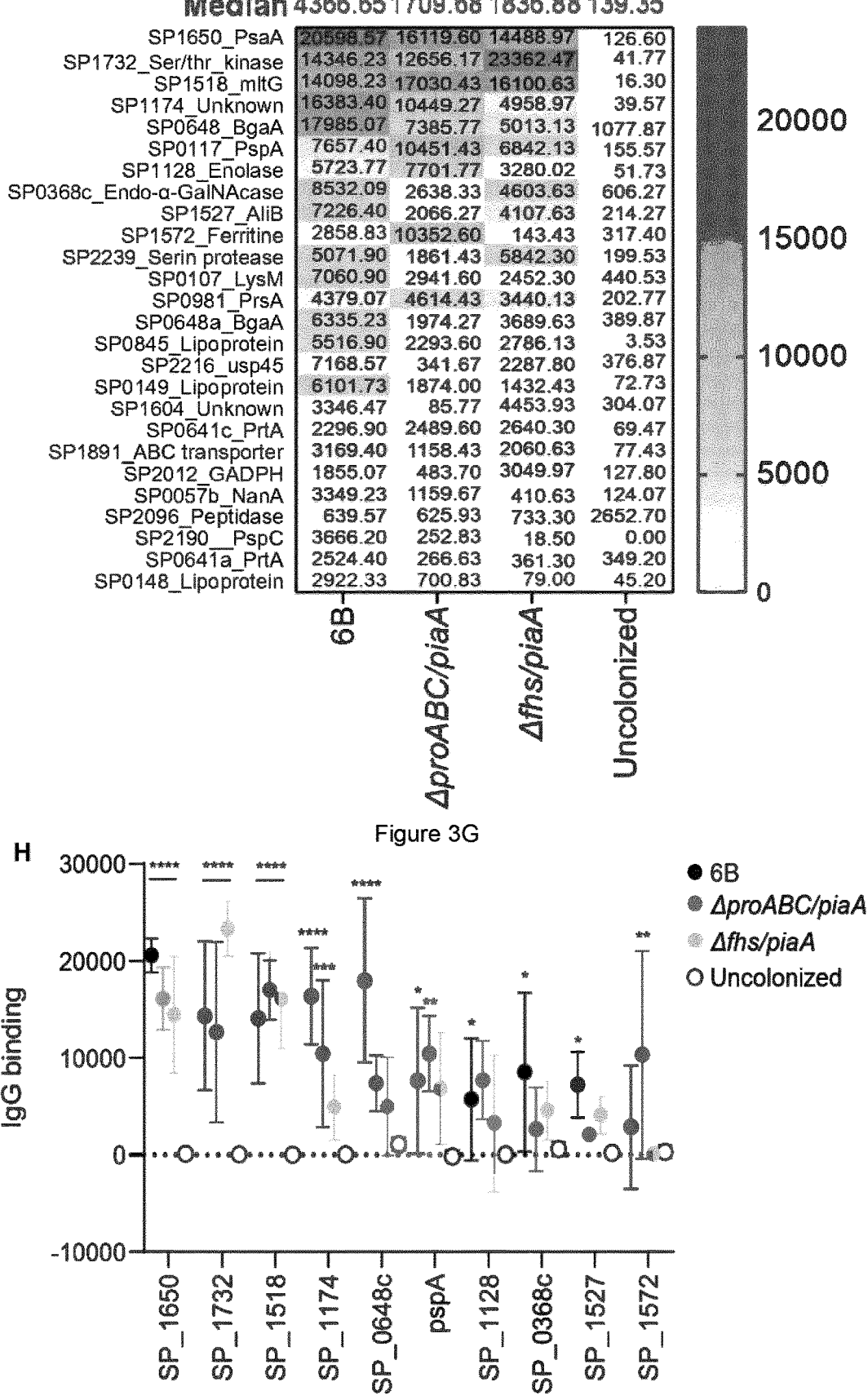

FIG. 3 shows the Identification of the protein antigens recognized by IgG in serum from mice colonised with wild type and example live attenuated *S. pneumoniae* strains Δfhs/piaA and ΔproABC/piaA. (A) to (F) IgG immunoblots for whole-cell lysates of three different *S. pneumoniae* strains (6B, D39 and TIGR4) probed with sera obtained day 28 after two episodes of colonisation with (A) 6B, (B) Acsp/psaA, (C) Δcps/proABC, (D) ΔproABC/piaA, and (E) Δfhs/piaA strains, or sham colonised (F). (G) and (H) IgG binding data to a protein array containing 289 *S. pneumoniae* protein antigens when probed with sera from mice colonised twice with the 6B strain, ΔproABC/piaA, or Δfhs/piaA strains. (G) Heat map of the level of IgG binding to the top 26 proteins recognised by IgG in colonised mouse sera (pooled data for all 6 mice within a colonisation group). (H) Interleaved symbol plot showing the binding results for the ten antigens with the highest level of IgG binding in serum from mice colonised twice with the 6B, ΔproABC/piaA, or Δfhs/piaAstrains, or sham colonised. Each symbol represents data from 6 mice, with horizontal bars representing the means and error bars represent interquartile range. Asterisks represent statistical significance compared to the uncolonised group (two-way ANOVA with Dunnett's for multiple comparisons, *, $p<0.05$; , $p<0.01$; *, $p<0.001$, ****, $p<0.0001$).

Figures 4A, 4B, 4C, 4D, 4E, 4F, 4G, 4H:
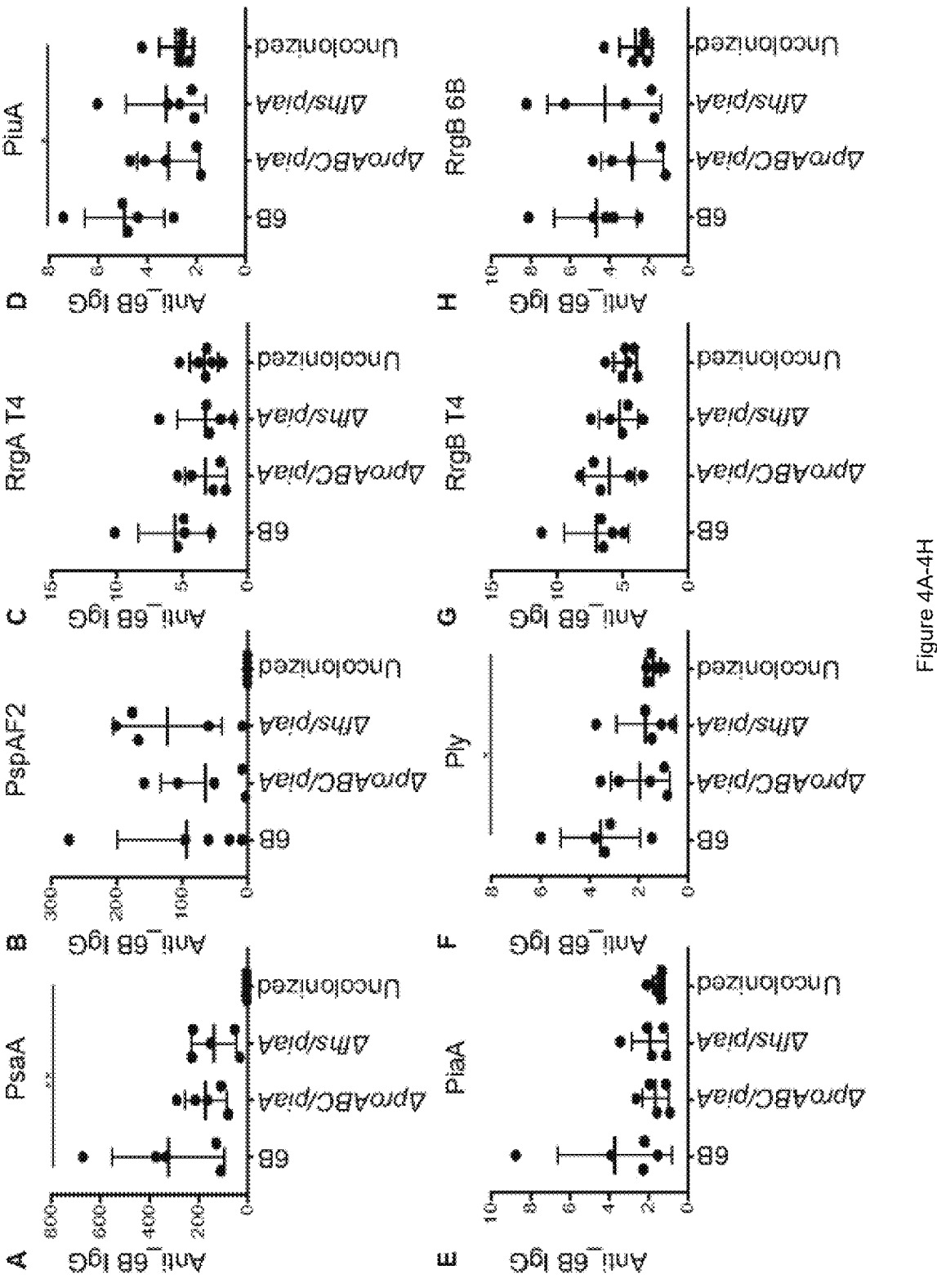
FIG. 4 shows the measurement of antibody levels to multiple pneumococcal proteins in serum from mice obtained on day 30-post colonization with the wildtype *S. pneumoniae* strain or example ΔproABC/piaA or Δfhs/piaA live attenuated *S. pneumoniae* strains.

Compatible with the ELISA and flow cytometry data showing recognition of heterologous capsular serotypes and the unencapsulated 6B strain, no significant anti-capsular responses were detected using a Meso Scale Discovery (MSD) multimeric bead assay in sera from mice colonised with mutant or wild type strains (data not shown). Instead, immunoblots confirmed serum IgG from colonised mice recognised multiple protein bands in *S. pneumoniae* 6B, TIGR4 and D39 strains lysates (FIG. 3A-F). A protein array containing the majority of conserved *S. pneumoniae* proteins recognised by naturally acquired antibody found in human sera was used to identify which *S. pneumoniae* protein antigens were recognised by serum IgG from mice colonised with the wild type, ΔproABC/piaA or Δfhs/piaA strains. Significant antibody responses were detected to a subset of 30 proteins. There was considerable overlap in recognised antigens between sera from mice colonised with the wild type or double mutant strains, although the mean overall antibody levels to the top 20 antigens were 61% and 58% lower for the latter (FIGS. 4G and H). The protein antigens with the strongest responses were PsaA (SP_1650), StkP (SP_1732), MitG (SP_1518), SP_1174, BgaA (SP_0648), and PspA (SP_0117). An MSD assay independently confirmed mice colonised with either wild type or ΔproABC/piaA and Δfhs/piaA strains had raised IgG levels to PsaA and PspA (F2 allele), along with occasional weak responses from one or two mice per group for the other antigens (PspA, RrgA, PiuA, PiaA, RrgB T4 and RrgB 6B). FIG. 4 shows the measurement of antibodies to multiple pneumococcal proteins in serum obtained on day 30-post colonization of the example live attenuated strains from 5 mice. 8 different pneumococcal antigens were recognized by serum immunoglobulin IgG responses to 6B or example live attenuated ΔproABC/piaA and Δfhs/piaA mutants colonized. Each symbol represents data from serum recovered from a single mouse, horizontal bars represent mean values and error bars represent SD and asterisks represent statistical significance compared to uncolonized group (Kruskall-Wallis with Dunn's post hoc test to identify significant differences between groups, *, $p<0.05$; **, $p<0.01$).

Double Mutant Colonisation Protects Against Pneumonia Challenge

The protective efficacy of prior colonisation with the double mutant strains was assessed by challenge with the 6B wild type strain 30 days later.

Figure 5:
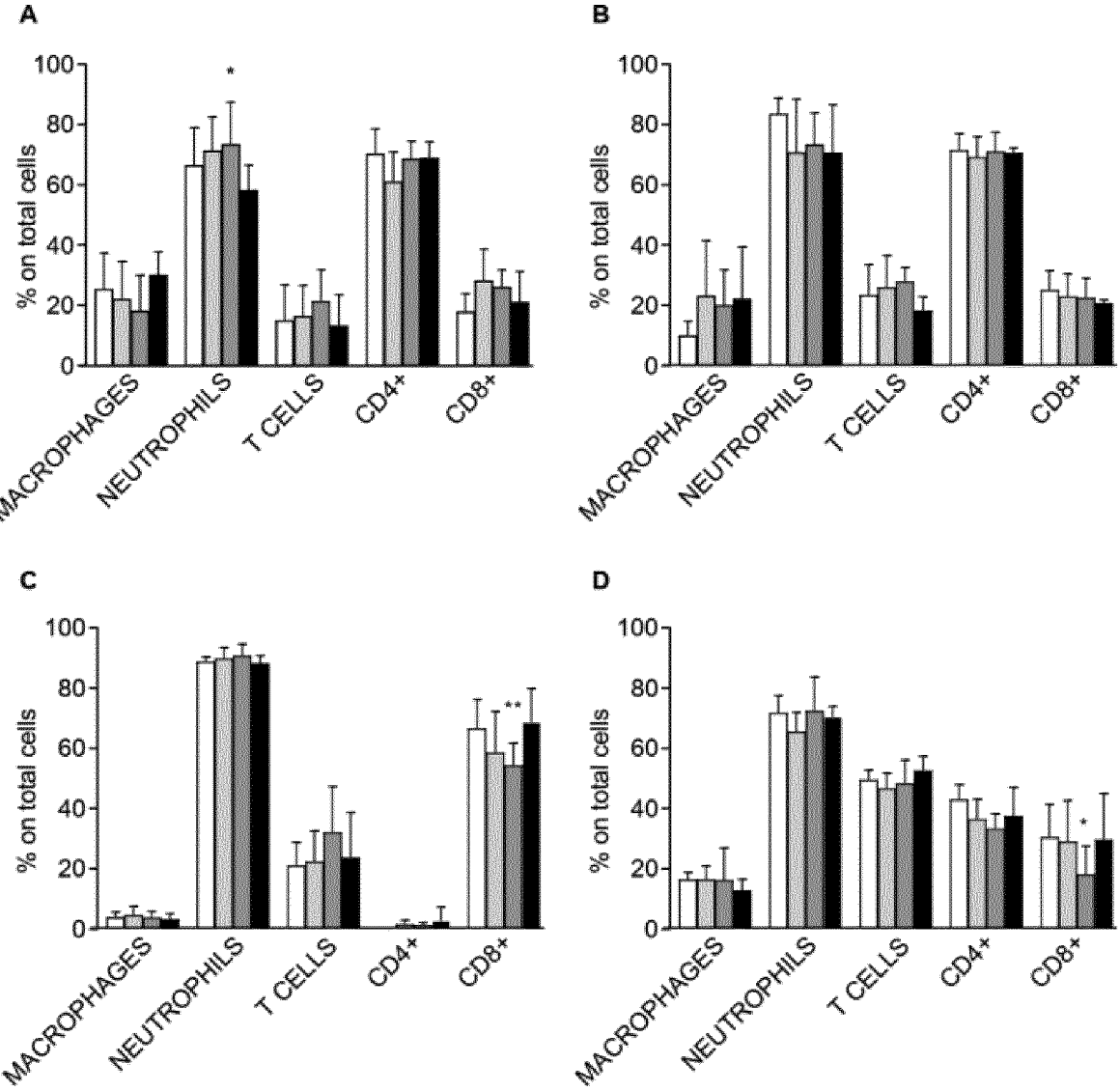
FIG. 5 shows the cellular immune responses to lung infection challenge after previous pneumococcus colonization with a wildtype *S. pneumoniae* strain or example ΔproABC/piaA or Δfhs/piaA live attenuated *S. pneumoniae* strains. Sham-(black columns), 6B (clear columns), example live attenuated ΔproABC/piaA mutant strain (light grey colour) or example live attenuated Δfhs/piaA (dark grey colour) colonised mice.

FIG. 5 shows the cellular immune responses to lung infection challenge after pneumococcus colonization with the example live attenuated strains Δfhs/piaA and ΔproABC/piaA. (A) and (B) percentage of cells in lungs from sham- (black columns), 6B (clear columns), example live attenuated ΔproABC/piaA mutant strain (light grey colour) or example live attenuated Δfhs/piaA (dark grey colour) mutant strain-colonized mice 28 h following lung infection on day 30 with $1\times10^7$ CFU (A) *S. pneumoniae* 6B, (B) TIGR4 in wild type mice, (C) with 6B strain in T cell depleted CD-1 mice or (D) 6B in µMT$^{-/-}$ mice. Data were obtained from six mice per group and are presented as SD. P-values were obtained using 2-way ANOVA with Dunnett's post-test (*$p<0.05$, ** $p<0.01$).

Figures 6A, 6B, 6C, 6D, 6E, 6F, 6G, 6H:
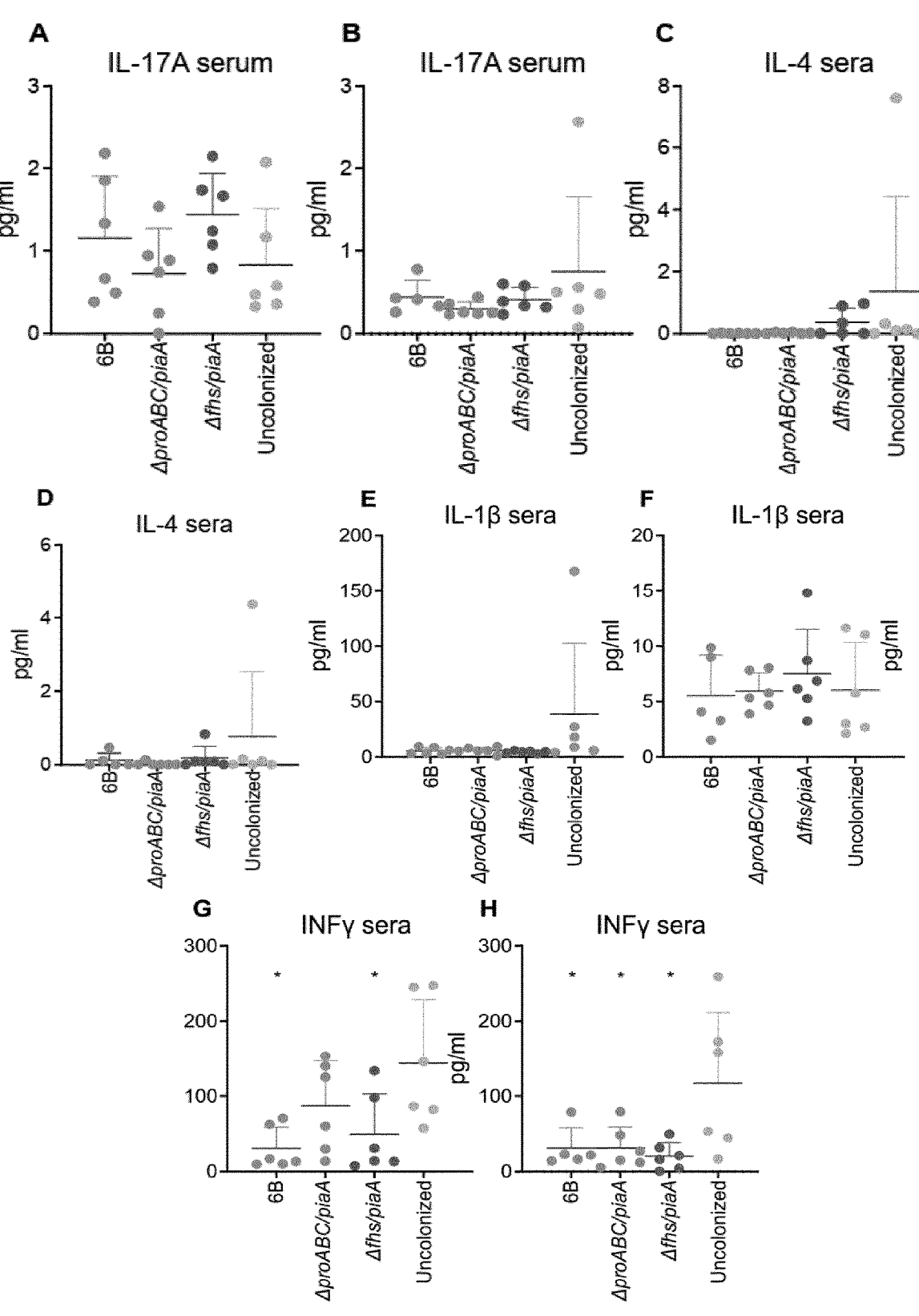
FIG. 6 shows the impact of previous nasopharynx colonization of a wildtype *S. pneumoniae* strain and example ΔproABC/piaA or Δfhs/piaA live attenuated *S. pneumoniae* strains on the serum cytokine response to lung infection challenge.
Figures 6I, 6J, 6K, 6L, 6M, 6N:
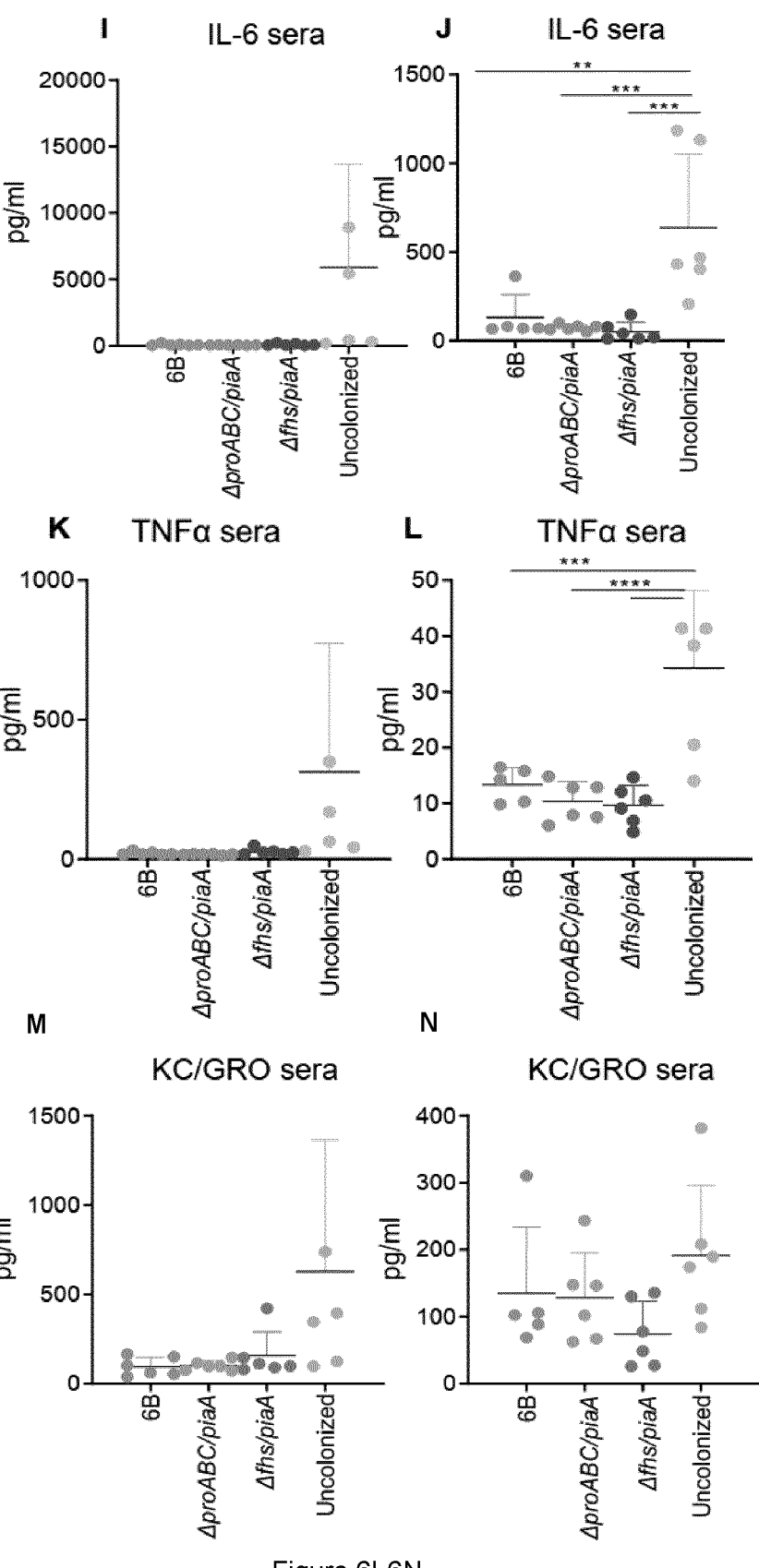

FIG. 6 shows the impact of nasopharynx colonization of the example live attenuated strains Δfhs/piaA and ΔproABC/piaA in the inflammatory response after pneumococcal infection. This is determined by measurement of cytokine levels (pg/ml) which were measured in serum recovered from wild-type CD-1 mice (A, C, E, G, I, K, M) and T cell depleted mice (B, D, F, H, J, L, N) at 24 h after intranasal inoculation of *S. pneumoniae* 6B strain. Error bars represent the SDs and asterisks indicate statistical significance of cytokine levels of 6B and example live attenuated strain colonized mice compared to uncolonized mice.

Figures 7A, 7B, 7C, 7D, 7E, 7F, 7G, 7H:
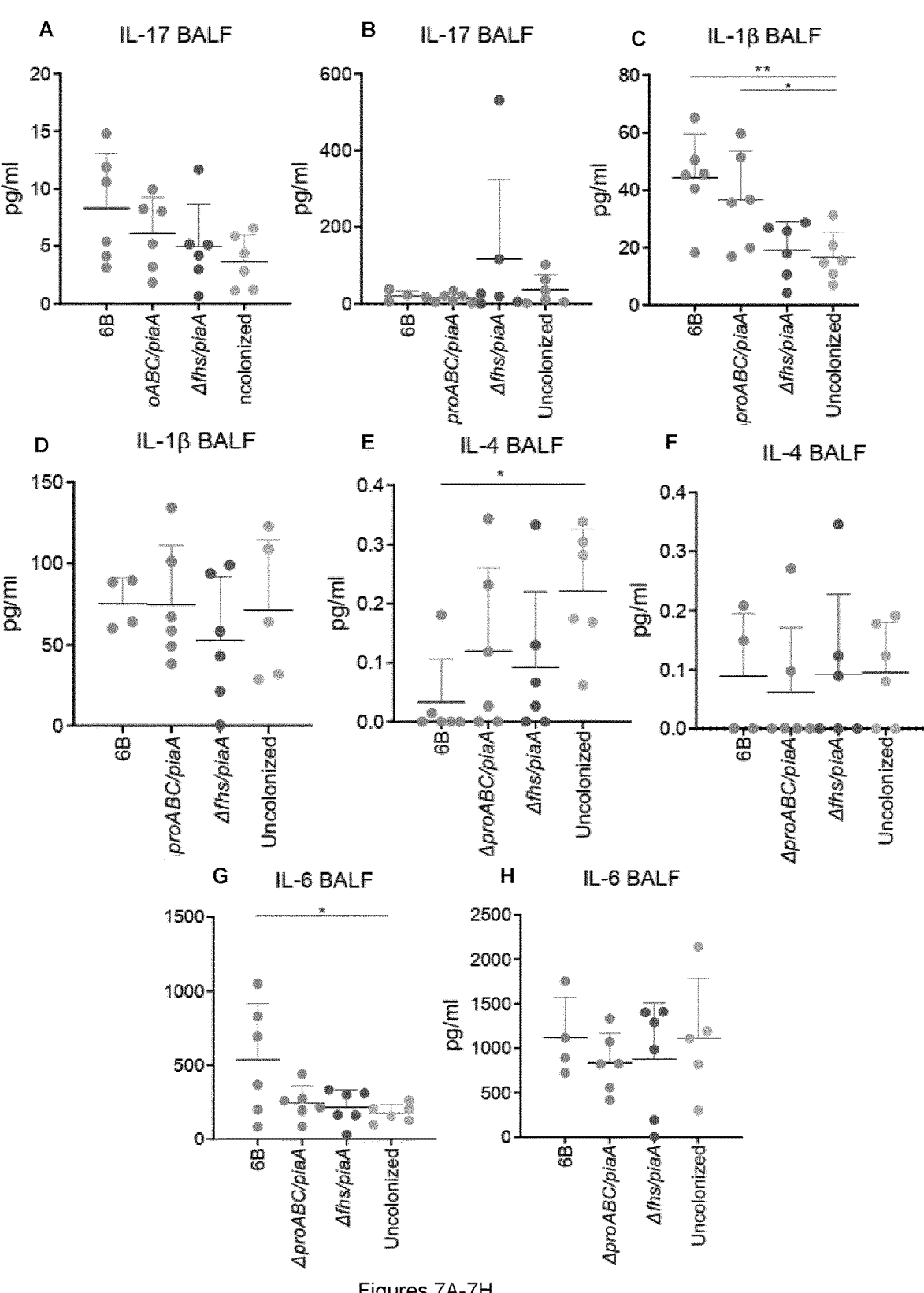
FIG. 7 shows the impact of nasopharynx colonization of wildtype *S. pneumoniae* strain and example ΔproABC/piaA or Δfhs/piaA live attenuated *S. pneumoniae* strains on the bronchoalveolar lavage fluid cytokine response to lung infection challenge.
Figures 7I, 7J, 7K, 7L, 7M, 7N:
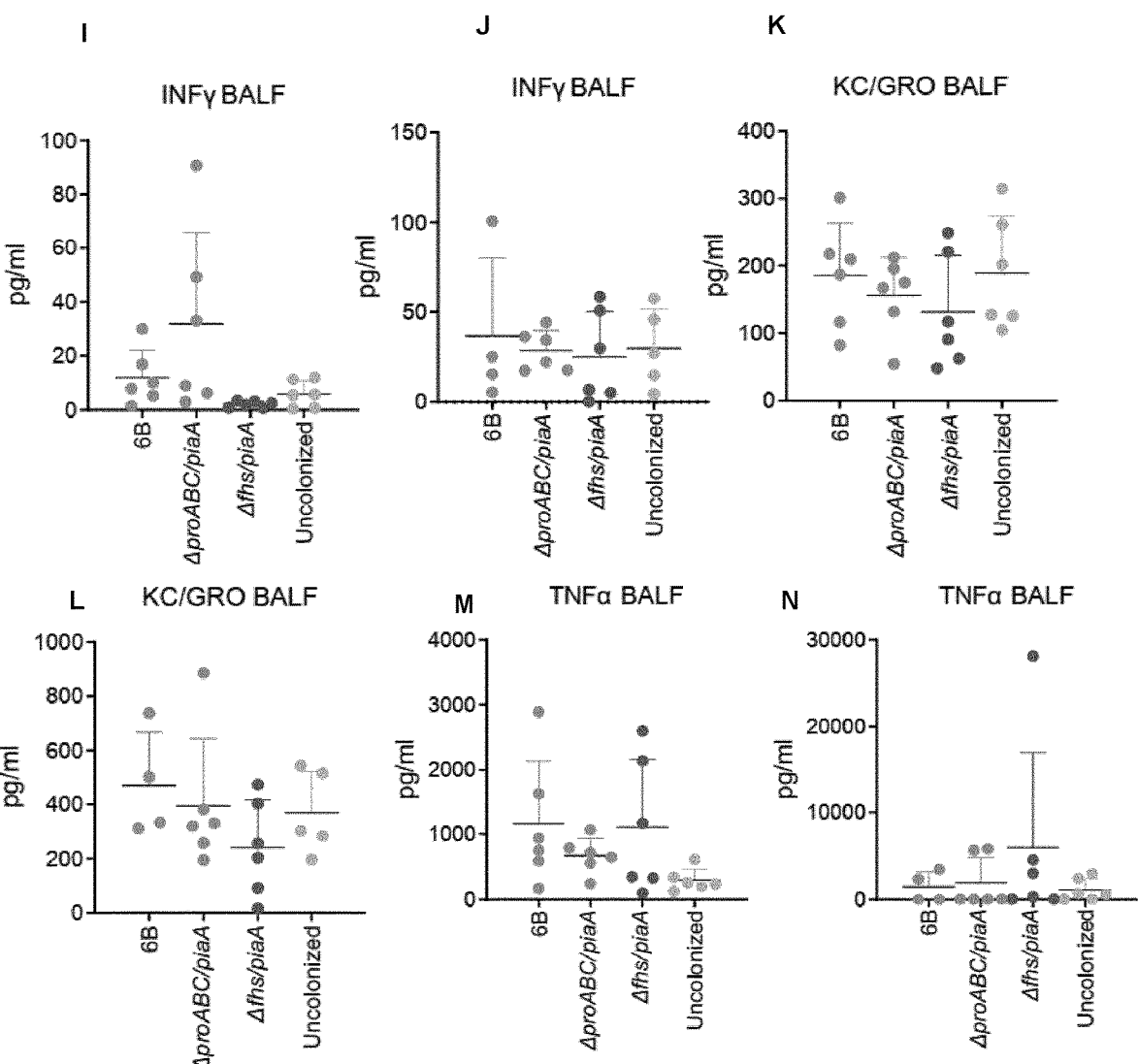

FIG. 7 shows the impact of impact of nasopharynx colonization of the example live attenuated strains Δfhs/piaA and ΔproABC/piaA in the inflammatory response after pneumococcal infection. This is determined by measurement of cytokine levels (pg/ml) were measured in BALF recovered from wild-type CD-1 mice (A, C, E, G, I, K, M) and T cell depleted mice (B, D, F, H, J, L, N) at 24 h after intranasal inoculation of *S. pneumoniae* 6B strain. Error bars represent the SDs and asterisks indicate statistical significance of cytokine levels of 6B and example live attenuated strain colonized mice compared to uncolonized mice.

Figure 8A:
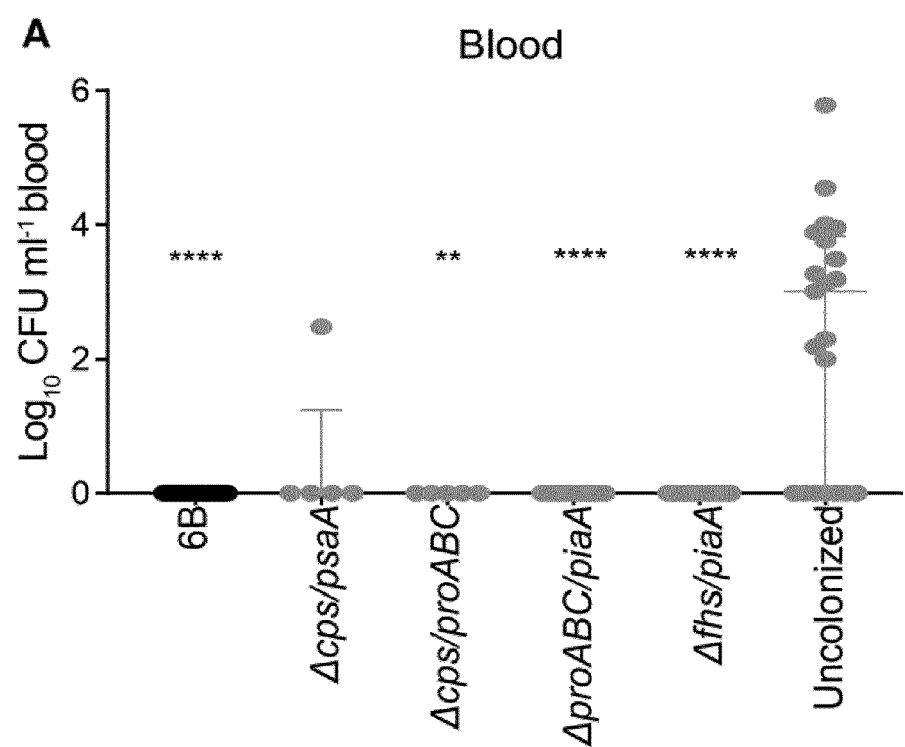
FIG. 8 shows how nasopharynx colonisation with the example ΔproABC/piaA or Δfhs/piaA live attenuated *S.*
Figure 8B:
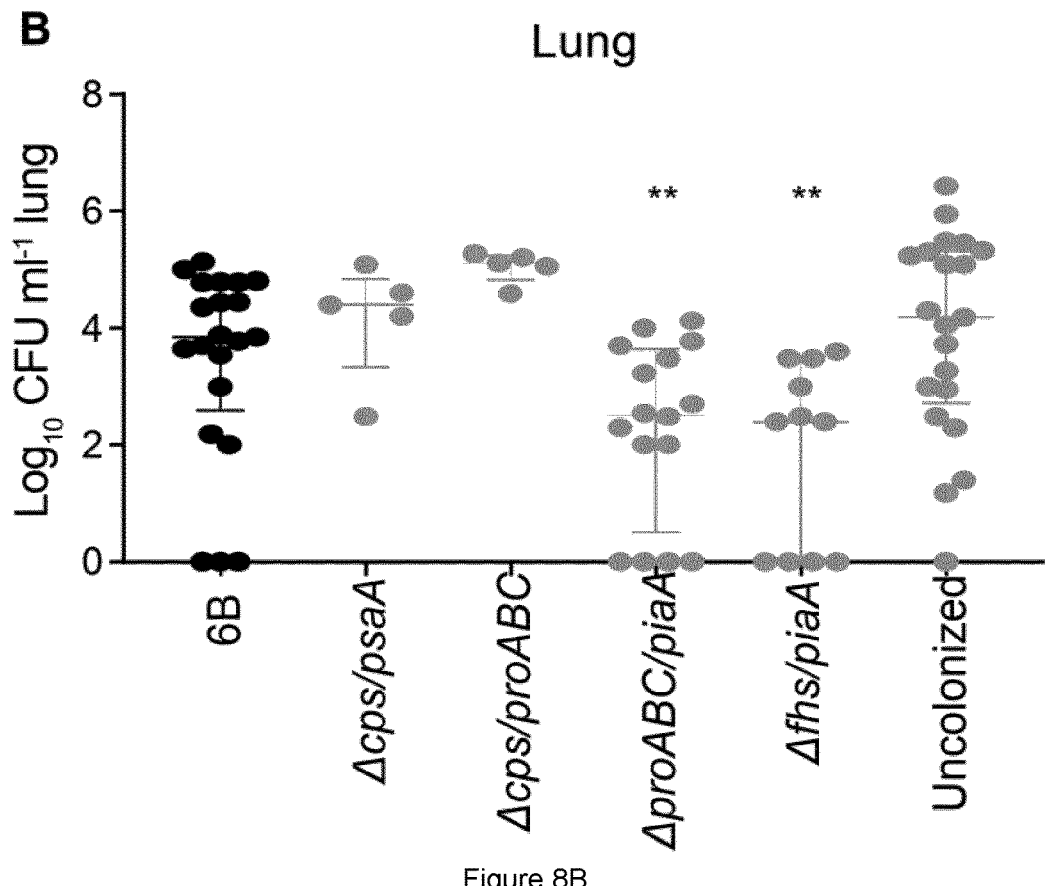

After pneumonia rechallenge, there were no major changes in macrophage, neutrophil, or CD4+ and CD8+ T cells populations between lungs of mice colonised with either wild type or the double mutant *S. pneumoniae* strains and lungs of uncolonised control mice (FIG. 5). On rechallenge, control uncolonised mice tended to have higher serum and lower BALF levels of proinflammatory cytokines than previously colonised mice, but most of these differences were not statistically significant FIG. 6 and FIG. 7). Levels of IL-17 were too low to identify any consistent pattern. Despite the limited detectable changes in the inflammatory response, mice previously colonised with either wild type or the double mutant pneumococcal strains were totally protected against bacteraemia (FIG. 8A) after 6B wild type *S. pneumoniae* pneumonia challenge. In addition, mice colonised with the ΔproABC/piaA and Δfhs/piaA (but not the unencapsulated Δcps/psaA and Δcps/proABC strains) had reduced bacterial CFU within the lung after pneumonia challenge (FIG. 8B).

FIG. 8 shows nasopharynx colonisation with the example live attenuated strains Δfhs/piaA and ΔproABC/piaA protects against systemic infection after challenge with the wild type 6B strain. (A) and (B) *S. pneumoniae* CFU recovered from blood (A), and lung (B) following intranasal challenge on day 30 with 1×10' CFU *S. pneumoniae* 6B of CD1 mice after two episodes of colonisation with wild type 6B or example live attenuated *S. pneumoniae* strains, or after sham colonisation. (C) to (E) Repeat pneumonia challenge in previously colonised wild type or µMT$^{-/-}$ C57BL/6J mice. (C) Representative flow cytometry dot-plot of splenocytes from µMT$^{-/-}$ mice gating on CD19+ and CD3+, showing absent B cell population (CD19 hi). *S. pneumoniae* CFU recovered from blood (D), and lung (E) following intranasal challenge on day 30 with $1 \times 10^7$ CFU *S. pneumoniae* in wild type (black symbols) or µMT (grey symbols) C57BL/6J mice after two episodes of colonisation with wild type 6B or example live attenuated *S. pneumoniae* strains. (F) to (H) Repeat pneumonia challenge in previously colonised wild type mice with or without CD4+ cell depletion prior to challenge. (F) Representative flow cytometry dot-plot of splenocytes recovered from mice treated pre-challenge with anti-CD4+ antibody (GK1.5) with gating on CD4+CD8a+ populations and showing an absent CD4+ cell population. *S. pneumoniae* CFU recovered from blood (G), and lung (H) following intranasal challenge on day 30 with $1 \times 10^7$ CFU *S. pneumoniae* in untreated (black symbols) or CD4+ depleted (grey symbols) CD1 mice after two episodes of colonisation with wild type 6B or example live attenuated *S. pneumoniae* strains. Each symbol represents data from an individual mouse, horizontal bars represent median values, error bars represent interquartile range and asterisks represent statistical significance compared to the wild type strain. For panels A and B we used a Kruskall-Wallis with Dunn's post hoc test to identify significant differences between groups, , p<0.01; , p<0.0001). For panels (D), (E), (G) and (H) p-values were obtained using 2way ANOVA test with a Sidak's test for multiple comparisons (**, p<0.0001).

Protection from Sepsis Requires Antibody but not CD4+ Lymphocytes

To assess the protective role of antibody, colonisation and rechallenge experiments were repeated using B cell deficient µMT mice.

Figure 8C:
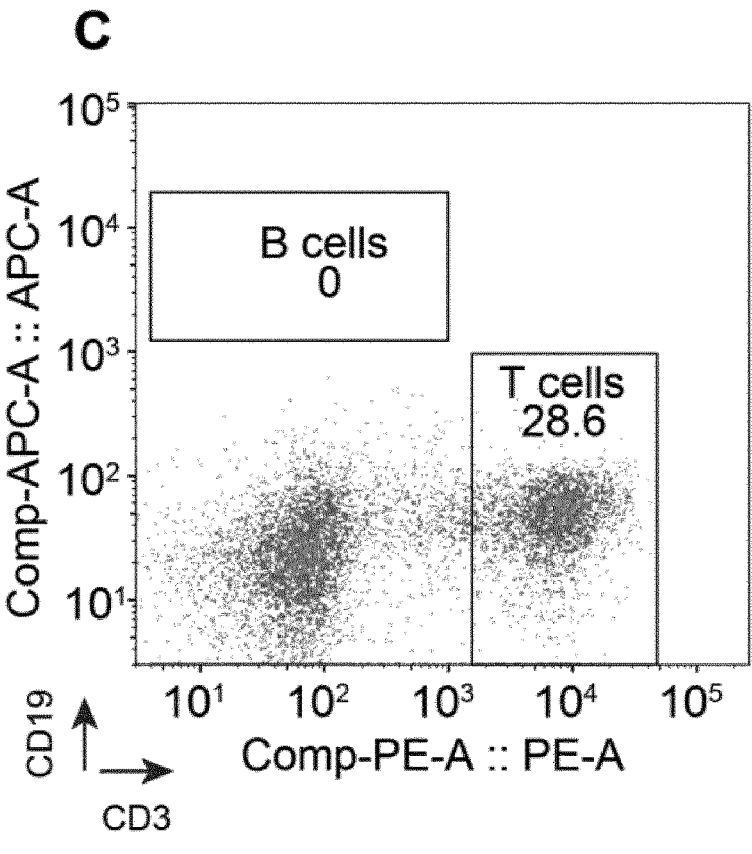
Figure 8D:
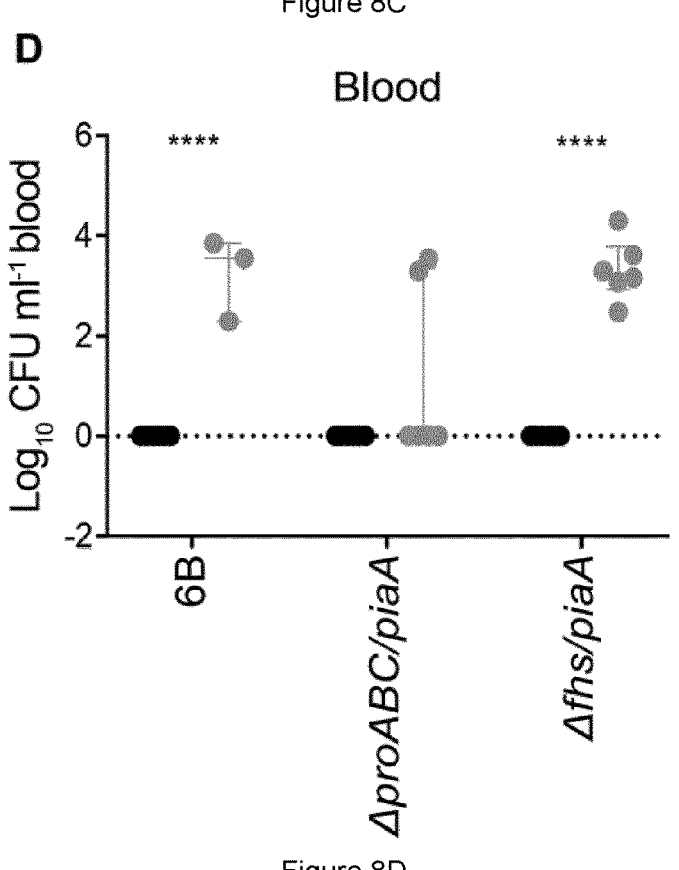
Figures 8E, 8F:
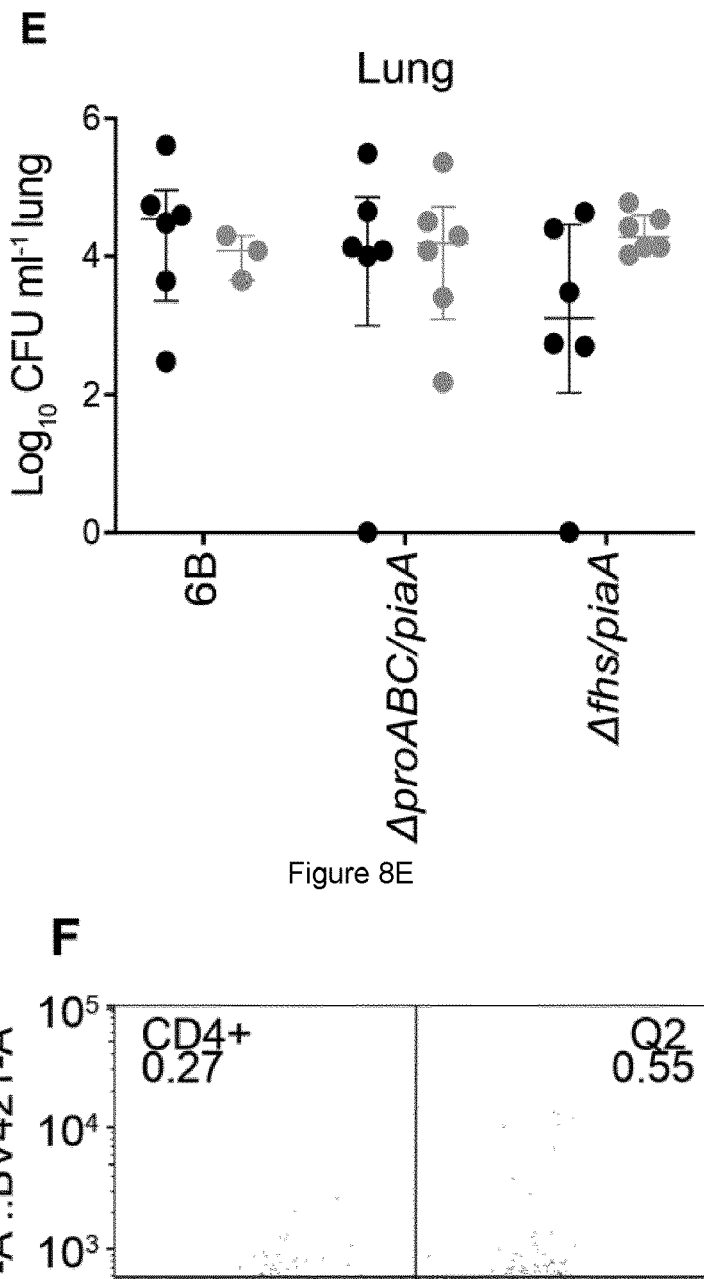
Figures 8G, 8H:
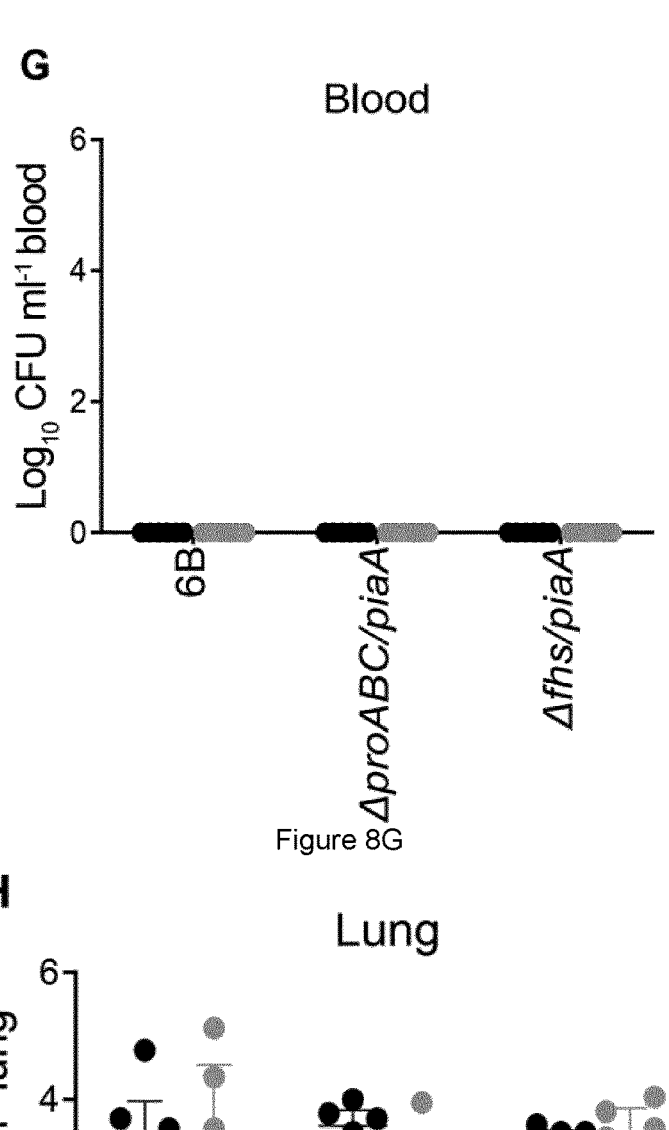

Flow cytometry confirmed the absence of B cells in µMT mice (FIG. 8C), and as expected whole cell ELISAs demonstrated no IgG response to colonisation with *S. pneumoniae* wild type or mutant strains (data not shown). Prior colonisation with *S. pneumoniae* wild type or the Δfhs/piaA strains failed to prevent bacteraemia in uMT mice (FIG. 8D). The blood CFU data obtained for the ΔproABC/piaA strain were inconclusive, and there were no significant differences in lung CFU between wild type and µMT mice in previously colonised mice (FIG. 8E). To determine whether CD4+ cells were important for protection from pneumonia induced by colonisation with the double mutant strains, colonised mice were treated with anti-CD4+ antibody before undergoing pneumonia challenge. CD4+ depletion profoundly reduced lung and spleen CD4+ cell populations with a compensatory increase in the proportions of CD8+ T cells (FIG. 8F and FIG. 8C). However, there were no differences in blood and lung CFU between control and CD4+ depleted mice (FIGS. 8G and 8H), suggesting that colonisation-induced protection against systemic infection did not require CD4+ cells.

Colonisation with ΔproABC/piaA or ΔFhs/piaA Induced CD4+-Dependent Protection Against Recolonisation with Homologous or Heterologous *S. pneumoniae* Strains Colonisation and challenge experiments were repeated with nasopharyngeal colonisation challenge with the wild type 6B strain or the heterologous TIGR4 strain, using nasal wash CFU counts 7 days after inoculation to assess nasopharyngeal colonisation.

FIG. 9 shows nasopharynx colonisation with the example ΔproABC/piaA live attenuated strain or Δfhs/piaA example live attenuated strain after recolonisation with the homologous 6B or the heterologous TIGR4 strains. (A) and (B) Serological responses measured in nasal washes recovered from mice 28 days after two episodes of colonisation twice with the wild type 6B and example live attenuated strains (n=5 per group). Measured using whole cell ELISAs against a wild type 6B strain and represented as means and SDs (panel A IgG, and panel B IgA). P-values were obtained using one-way analyses of variance (ANOVAs) and Dunnett's post-test to compare columns (*, p<0.05; , p<0.01, *, p<0.001; ****, p<0.0001). (C), (D), and (E) CFU recovered from nasal washes 7 days after intranasal recolonisation challenge of CD1 mice with $1 \times 10^7$ CFU of the *S. pneumoniae* 6B (C) or TIGR4 (D) strain 42 days after two episodes of colonisation with the wild type 6B or example live attenuated strains. (E) Nasal wash CFU for a repeat recolonisation challenge in CD1 mice depleted of CD4+ cells just prior to re-challenge with wild type 6B. For panels (C), (D), and (E) each symbol represents data from a single mouse, horizontal bars represent median values, error bars represent interquartile range and asterisks represent statistical significance compared to sham colonised group (Kruskall-Wallis with Dunn's post hoc test to identify significant differences between groups, p<0.05; *, p<0.01; *, p<0.0001).

Figures 9A, 9B:
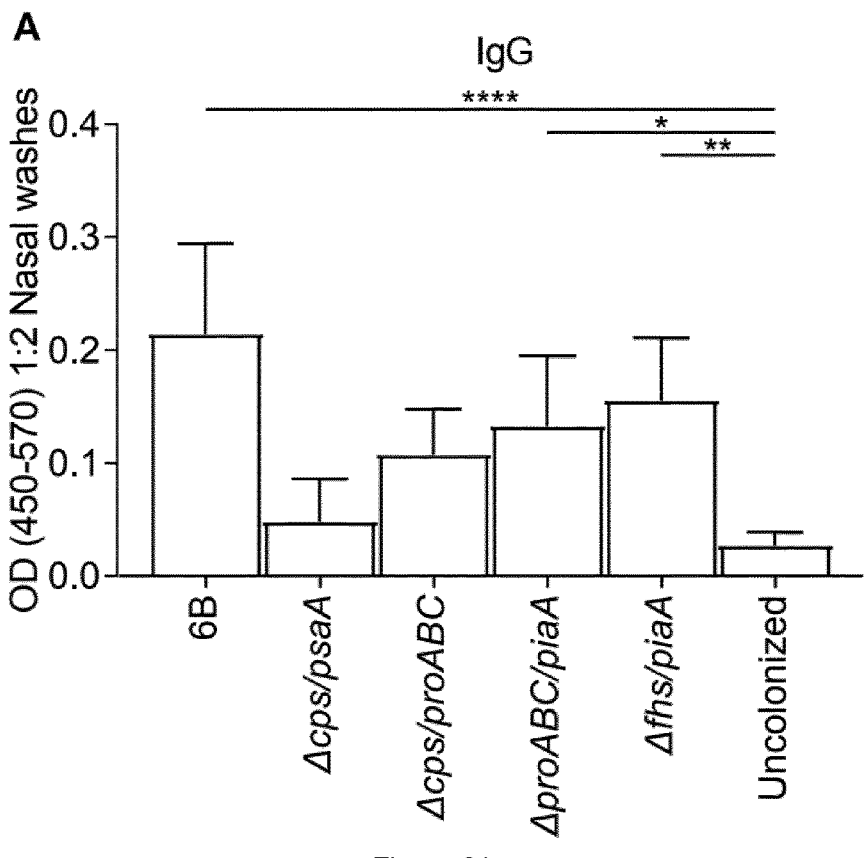
Figure 9C:
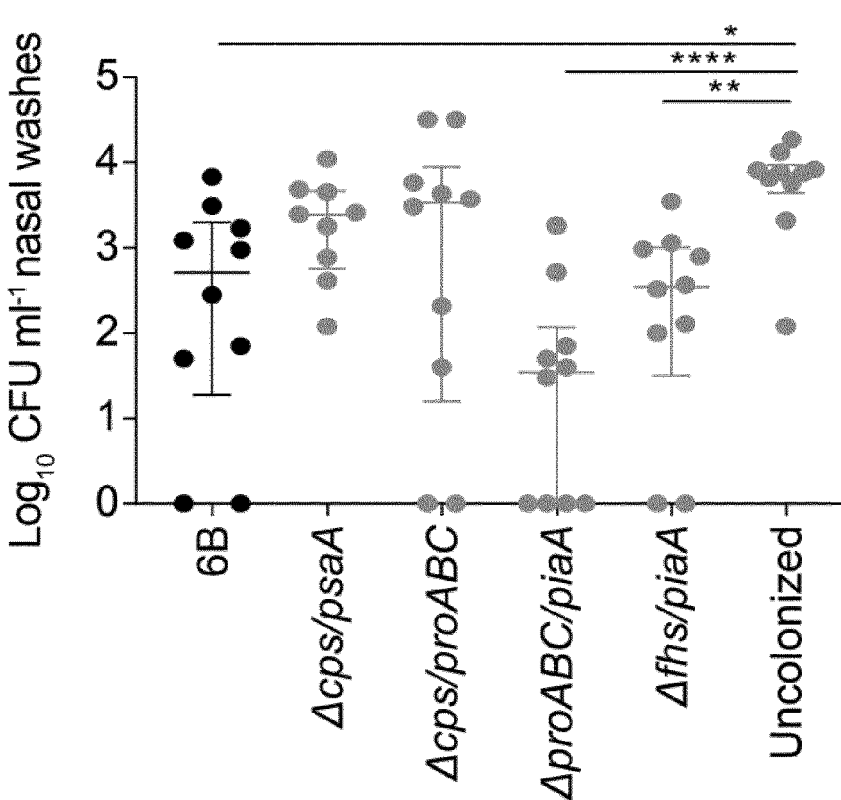
Figure 9D:
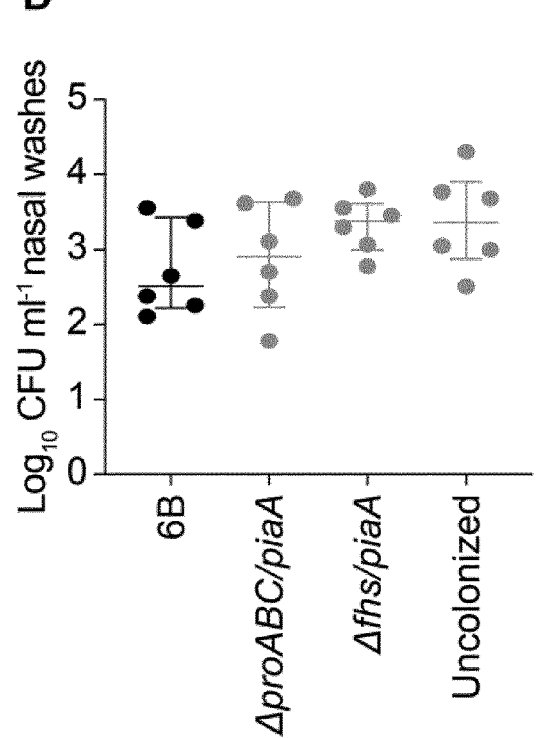
Figure 9E:
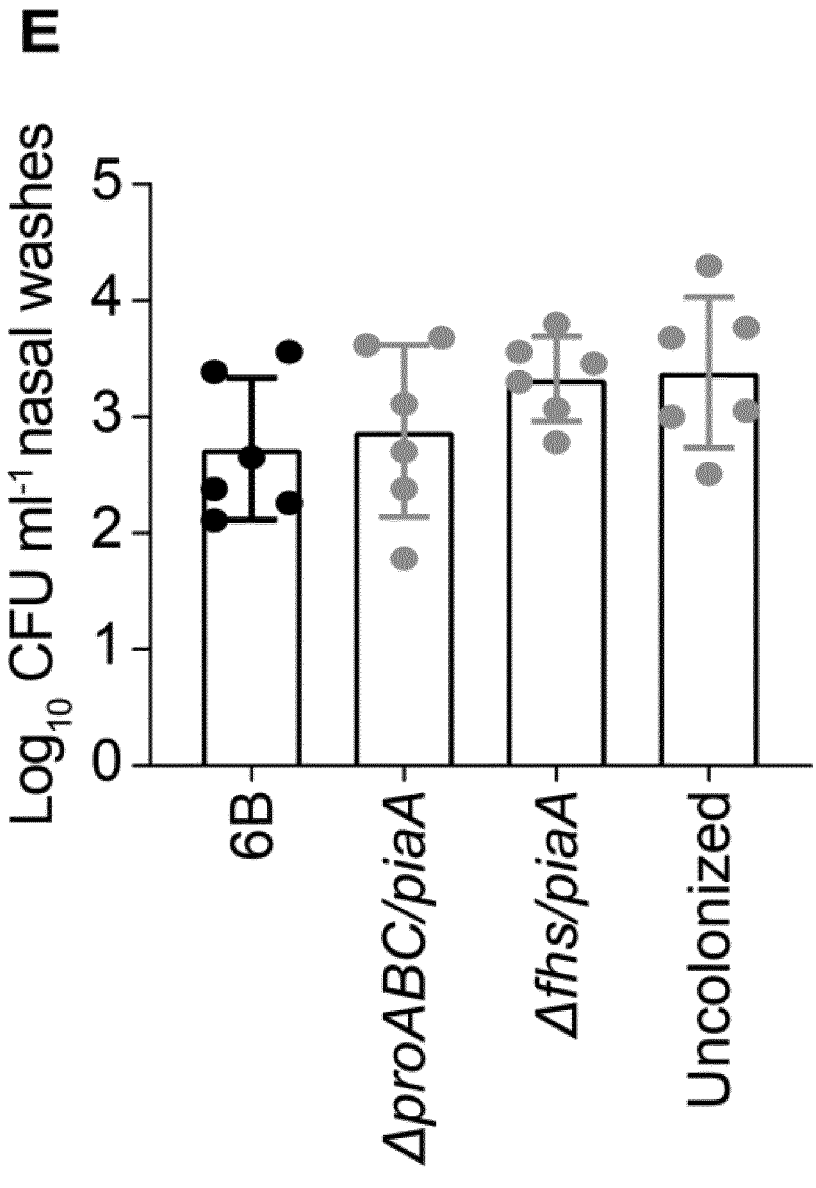

Prior colonisation raised nasal wash IgG and IgA levels to *S. pneumoniae* (FIGS. 9A and 9B), confirming colonisation induced a local immune response. Prior colonisation with either wild type, ΔproABC/piaA or Δfhs/piaA double mutant strains reduced nasal wash CFU by >1 $\log_{10}$ when mice were re-challenged with either the 6B or the TIGR4 strain (FIGS. 9C and 9D), demonstrating the protective efficacy of these two double mutant strains against subsequent colonisation with homologous or heterologous strains. Previous colonisation with the Δcps/psaA and Δcps/proABC failed to prevent recolonisation with the homologous 6B strain (FIG. 9C), possibly as the low level of colonisation achieved by these strains resulted in weaker induction of local adaptive immune responses. Pre-challenge CD4+ cell depletion prevented the protective effect of prior colonisation with the wild type, Δfhs/piaA or ΔproABC/piaA strains when mice were recolonised with wild type TIGR4 *S. pneumoniae* (FIG. 9E). Hence, colonisation-induced protection against recolonisation with the heterologous strain required CD4+ effector cells.

Growth of Mutant Strains in Human Sera

Replication of *S. pneumoniae* strains in human sera obtained from healthy volunteers or cerebrospinal fluid (CSF) from patients with normal pressure hydrocephalus was determined by inoculating with $5 \times 10^6$ CFU/well in a 200 µl volume and monitoring growth by measuring optical density ($OD_{595}$) every 30 minutes for 24 hours using a TECAN Spark® plate reader.

It was shown that Δfhs and ΔproABC mutations could not grow effectively in human cerebrospinal fluid or in human serum as compared to the wild-type 6B strain, meaning that live attenuated strains containing these mutations will be less likely to cause meningitis or septicaemia respectively. In view of this result, it is even more surprising that fhs and proABC mutants are able to successfully colonise the nasopharynx as well as the wild-type strain.

ΔSp_1288/fhs 6B double mutant strain

A *S. pneumoniae* 1288/fhs 6B double mutant strain was also generated, and Sequencing around the mutation site and amplification by PCR confirmed deletion of the relevant genes. The double mutant strain was tested using an established mouse model of pneumonia. The results confirmed that the A Sp_1288/fhs 6B strain (shown as spr1167/fhs in the Figures) was markedly attenuated in virulence (FIGS. 11A and B), even more so than the fhs/piaA and piaA/proABC strains.

The Sp_1288/fhs 6B was also tested using an established mouse model of colonisation. This strain showed similar levels of colonisation after 7 days as the wild type 6B strain, indicating that despite the strong attenuation in virulence shown in FIG. 11 it will be a good candidate strain for testing for its protective efficacy (see FIG. 12).

The protective ability of the Sp_1288/fhs 6B strains against invasive disease or colonization was tested using mouse models. Prior colonisation with the mutant strain was as effective as prior colonisation with the wild type 6B strain at preventing subsequent pneumonia when the mice were re-challenged with wild type 6B *S. pneumoniae* 4 (pneumonia) or 6 (nasopharyngeal colonisation) weeks after nasopharyngeal inoculation (see FIG. 13).

Given that colonization experiment was successful for A1167/fhs 6B strain, we then measured anti-*S. pneumoniae* IgG levels in sera using ELISA (FIG. 14). We also determined specific anti protein responses by using our pneumococcal array, which measures antigen responses to 254 *S. pneumoniae* protein antigens. The results showed strong antibody responses to multiple protein antigens (data not shown).

ΔFhs/piaA Double Mutant Strain in 15B Serotype

A Δfhs/piaA double mutant strain was also generated in serotype 15B successfully using the methods and primers as described for the 6B strain. Sequencing around the mutation site and amplification by PCR confirmed the deletion of the relevant genes. This demonstrates that the methods described herein are applicable to various different serotypes. The fhs and piaA genes in the 15B serotype have a very high level of nucleotide and amino acid sequence identity to the genes in the 6B serotype strain.

The Δfhs/piaA 15B double mutant had the same phenotype as the wild-type 15B strain in mouse models (see FIGS. 11C and D). This was expected because the wild-type 15B strain is also avirulent in the mouse model and unable to cause septicaemia. Nevertheless, since the wild-type 15B strain has previously been shown to be able to successfully colonise in humans, it is expected that the 15B strain can also be used to establish protective immunity in humans.

Human Trial Data

The Δfhs/piaA strain was tested in human trials using the Experimental Human Pneumococcal Challenge model at the Liverpool School of Hygiene and Tropical Medicine (Professor Ferreira). Healthy human volunteers (median age 22 years, 64% female) had two doses of 7.4 to $8.4 \times 10^5$ CFU of wild-type, Δfhs/piaA, *S. pneumoniae* BHN418 6B administered intranasally on two separate occasions two weeks apart. Negative control subjects had physiological buffered saline (PBS) administered. At 6 months following the second dose all subjects were challenged by intranasal inoculation with $5 \times 10^5$ CFU of wild-type BHN418 6B *S. pneumoniae*. Successful colonisation was assessed post-intranasal administration of *S. pneumoniae* by plating of nasal washes obtained 2 and 6 days after intranasal administration of bacteria. FIG. 15 displays the trial design. Table 3 shows the colonisation rate in total in subjects administered wild-type or mutant *S. pneumoniae* twice in stage I of the trial, and then the percentage of subjects successfully colonised in each group when challenged at 6 months with wild type BHN418 *S. pneumoniae* 6B strain.

TABLE 3

Colonisation rates in the human pneumococcal challenge model for the Δfhs/piaA strain compared to humans previously administered intranasally wild-type *S. pneumoniae* (BHN418 6B) or PBS. Previous administration of the wild-type or Δfhs/piaA *S. pneumoniae* strains reduced subsequent colonisation rate with wild-type *S. pneumoniae* by 42% and 37% respectively (p < 0.05).

| *S. pneumoniae* strain | N number | % subjects colonised in Stage 1 (x2 dose mutant or wild type *S. pneumoniae*) | % subjects colonised at rechallenge with wild-type BHN418 6B *S. pneumoniae* |
|---|---|---|---|
| BHN418 6B | 31 | 18 (58%) | 9 (29%) |
| Δfhs/piaA 6B | 30 | 18 (60%) | 9 (30%) |
| PBS control | 32 | 0 (0%) | 15 (47%) |

The Δfhs/piaA *S. pneumoniae* mutant strain colonised the human nasopharynx at a similar rate as wild-type BHN418 *S. pneumoniae* 6B strain. Previous administration of the wild-type or Δfhs/piaA *S. pneumoniae* strains reduced subsequent colonisation rate with wild-type *S. pneumoniae* by 42% and 37% respectively (P<0.05). This data demonstrates that the Δfhs/piaA *S. pneumoniae* strain is as effective as nasal administration of the wild type *S. pneumoniae* strain at preventing subsequent recolonisation.

CONCLUSION

Here we describe the development and detailed evaluation of example live double mutant attenuated strains of *S. pneumoniae*, Δfhs/piaA, Δfhs/Sp_1288 and ΔproABC/piaA as proof of concept.

Screening 14 different genes and operons identified that deletion of fhs (physiological function unclear) or the proABC operon (annotated as required for proline biosynthesis) resulted in strains with markedly attenuated virulence in a range of murine models. Deletion of fhs was found to demonstrate the best results. Combining one or more of these mutations with deletion of piaA, a virulence gene that encodes the lipoprotein component of the dominant *S. pneumoniae* iron uptake ABC transporter, or Sp_1288 created double mutant strains that were highly attenuated in virulence without affecting the ability to colonise the nasopharynx, while being remarkably safer for use in humans as compared to single mutants. Deletion of fhs or proABC genes had a striking effect on systemic virulence similar in strength to loss of the capsule, an important *S. pneumoniae* virulence determinant, particularly for the deletion of the fhs genes. As the capsule is important for virulence, we also partially evaluated double mutant strains combining loss of the capsule with deletion of proABC or the manganese ABC transporter lipoprotein gene psaA as a comparative control. Nasal administration of double mutant strains stimulated serum antibody responses to protein rather than capsular antigens, and protected against subsequent septicaemia caused by pneumonia rechallenge. However, the Δcps/psaA and Δcps/proABC strains colonised poorly, and induced weaker immunity at the mucosal level with no effects on lung CFU after pneumonia rechallenge or nasal wash CFU after colonisation rechallenge, making these strains less attractive as live-attenuated vaccines. More detailed analysis of the immune response to colonisation with the Δfhs/piaA and ΔproABC/piaA strains demonstrated serum IgG recognised heterologous *S. pneumoniae* strains and largely recognised protein rather than capsular antigens. Using a protein array we identified many of the protein antigens that induce antibody after *S. pneumoniae* colonisation of mice.

The recognised antigens were largely conserved between colonisation with either the wild type or double mutant 6B strains, and included well recognised immunodominant *S. pneumoniae* antigens (eg PsaA, PspA, SktP) as well as conserved proteins with few data on their utility as protective antigens (MitG, Bga, and PhtE). The whole cell ELISA data for the 6B strain, immunoblots against bacterial lysates, and the protein array/MSD data all suggested that colonisation with wild type *S. pneumoniae* induced stronger antibody responses to protein antigens than colonisation with the Δfhs/piaA or ΔproABC/piaA strains, nevertheless, this did not lead to detectable differences in protective immunity against *S. pneumoniae* rechallenge.

Prior colonisation with the double Δfhs/piaA, Δfhs/Sp_1288 or ΔproABC/piaA strains protected against rechallenge with wild type *S. pneumoniae* for both the pneumonia and recolonisation models, with the fhs double mutants showing the best results. The mechanism of protection in the pneumonia model was determined using CD4+ antibody depleted mice and genetically modified C57BL/6JuMT$^{-/-}$ mice, in which B cell development is blocked at the pro-B stage. CD4+ depleted mice previously colonised with mutant strains mice were still protected against bacteraemia whereas antibody deficient mice were not. Importantly, colonisation with our double mutant strains significantly reduced nasal wash CFU after recolonisation with both the homologous 6B and the heterologous TIGR4 strain. Our results demonstrate that colonisation-induced prevention of nasopharyngeal recolonisation required CD4+ cells. The level of reduction in nasal wash CFU of >1 $\log_{10}$/ml would likely also have a major effect on colonisation rates in humans. Since colonisation is required for disease development, this would also reduce the incidence of heterologous *S. pneumoniae* invasive infections such as pneumonia and septicaemia.

Importantly, prior colonisation with the attenuated double mutant strains was not associated with potentially detrimental enhanced pulmonary inflammatory responses after subsequent pneumonia challenge with failure to detect a significant BALF or serum IL-17 response in previously colonised mice after pneumonia challenge. Overall, the murine data may suggest preventing systemic infection by previous colonisation events largely depends on antibody, whereas preventing recolonisation requires CD4+ cells. Lung immunity is believed to require a variable contribution of antibody and CD4+ cells and it is believed that antibodies play an important role in humans against both systemic and lung infection; in addition, vaccine-induced antibody to capsular antigens prevents colonisation.

The live attenuated strains of the present invention were also tested in human trials. Notably, the prior nasopharyngeal administration of live attenuated Δfhs/piaA mutant was as effective as prior administration of the *S. pneumoniae* wild-type strain at preventing colonisation on rechallenge with the wild-type strain after 6 months.

To summarise, colonisation of the nasopharynx with mutant attenuated strains present a novel strategy to support current vaccination programmes that can overcome some of the limitations of vaccines based on capsular antigens.

Materials and Methods

Bacterial Methods and Construction of the Attenuated Strains

Most mutant strains were constructed in the 6B BHN418 capsular serotype 6B clinical *S. pneumoniae* isolate using overlap extension PCR, using the methods below with and using the primers shown in Annex Table 3. The strains were constructed by overlap extension PCR using a transformation fragment in which the gene of interest has been replaced for either spectinomycin (ΔproABC, Δfhs, AspxB, ΔSp_1288 and ΔSp_1027) or kanamycine cassette (ΔpiaA, Δfhs). Two products corresponding to 600-1000 bp for both 5' and 3' were amplified from *S. pneumoniae* genomic DNA by PCR carrying 3' and 5' linkers complementary to the 5' and 3' portion of the antibiotic resistance gene respectively. The fragments were then fused with the antibiotic resistance marker by overlap extension PCR. Spec and Kan were amplified from Plasmids pR412 and pBAG5 mini respectively. The constructs were transformed into *S. pneumoniae* by homologous recombination and allelic replacement using a mix of competence stimulating peptides (CSP-1 and CSP-2) (kind gift from D. Morrison) and selection with antibiotics according to established protocols. Deletion of the gene of interest was confirmed by PCR and sequencing of the PCR products. A ΔpiaA/Δfhs double mutant strain was also constructed in the 15B serotype also using overlap extension PCR and using the methods described below with and using the primers shown in Annex Table 3.

Mutant stability was tested as previously described by three rounds of culture in THY for 8 hours at 37 degrees C. in $CO_2$ incubator without antibiotics, plating onto blood agar and transferring colonies after overnight culture to plates with and without antibiotic. Selected mutant strains underwent whole genome sequencing to identify unexpected mutations that affect the biology of the bacteria. DNA was isolated with Wizard genomic purification kit and samples were sequenced by MicrobesNG at Birmingham University.

Immunological Assays

Immunoblots of *S. pneumoniae* lysates, whole cell ELISAs, and measurement of IgG binding to the bacterial surface using flow cytometry were all performed as described below.

To detect serum proteins by Western blotting 10 μl of cell lysates (6B, TIGR4 or D39) were analyzed by 10% sodium dodecyl sulfate-polyacrylamide gel electrophoresis (SDS-PAGE), the proteins were transferred to a membrane, and fragments were revealed by immunoblotting using a goat anti mouse IgG (Abcam) antibody.

To determine pneumococcal antibody responses we performed whole cell ELISA. 6B strain was grown in THY broth to an $OD_{600}$ of approximately 0.5-0.8, washed and resuspended to an $OD_{600}$ of 0.5 in PBS. High adherence BRANDplates® 96-well microplates were incubated with 50 μl/well overnight before fixation in 4% formaldehyde for 10 min. Plates were washed and incubated with different dilutions of serum from colonized mice for 1 hour at room temperature. Antibody responses were measured by using HRP-conjugated goat anti mouse IgG (Abcam) for detection of IgG. Plates were incubated with 50 μl TMB chromogen solution (Thermo Fisher Scientific) until the solution turned the correct shade of blue and subsequently wells were inoculated with 50 μl of 1M sulphuric acid and measure the absorbance at 450 nm using a VersaMax microplate reader.

*S. pneumoniae* capsular and protein antigen antibodies were measured using established multiplexed electrochemiluminescence MSD assays. A protein array was constructed containing 289 *S. pneumoniae* proteins using a cell free *E. coli*-based in vitro transcription/translation (IVTT) expression system as described. The expressed proteins were selected since they have known antigenicity in humans and high degree of conservation amongst *S. pneumoniae* strains. Proteins were printed onto nitrocellulose coated glass AVID slides (Grace Bio-Labs, Inc., Bend, OR) using an Omni Grid 100 microarray printer (Genomic Solutions), probed with 1:25 mouse serum diluted in protein array blocking buffer (GVS, Sanford, ME), and images acquired and analysed using an ArrayCAM® Imaging System from Grace Bio-Labs.

Mouse Experimental Models

Animal procedures were approved by the local ethical review process and conducted in accordance with the UK national guidelines for animal use and care under project license (PPL70/6510). Pneumonia, sepsis, and colonisation models were performed as using group sizes of 5+4-8 weeks old CD1 mice, or wild type or uMT$^{-/-}$ (kind gift Claudia Mauri, UCL) C57BL/6J mice. Experiments were performed using pure inocula of wild-type or mutant strains to calculate bacterial CFU in recovered target organs for each strain at specific time points; for the systemic model of infection $5\times10^6$ CFU bacteria in 100 µl were inoculated by intraperitoneal (IP) injection and blood and spleen homogenates obtained at 24 hours for plating (Brown 2001, 2002, Khnadavila) and for the pneumonia model, $1\times10^7$ CFU bacteria in 50 µl were given by intranasal (IN) inoculation under isofluorane general anaesthesia, and blood and lung homogenates obtained at 18 hours for plating. For the colonization model groups of mice were inoculated via intranasal route with 10 µl of a suspension containing $1\times10^7$ CFU of each strain under light anaesthesia with isoflurane. Bacterial counts were obtained from nasopharyngeal lavage fluid at 7 days by serial dilutions of the samples plated onto Columbia blood agar plates containing gentamycin (5-µg ml-1) to differentiate pneumococcus from other streptococci.

To obtain target organ CFU or samples for immunology mice were sacrificed after 24-28 h (pneumonia/sepsis models) or 7 days (colonisation model) using a lethal dose of pentobarbital. For protection studies mice were colonised on day 0 and in some experiments day 14 before serum collection or challenge with wild type *S. pneumoniae* on day 28+. CD4+ cells were depleted using two intraperitoneal injection of 250 µg anti-CD4 mAb (GK 1.5, BioxCell) 48 and 24 hrs prior to *S. pneumoniae* challenge.

Statistical Analyses

Quantitative results are expressed as means±S.D or median with interquartile range for animal experiments. A Kruskall-Wallis non parametric test was used for comparison of data from three or more groups involving a single independent variable, and two-way ANOVA when data were grouped according to two independent variables. Dunn's multiple comparisons test was used for post hoc analysis. Statistical analyses were performed using GraphPad Prism 8 (GraphPad Software, La Jolla, CA, USA). P-values <0.05 were considered statistically significant.

RNA Samples and Sequencing

RNA for RNAseq were extracted from double mutant strains cultured in THY to an $OD_{595\ 0.4}$-0.5 using Mirvana RNA kit (Applied biosystems) with an additional physical lysis step using 0.1 mm glass beads (MP Biomedicals), treated with Turbo DNAse (Applied biosystems), and deleted of ribosomal RNA using Ribo-Zero Magnetic Kit Bacteria (Illumina) before preparation of sequencing libraries using the KAPA RNA HyperPrep kit (Roche Diagnostics) and 8 cycles of amplification. Libraries were multiplexed to 24 samples per run and single-end sequenced with the NextSeq 500 desktop sequencer (Illumina) using a 75 cycle highoutput kit. The RNA sequencing data was mapped and quantified to the *S. pneumoniae* transcriptome 6B 6B BHN418 reference using the Salmon algorithm. Downstream analyses were performed within the R statistical computing framework. The data was integrated into a matrix of raw counts using the TXimport package. The data was then normalised using the DEseq2 package using the rlog method prior to exploring the data using principal component analysis as a dimensionality reduction technique. This package was also used for differential gene expression. This analysis used a p-value cut-off of 0.01 and a cut-off of 1.5 log-fold change to be considered significantly differentially expressed.

Assessing Inflammatory Responses to Infection

Flow cytometry assays of inflammatory cell populations of single cell preparations of lung or spleen tissue were performed as using anti-mouse antibodies against the following surface markers: CD19 AP, CD11c PE-Cy7, Ly-6G peridinin chlorophyll protein-Cy5.5, CD11c Brilliant Violet 510, CD3 PE, CD4 Brilliant violet421, CD8 FITC (all BioLegend). White cell populations were initially identified using forward and side scatter dimensions, and immune subpopulations defined as: macrophages, CD11c+Ly-6G−; neutrophils, Ly-6G+CD11c−; B cells, CD19+CD3−; T cells, CD3+CD19−. BALF and serum cytokine levels (INF-γ, IL-1B, IL-4, IL-6, TNF-α, KC/GRO, IL-17A) were determined using MSD arrays (MSD, Rockville, USA) according to the manufacturer's protocols.

---

Annex
Nucleotide sequences of genes referred to herein

SEQ ID 1 - fhs gene
```
atgaaaacagatattgaaatcgcacagagtattgagttgaagccaattgttgatgttgtagagaaact
tggtatttcttacgacgatttggagttgtacggaaagtacaaggctaaactcagctttgataaaattc
gggcagttgagagcaatccagtcggtaaattgatcttggttactgccatcaacccaacacctgcaggt
gaaggaaagtcgacgcttaccattggtcttgcggatgccttgaacaagattggcaagaaaaccatgat
tgctatccgcgaaccgtctcttggtccagtcatggggatcaagggtggtgctgctggtggtgggtatg
cacaagttctgccaatggaagacatcaacctccactttactggagatatgcatgctattacaactgcc
aacaatgccctttctgccttgattgacaaccacttgcaccaagggaatgagctgggaattgatcaacg
tcgtatcctctggaaacgcgttgtggacttgaacgaccgtgcgctccgccatgtgactgttggtcttg
gtggtcctctaaacggtattccacgtgaggacggttttgatattacagttgcttcagaaatcatggca
attctttgcttggcaacggacatcgaggacttgaaacttcgtttggcgaatatcgttattggttatcg
ctatgaccgtacgcctgtttctgtaggtgatttgcaggttgagggtgccttggctttgattttgaagg
atgctattaagccaaacttggttcagacaatttacggtacacctgcctttgtacacggtggtccattt
gccaatatcgctcatggctgtaactctgtttggcgacgacaacagcccttcacttggctgattacac
tgttactgaagctggttttggtgcggaccttggtgctgagaaattccttgatatcaagacaccaaact
tgccaacatctccagatgcagttgttattgtcgcaacccttcgtgcccttaagatgaatggtggtgtg
gctaaagacgctctgactgaagaaaatgtagaggcagttcgtcgcaggttttgctaacttgaaacgcca
cgttgaaaatatccgtaagttcggtattccagcagttgtagctattaacgaatttgtatctgatacag
aagctgaaattgcagccttaaaagaactctgtgcctcaatcgatgtaccagttgaattggctagtgtc
tgggctgatggagcagaaggtggagtagcacttgccgaaacagttgttaagacaattgctgaaaatcc
agctaactataaacgtttgtatgataatgacctttctgtccaagaaaagattgaaaaaattgtcactg
```

-continued

Annex
Nucleotide sequences of genes referred to herein

```
aaatctatcgtggtagcaaagtgaactttgagaagaaagctcaaacacaaattgctcaaatcgttcaa
aacggttgggacaaattgccaatctgtatggctaaaactcaatacagtttctcagacaatccaaatgc
gcttggagcaccagaaaactttgaaattaccattcgtgaattggtaccaaaattaggtgcaggcttca
tcgttgccttaactggtgatgttatgaccatgccaggtcttccaaaacgtccagcagctctcaacatg
gatgttgaaagcgatggaactgtactaggcttgttctag
```

SEQ ID 2 - piaA gene
```
atgaaaaacaaatttttctaatagctattttagctatgtgtatagttttttagcgcttgttcttctaa
ttctgttaaaaatgaagaaaatacttctaaagagcatgcgcctgataaaatagttttagatcatgctt
tcggtcaaactatattagataaaaaacctgaaagagttgcaactattgcttgggaaatcatgatgta
gcattagcttaggaatagttcctgttggatttcaaaagcaaattacggtgtaagtgctgataaagg
agttttaccatggacagaagaaaaaatcaaagaactaaatggtaaagctaacctatttgacgatttgg
atggacttaactttgaagcaatatcaaattctaaaccagatgttatcttagcaggttattctggtata
actaaagaagattatgacactctatcaaaaattgctcctgtagcagcatacaaatctaaaccttggca
aacttatggagagatatgattaaaattgattcaaaagccttaggtatggaaaagaaggtgatgagt
taatcaaaaatactgaagctcgtatatccaaagaattagaaaaacatccagaaatcaaaggaaaaatc
aaaggaaaaaaagtattatttactatgattaatgctgcagatacatcaaaattctggatttatactag
caaagatccaagagcaaattatttaacagatttaggtctagtttccctgaatcattaaaagaatttg
agagtgaagatagttttgcaaaggaaatttctgcagaagaagcaaataagataaatgatgctgatgta
atcataacttatggtgatgataaaactcttgaagctttacaaaaagatcctctttttaggtaaaataaa
tgcaattaaaaatggtgccgttgctgtaattccagataatacaccgttagcagcctcatgcactccaa
caccactttcaataaactatactattgaagaatacctaaatctttaggaaatgcatgcaaaaatgcg
aaataa
```

SEQ ID 3 - proABC operon
```
atgaaatacaaacggattgtctcttaaggtgggtacttcttctctgacaaatgaggatggaagtttatc
acgtagtaaggtaaaggatattacccagcagttggctatgctgcacgaggctggtcatgagttgattt
tggtgtcttcaggtgccattgcggctggttttggagccttaggatttaaaaagcgtccgactaagatt
gctgataaacaggcttcagcagcggtagggcaagggctttttgttggaagaatatacaaccaatcttct
cttgcgtcaaatcgtttctgcacaaatcttgctgacccaagatgattttgtggataagcgtcgttata
aaaatgcccatcaggctttgtcggtttactcaaccgtggggcaattcctatcatcaatgagaatgat
agtgtcgttattgatgaggtcaaggttggggacaatgacactctaagtgcccaagtagcggcgatggt
ccaagcagacctttggttctcttgacagatgtggacggtctctatactggaaatcctaattcagatc
caagagccaaacgcttggagagaatagagaccatcaatcgtgagattattgatatggctggtggagct
ggttcgtcaaacggaactggggtatgttaaccaaaatcaaggctgcaactatcgcgacggaatcagg
agttcctgtttatatctgctcatccttgaaatcagattccatgattgaggcggcagaggaccgagg
atggttcttactttgttgctcaagagaaggggcttcgtacccagaaacaatggcttgccttctatgct
cagagtcaaggttctatttgggttgataaaggggctgcggaagctctctctcaacatggaaagagtct
tctcttatctggtattgttgaagcagaaggagcctttctcttacggtgatatcgtgacagtatttgaca
aggaaagtggaaaatcacttggaaaaggacgcgtgcaatttggagcatctgctttggaggatatattg
cgttctcaaaaagccaaggggtgtcttgatttaccgtgacgactggatttccattactcctgaaatcca
actacttttttacagaatttttagatggtgagtagacaagaacaatttgaacaggtacaggctgttaaaa
aatcgattaacacagctagtgaagaagtgaaaaatcaagccttgctagccatggctgatcacttagtg
gctgctactgaggaaatttagcggctaatgccctcgatatggcagcggctaagggggaaaatctcaga
tgtgatgttggatcgtctttatttggatgcagatcgtatagaagcgatggcaagaggaattcgtgaag
tggttgccttaccagatccaatcggtgaagttttagaaacaagtcagcttgaaaatggtttggttatc
acaaaaaaacgtgtagctatgggtgtgtcatcggtattatctatgaaagccgtccaaatgtgacgtctga
tgcggctgctttgactcttaagagtggaaatgcggttgttcttcgtagtggtaaggatgcctatcaaa
caacccatgccattgtcacagccttgaagaagggcttggagacgactactattcacccaaatgtgatt
caactggtggaagatactagccatgaaagtagttatgctatgatgaaggccaagggctatctagacct
cctcattcctcgtgaggagctggcttgatcaatgcagtggttgagaatgcgattgtacctgttatcg
agacagggactgggattgtccatgtctatgtggataaggatgcgaagacgaagacaaggcgctgtctatc
atcaacaatgctaaaaccagtcgtccttctgtttgtaatgccatggaggttctgctggttcatgaaga
taaggcagcaagcatccttcctcgcttggatcaaatgctggttgcagagcgtaaggaagctggactgg
aaccaattcaattccgcttggatagcaaagcaagccagtttgtttcaggtcaagcagctgagacccaa
gactttgacaccgagtttttagactatgtccttgctgttaaggttgtgagcagtttagaagaagcggt
tgcgcacattgaatcccacagcacccatcattcggatgctattgtgacggaaaatgctgaagctgcag
catactttacagatcaagtggactctgcagcggtgtatgttaatgcctcaactcgtttcacagatgga
ggacaatttggtcttggttgtgaaatggggatttctactcagaaattgcacgcgcgtggtccaatggg
cttgaaggaattgactagctacaagtatgtggtcactggtgatggacagataaggggagtaaatgaaga
ttggatttatcggtttggggaatatgggtgctagtttagcccaagctctgtcttgcaggctagaccgtca
gatgagattctccttgccaatcgtagtcaagtcaaggtggatgctttcatcgctaacttcggtggtca
gacttctaacaatgaagaaatattcgaagaagcagatgtgattttttctaggtgttaagcctgctcagt
tttctgaactgctttctcaataccagaccatccttgaaaaaagagaaagtcttcttttgatttcgatg
gcagctggattgatcttagaaaaactagcaagtcttatcccaagccaacaccgaattattcgtatgat
gcctaatacccctgcttctatcgggcaaggagtgattagttatgcctttgtctctcctaattgcagggctg
aggacagtgagctcttttgtcagctttttatccaaggctggtctcttggttgaattaggagaaaagctta
atcaatgcagcgacaggtcttgcaggctgtggaccagcctttgtctatctctttattgaggccttggc
agatgcaggtgttcagacgggattaccacgagaaacagccttgaaaatggcagcccaaactgtggtag
gagctgggcaattggtcctagaaagccagcaacatcctggagttttgaaagatcaagtttgtagtcca
ggcggttcgactattgctggcgtagcaagcctagaagcgcatgcttttcgaggaacggtcatggaggc
agttcatcaagcctataaacgaacacaagaactaggtaaataa
```

SEQ ID 4 - proB gene
```
atgaaatacaaacggattgtctcttaaggtgggtacttcttctctgacaaatgaggatggaagtttatc
acgtagtaaggtaaaggatattacccagcagttggctatgctgcacgaggctggtcatgagttgattt
```

-continued

Annex
Nucleotide sequences of genes referred to herein

```
tggtgtcttcaggtgccattgcggctggttttggagccttaggatttaaaaagcgtccgactaagatt
gctgataaacaggcttcagcagcggtagggcaagggctttgttggaagaatatacaaccaatcttct
cttgcgtcaaatcgtttctgcacaaatcttgctgacccaagatgattttgtggataagcgtcgttata
aaaatgcccatcaggctttgtcggttttactcaaccgtggggcaattcctatcatcaatgagaatgat
agtgtcgttattgatgaggtcaaggttggggacaatgacactctaagtgcccaagtagcggcgatggt
ccaagcagacccttttggttctcttgacagatgtggacggtctctatactggaaatcctaattcagatc
caagagccaaacgcttggagagaatagagaccatcaatcgtgagattattgatatggctggtggagct
ggttcgtcaaacggaactgggggtatgttaaccaaaatcaaggctgcaactatcgcgacggaatcagg
agttcctgtttatatctgctcatccttgaaatcagattccatgattgaggcggcagaggagaccgagg
atggttcttactttgttgctcaagagaaggggcttcgtacccagaaacaatggcttgccttctatgct
cagagtcaaggttctattgggttgataaaggggctgcggaagctctctctcaacatggaaagagtct
tctcttatctggtattgttgaagcagaaggagcctttcttacggtgatatcgtgacagtatttgaca
aggaaagtggaaaatcacttggaaaaggacgcgtgcaatttggagcatctgctttggaggatatattg
cgttctcaaaaagccaagggtgtcttgatttaccgtgacgactggatttccattactcctgaaatcca
actacttttacagaattttag SEQ ID 5 - proA gene
atggtgagtagacaagaacaatttgaacaggtacaggctgttaaaaaatcgattaacacagctagtga
agaagtgaaaaatcaagccttgctagccatggctgatcacttagtggctgctactgaggaaattttag
cggctaatgccctcgatatggcagcggctaaggggaaaatctcagatgtgatgttggatcgtctttat
ttggatgcagatcgtatagaagcgatggcaagaggaattcgtgaagtggttgccttaccagatccaat
cggtgaagtttttagaaacaagtcagcttgaaaatggtttggttatcacaaaaaaacgtgtagctatgg
gtgtcatcggtattatctatgaaagccgtccaaatgtgacgtctgatgcggctgctttgactcttaag
agtggaaatgcggttgttcttcgtagtggtaaggatgcctatcaaacaacccatgccattgtcacagc
cttgaagaagggcttggagacgactactattcacccaaatgtgattcaactggtggaagatactagcc
atgaaagtagttatgctatgatgaaggccaagggctatctagacctcctcattcctcgtggaggagct
ggcttgatcaatgcagtggttgagaatgcgattgtacctgttatcgagacagggactgggattgtcca
tgtctatgtggataaggatgcagacgaagacaaggcgctgtctatcatcaacaatgctaaaaccagtc
gtccttctgtttgtaatgccatggaggttctgctggttcatgaagataaggcagcaagcatccttcct
cgcttggatcaaatgctggttgcagagcgtaaggaagctggactggaaccaattcaattccgcttgga
tagcaaagcaagccagtttgtttcaggtcaagcagctgagacccaagactttgacaccgagtttttag
actatgtccttgctgttaaggttgtgagcagtttagaagaagcggttgcgcacattgaatcccacagc
acccatcattcggatgctattgtgacggaaaatgctgaagctgcagcatactttacagatcaagtgga
ctctgcagcggtgtatgttaatgcctcaactcgtttcacagatggaggacaatttggtcttggttgtg
aaatggggatttctactcagaaattgcacgcgcgtggtccaatgggcttgaaggaattgactagctac
aagtatgtggtcactggtgatggacagataagggagtaa SEQ ID 6 - proC gene
atgaagattggatttatcggtttggggaatatgggtgctagtttagccaagtctgtcttgcaggctag
accgtcagatgagattctccttgccaatcgtagtcaagtcaaggtggatgctttcatcgctaacttcg
gtggtcagacttctaacaatgaagaaatattcgaagaagcagatgtgattttttctaggtgttaagcct
gctcagttttctgaactgctttctcaataccagaccatccttgaaaaaagagaaagtcttcttttgat
ttcgatggcagctggattgatcttagaaaaactagcaagtcttatcccaagccaacaccgaattattc
gtatgatgcctaatacccctgcttctatcgggcaaggagtgattagttatgccttgtctcctcaattgc
agggctgaggacagtgagctctctttgtcagctttatccaaggctggtctcttggttgaattaggaga
aagcttaatcaatgcagcgacaggtcttgcaggctgtggaccagcctttgtctatctctttattgagg
ccttggcagatgcaggtgttcagacgggattaccacgagaaacagccttgaaaatggcagcccaaact
gtggtaggagctgggcaattggtcctagaaagccagcaacatcctggagtttttgaaagatcaagtttg
tagtccaggcggttcgactattgctggcgtagcaagcctagaagcgcatgcttttcgaggaacggtca
tggaggcagttcatcaagcctataaacgaacacaagaactaggtaaataa SEQ ID 7 - SpxB gene
atgactcaagggaaaattactgcatctgcagcaatgcttaacgtattgaaaacatggggcgtagatac
aatctacggtatcccatcaggaacactcagctcattgatggacgctttggctgaagacaaagatatcc
gcttcttacaagttcgccacgaagagacaggtgctcttgcagcggttatgcaagctaaattcggcggc
tcaatcggggttgcagttggttcaggtggtccaggtgcgactcacttgattaacggtgtgtttacgatgc
agctatggataacactccattcctagcgatccttggatcacgtccagttaacgaattgaacatggatg
ctttccaagagcttaaccaaaacccaatgtacaacggtatcgctgtttacaacaaacgtgtagcttac
gctgagcaattgccaaaagtaattgacgaagcctgccgtgctgcaatttctaaaaaaggtccagctgt
tgttgaaattccagtaaacttcggtttccaagaaatcgatgaaaatccatactacggttcaggttcat
acgaacgctcattcatcgctcctgctttgaacgaagttgaaatcgacaaaagctgttgaaatcttgaac
aatgctgaacgcccagttatctatgctggatttggtggtgttaaagctggtgaagtgattactgaatt
gtcacgtaaaatcaaagcaccaatcatcacaactggtaaaaactttgaagctttcgaatggaactatg
aaggtttgacaggttctgcttaccgtgttggtggaaaccagccaacgaagtggtctttgaagcagac
acagttctttttcttggttcaaacttcccattgctgaagtttacgaagcattcaagaacactgaaaa
attcatccaagtcgatatcgacccttacaaacttggtaaacgtcatgcccttgacgcttcaatccttg
gtgatgctggtcaagcagctaaagctatccttgacaaagtaaacccagttgaatcaactccatggtgg
cgtgcaaacgttaagaacaaccaaaactggcgtgattacatgaacaaactcgaaggtaaaactgaggg
tgaattgcaattgtatcaagtttacaatgcaatcaacaaacatgctgatcaagacgctatctactcaa
tcgacgtaggtaacactactcaaacatctactcgtcaccttcacatgacacctaagaacatgtggcgt
acatctccactctttgcgacaatgggtattgcccttcctggtggtatcgctgctgctaagaaagacaatcc
agatcgccaagtatggaacatcatgggtgacggagcattcaacatgctcacccagacgttatcacaa
acgttcaatacgaccttccagttatcaaccttgtcttctcaaatgctgagtacggcttcatcaagaac
aaatacgaagatacaaacaaacacttgtttggtgtagacttcacaaacgctgactacgctaaaattgc
ggaagctcaaggagctgttggattcacagttgaccgtatcgaagacatcgatgcagttgttgcagaag
ctgttaaattgaacaaagaaggtaaaactgttgtcatcgatgctcgcatcactcaacaccgtccactt
```

-continued

| Annex |
|---|
| Nucleotide sequences of genes referred to herein | ccagtagaagtacttgaattggatccaaaacttcactcagaagaagctatcaaagccttcaaggaaaa
atacgaagcagaagaactcgtaccattccgtctcttcttggaagaagaaggattgcaatcacgcgcaa
ttaaataa SEQ ID 8 - Sp_1288 gene
atggaaatcgaaaaaaccaatcgtatgaatgcgctctttgaattttatgcggcgcttttgacagataa
gcaaatgaattatatcgagctctactacgctgatgattacagccttgctgaaattgccgaggagttcg
gtgtcagtcgtcaggctgtctatgacaatatcaagcgaacagaaaagattctggaagattatgagatg
aaattgcacatgtactcggactatattgtccgcagtcagattttttgatcagattttggagcgctatcc
caaggataactttctgcaggagcagatagaaatttttaacaagcattgataatagagaataa SEQ ID 9 - Sp_1027 gene
atgagaaagaaactctttctgactagtgctgcggtcttgtgggcagtaacagctatgaatagcgtcca
tgcagcaacagatgttcaaaaagttatcgatgaaacctatgtccaacctgaatatgtcctaggttcct
ccctatctgaagaccaaaaaaatcaaactcttaaaaaactgggctacaatgcctcaacagataccaaa
gaattcaagaccatgacacctgatgtttattctaaaatcatgaatgtggccaatgactctagcttaca
gttgtattcatcagccaagattcaaaagctaggtgacaaatcgccacttgaggtcaagattgaaacac
cagaaaatatcactaaggtgactcaggatatgtaccgaaacgcagcagtaacgctgggtatggaacat
gccaaaatcactgtagcagcccctattccagttacaggtgagagtgctttggctgggatctactattc
gctagaagctaatggagccaaggtgccgcaagccaataaagatttggctcaagaagagctaaaggctt
tgtcagatatcaatgctgaaaataaggacaaatcaggctatgatgctaataaattaaacgttgcccta
gctgatatcaagtcaggactcgccaaagctaaagaaagcaagggaaatctgacagaagaagatgtacg
caagattgttgaagataccttaaaaaattacaaacttgatcaggtcataacaggaaaccagatcaata
tcatcatcaattttgccttgaatctctcaaagagtgatatcctcagcaatgcagatttcactaaaacc
ttaaatgaccttaaacaaagcatcgtatcacaagctggcgacagttttaaaaatatcaaccttaactt
tgattcggataaggcgctagaggacggtggtaacttcttaagctccctctggcaagcccttgtcaact
tcttcaagagttttggttcttaa

ANNEX TABLE 1

SNPs identified by whole genome sequencing of the Δfhs/piaA and ΔproABC/piaA
double mutant strains. Both strains contained the expected targeted gene deletions
with no other unexpected insertions or deletions. In addition, for Δfhs/piaA10
SNPs were found that resulted in single amino acid changes and 1 to stop codon;
andfor ΔproABC/piaA, 1 SNP was found that resulted in a single amino acid
change and 1 to a stop codon. The table indicates the position of each non-synonymous
SNP in bold and the amino acid change in the predicted protein.

| 1 | 6B BHN418 gene number | TIGR4 gene number | Gene name | Gene function | SNP | Amino acid change |
|---|---|---|---|---|---|---|
| Δfhs/ piaA | Spn_2061 | SP_1584 | codY | transcriptional repressor | cct/act | P27T |
| | Spn_1952 | SP_1465[1] | — | Hypothetical protein | tgc/tga | C31* |
| | Spn_0651 | SP_0103 | pgIF | capsular polysaccharide biosynthesis | atg/acg | M480T |
| | Spn_1482 | SP_0935 | tmk | thymidylate kinase | gcg/gtg | G162V |
| | Spn_1536 | SP_1002 | znuA1 | Adhesion lipoportein | gtt/gct | V20A |
| | Spn_1763 | SP_1228[1] | mutY | adenine glycosylase | ggc/agc | G126S |
| | Spn_1765 | SP_1230[2] | coaBC | synthesis of coenzyme A | tct/cct | S56P |
| | Spn_1765 | SP_1230[2] | coaBC | synthesis of coenzyme A | att/gtt | I65V |
| | Spn_1765 | SP_1230[2] | coaBC | synthesis of coenzyme A | atc/gtc | I84V |
| | Spn_0065 | SP_1797 | ycjP | ABC transporter permease protein | act/aat | T142N |
| | Spn_0967 | | — | unknown | agc/atc | S1001 |
| ΔproABC/ piaA | Spn_02062 | SP_1586 | cshA | ATP-dependent RNA helicase | caa/taa | Q338* |
| | Spn_1477 | SP_0930 | cbpE | Choline binding Protein E | tct/ttt | S592F |

*= stop codon;
[1]= decreased expression in this mutant (see Annex Table 2);
[2]= increased expression in this mutant (see Annex Table 2).

ANNEX TABLE 2

Differential expression of target genes (log2 foldchange)
between the double mutant strains and the wild type 6B
strain when cultured to mid-log
growth phase in THY broth. (fhs,
Spn_01764; piaA, Spn_1563; proABC, Spn_01479-81).

| 6B BHN418 gene number and name | TIGR4 gene number (if known) | Δfhs/ piaA | ΔproABC/ piaA |
|---|---|---|---|
| Spn_01479_proB | SP_0931 | | −5.328 |
| Spn_01480_proA | SP_0932 | | −5.629 |
| Spn_01481_proC | SP_0933 | | −5.542 |

ANNEX TABLE 2-continued

Differential expression of target genes (log2 foldchange)
between the double mutant strains and the wild type 6B
strain when cultured to mid-log
growth phase in THY broth. (fhs,
Spn_01764; piaA, Spn_1563; proABC, Spn_01479-81).

| 6B BHN418 gene number and name | TIGR4 gene number (if known) | Δfhs/ piaA | ΔproABC/ piaA |
|---|---|---|---|
| Spn_01563_piaA | SP_1032 | −6.692 | −6.288 |
| Spn_01764_fhs | SP_1229 | −6.542 | |

---

Annex Table 3: Primers used for creating mutants and plasmids used in this study.

| Primers Mutant strain | SEQ ID | Primer name | Description |
|---|---|---|---|
| ΔpspA | 10 | pspA_UpF | ctaatcaaccactttgggca |
| | 11 | pspA_Upspec_F | cagaaaagaggtaaatttaggatccccgtttgattttt |
| | 12 | pspA_UpspecR | aaatcaaacggggggatcctaaatttacctcttttctgatag |
| | 13 | pspA_Downspec_F | ggatccattccgcgtcgccgattaaattaaagcatgtt |
| | 14 | pspA_Downspec_R | aacatgctttaatttaatcggcgacgcggaatggatccaatt |
| | 15 | pspA_DownR | catggacggtcaccttagagtc |
| ΔpiaA | 16 | PiaA_UpF | gttatggcacaaatgggaaaggataaac |
| | 17 | PiaA_UpKanF | atgtttaaggagtttttgtcgatactatgttatacgcc |
| | 18 | PiaA_UpKanR | ggcgtataacatagtatcgacaaaaactccttaaacat |
| | 19 | PiaA_DownKanF | tgaagtacatccgcaacaggaaatgcatgcaaaatg |
| | 20 | PiaA_DownKanR | cattttgcatgcatttcctgttgcggatgtacttca |
| | 21 | PiaA_DownR | ctataagacctacgaagccaatag |
| ΔadcA | 22 | AdcA_UpF | Gcatagtatcaagttttgcacacctg |
| | 23 | AdcA_UpspecF | tcttatgaactagtcgatttctcagatccccgtttgattttt |
| | 24 | AdcA_UpspecR | aaaaatcaaacggggggatctgagaaatcgactagttcataagagctagt |
| | 25 | AdcA_DownspecF | ggatccattccgcgtctcctatttgataaaacgtcttactaaac |
| | 26 | AdcA_Downspec R | agtaagacgttttatcaaataggagacgcggaatggatcc |
| | 27 | AdcA_DownR | gagcaagggtaaaagctcgagttc |
| ΔpsaA | 28 | PsaA_UpF | ggaggtgacctatgattgc |
| | 29 | PsaA_UpspecF | gccctaataaattggaggatctagatccccgtttgattttt |
| | 30 | PsaA_UpspecR | aaaatcaaacggggggatctagatcctccaatttattagggct |
| | 31 | PsaA_DownspecF | aaattggatccattccgcgtcgcctctgaaaaacgtcattctc |
| | 32 | PsaA_Downspec R | atgacgttttcagaggcgacgcggaatggatcca |
| | 33 | PsaA_DownR | atattatccacgtattcaacgtagcga |
| ΔproABC | 34 | Spr832_UpF | ccaaacgggtatcttgttacag |
| | 35 | Spr832_UpspecF | tgttattcatgttataatggagatccccgtttgattt |
| | 36 | Spr832_UpspecR | atccattaaaaatcaaacggggggatctccattataacatgaat |
| | 37 | Spr832_DownspecF | aaaaattggatccattccgcgtcagctttgactgcctctttt |
| | 38 | Spr832_Downspec R | aaagaggcagtcaaagctgacgcggaatggatccaat |
| | 39 | Spr832_DownR | ggaaactaccaatgctgtcttgttt |
| ΔSp_1288 | 40 | Spr1197_UpF | tggaaggtttcaatgtccgtaat |
| | 41 | Spr1197_UpspecF | aactttcaaatgccattttttcttgatccccgtttgattttta |
| | 42 | Spr1197_UpspecR | taaaaatcaaacggggggatcaagaaaaatggcatttgaaagtt |
| | 43 | Spr1197_Downspec F | aattggatccattccgcgtcttattataccaaaaattagcc |
| | 44 | Spr1197_Downspec R | ggtagattaggctaattttttggtataataagacgcggaatggatcc |
| | 45 | Spr1197_DownR | cggatgcgaaatacaattcagtt |
| ΔspxB | 46 | SpxB_UpF | gtagaagtgtttggattggca |
| | 47 | SpxB_UpspecF | aaaaaattgaaggagagttatgatccccgtttgattttt |
| | 48 | SpxB_UpspecR | aaaaatcaaacggggggatcataactctccttcaatttttt |
| | 49 | SpxB_DownspecF | ggatccattccgcgtctctcgccgaaaatcaaat |
| | 50 | SpxB_Downspec R | gattttcggcgagagacgcggaatggatcca |
| | 51 | SpxB_DownR | aaacaagacagcattggtagtttcc |
| Δfhs | 52 | Fhs_UpF | ggcaagtgggtaattcttga |
| | 53 | Fhs_UpspecF | ctttcaaatctaacatatctctgatccccgtttgattttt |
| | 54 | Fhs_UpspecR | aaaaatcaaacggggggatcagagatatgttagatttgaaag |
| | 55 | Fhs_DownspecF | ttggatccattccgcgtccgcttattttttgtgtacaatagt |
| | 56 | Fhs_DownspecR | actattgtacacaaaaataagcggacgcggaatggatccaa |
| | 57 | Fhs_DownR | caaggaggagttctgcaattt |
| Δcps | 58 | Cps_UpF | ggattgataaaggtattggtggt |
| | 59 | Cps_UpKanF | gctttctgtgtggaattactataaatattgtcgatactatgttatacgccaac |

-continued

| Annex Table 3: Primers used for creating mutants and plasmids used in this study. | | | |
|---|---|---|---|
| Primers Mutant strain | SEQ ID | Primer name | Description |
| | 60 | Cps_UpKanR | gttggcgtataacatagtatcgacaatatttatagtaattccacacaga |
| | 61 | Cps_DownKanF | cttttctgaagtacatccgcaacgaaaatgatgaaaagttcaaaac |
| | 62 | Cps_DownKanR | gttttgaactttcatcattttcgttgcggatgtacttcagaaaag |
| | 63 | Cps_DownR | cagtttgtccattcaactgag |
| ΔmalX | 64 | MalX_UpF | gaaacgtttcaccgctttttctaaaagagg |
| | 65 | MalX_UpspecF | tgctattctttgggaggaagatcccccgtttgatttttaa |
| | 66 | MalX_UpspecR | ccattaaaaatcaaacggggatcttcctcccaaagaatagcaagttttattg |
| | 67 | MalX_DownspecF | aattggatccattccgcgtcttgttcaaggggggtgga |
| | 68 | MalX_Downspec R | gatttgatttccacccccttgaacaagacgcggaatggatccaatt |
| | 69 | MalX_DownR | caccgacactatcgttaaacatg |
| ΔaliA | 70 | AliA_UpF | gttcaaaactaggaagggcaattga |
| | 71 | AliA_UpspecF | ggagagaaagtttttaaaggagaagatcccccgtttgattttttaatgg |
| | 72 | AliA_UpspecR | ccattaaaaatcaaacggggggatcttctcctttaaaactttctctcc |
| | 73 | AliA_DownspecF | aattggatccattccgcgtcgcaaaataagaaaggat |
| | 74 | AliA_Downspec R | aatcctttcttatattttgcgacgcggaatggatccaatt |
| | 75 | AliA_DownR | ctatcatcaacttcaggacctgt |
| ΔglnPQ | 76 | GlnPQ_UpF | gaaccacctgatagccaatct |
| | 77 | GlnPQ_UpspecF | tgagagaatattcggaaaaggaggatcccccgtttgattttttaa |
| | 78 | GlnPQ_UpspecR | ccattaaaaatcaaacggggggatcctccttttccgaatattctctca |
| | 79 | GlnPQ_DownspecF | ttggatccattccgcgtcctgtaaggatttccttg |
| | 80 | GlnPQ_Downspec R | ctgcaaggaaatccttacaggacgcggaatggatccaatt |
| | 81 | GlnPQ_DownR | gcgaaagaagttgtagagtgtg |
| Δspr1759 | 82 | Spr1759_UpF | ggaaaagacctgccgtcaaa |
| | 83 | Spr1759_UpspecF | caggaatttttcctacgattgagatcccccgtttgatttttaa |
| | 84 | Spr1759_UpspecR | taaaaatcaaacggggggatctcaatcgtaggaaaattcctgc |
| | 85 | Spr1759_Downspec F | aattggatccattccgcgtcctactaacctatcag |
| | 86 | Spr1759_Downspec R | ctgataggttagtaggacgcggaatggatccaatt |
| | 87 | Spr1759_DownR | gaattgctcattagggaagcag |
| ΔSp_1027 | 88 | Spr0931_UpF | ggtgcgagaaatgttgagtgaa |
| | 89 | Spr0931_UpspecF | catctggctagaccaggtgtttgatcccccgtttgatttt |
| | 90 | Spr0931_UpspecR | aaaaatcaaacggggggatcaaacacctggtctagccagatg |
| | 91 | Spr0931_Downspec F | ttggatccattccgcgtcgagaaaagaatgttaaagaaaaatg |
| | 92 | Spr0931_Downspec R | catttttctttaacattcttttctcgacgcggaatggatccaa |
| | 93 | Spr0931_DownR | aaaccaatggttccaataccag |

Plasmids pR412    Derived from ColE1, carrying a 1145 bp mini transposon that contains Himar1
         IRs flanking the add9 gene SpcR (as described in Mol Microbiol, 2000. 38(4):
         p. 867-78)

pABG5mini    Derived from pMGC66, an *E. coli*-streptococcal shuttle vector that harbors
             phoZF (as described in J Bacteriol, 2000. 182(6): p. 1529-40)

The invention claimed is:

1. A live attenuated strain of *Streptococcus pneumoniae*, the live attenuated strain comprising at least two genes or operons that have disrupted expression or encode for a protein with impaired function, wherein the at least two genes or operons are selected from fhs, piaA, proABC, spxB, Sp_1288, and Sp_1027.

2. The live attenuated strain of claim 1, wherein the live attenuated strain is able to colonise the nasopharynx to a level which is at least 50% of the level observed for the wild-type strain.

3. The live attenuated strain according to claim 1, wherein the at least two genes or operons include fhs in combination with at least one of piaA, proABC, spxB, Sp_1288 and Sp_1027.

4. The live attenuated strain according to claim 1, wherein the at least two genes or operons are piaA and fhs.

5. The live attenuated strain according to according to claim 1, wherein the at least two genes or operons are fhs and Sp_1288.

6. The live attenuated strain according to claim 1, wherein the live attenuated strain does not contain a disrupted piuA gene.

7. The live attenuated strain according to claim 1, wherein the at least two genes or operons have disrupted expression, and wherein the expression of the at least two genes or operons is reduced by at least about 50% as compared to a wild-type strain.

8. The live attenuated strain according to claim 7, wherein the reduction in expression is determined by RNA-seq or by reverse transcriptase PCR.

9. The live attenuated strain according to claim 1, wherein the disrupted expression of the at least two genes or operons is caused by deletion and/or mutation of the at least to genes or operons or a portion thereof.

10. The live attenuated strain according to claim 7, wherein the disrupted expression of the at least two genes or operons is caused by biochemical inhibition of expression or function of the at least two genes or operons.

11. The live attenuated strain according to claim 1, wherein the at least two genes or operons encode for a protein with impaired function, and wherein the impaired function of the protein encoded by the at least two genes or operons is caused by the deletion and/or mutation of the at least two genes or operons or a portion thereof.

12. A pharmaceutical composition comprising at least one live attenuated strain of *Streptococcus pneumoniae* according to claim 1.

13. A pharmaceutical composition comprising two or more different live attenuated strains of *Streptococcus pneumoniae* according to claim 1, wherein the two or more different live attenuated strains are of a different serotype.

14. A pharmaceutical composition according to claim 12, further comprising at least one of a pharmaceutically acceptable adjuvant, excipient, diluent or carrier.

15. A pharmaceutical composition according to claim 12, wherein the pharmaceutical composition is formulated as a spray, optionally a nasal spray.

16. A method of ameliorating infection and/or enhancing immunity in a subject, comprising:

administering to a subject in need thereof a therapeutically effective amount of a live attenuated strain of *Streptococcus pneumoniae* or a pharmaceutical composition of the live attenuated strain of *Streptococcus pneumoniae*;

wherein the live attenuated strain of *Streptococcus pneumoniae* comprises at least two genes or operons that have disrupted expression or encode for a protein with impaired function and wherein the at least two genes or operons are selected from fhs, piaA, proABC, spxB, Sp_1288, and Sp_1027.

17. The method of claim 16, wherein the live attenuated strain or pharmaceutical composition prevents nasopharyngeal colonization of *S. pneumoniae* in a subject.

18. The method of claim 16, wherein, the infection is:

i) a *Streptococcus pneumoniae* infection, ii) pneumonia connected with *S. pneumoniae* iii) septicemia connected with *S. pneumoniae,* iv) meningitis connected with *S. pneumoniae* v) an exacerbation of chronic obstructive pulmonary disease (COPD) connected with *S. pneumoniae* vi) acute bronchitis connected with *S. pneumoniae* vii) acute sinusitis connected with *S. pneumoniae* or viii) acute otitis media connected with *S. pneumoniae.*

19. The method of claim 18, wherein the *S. pneumoniae* infection is of homologous serotype to the serotype of the live attenuated strain.

20. The method of claim 18, wherein the *S. pneumoniae* infection is of heterologous serotype to the serotype of the live attenuated strain.

21. The method of claim 16, wherein the method comprises administering the live attenuated strain or the pharmaceutical composition to the upper airway of the subject.

22. The method of claim 16, wherein the method comprises administering the live attenuated strain or the pharmaceutical composition intranasally, nasopharyngeally, to the oropharynx, subcutaneously, intradermally, intramuscularly, or a combination thereof.

23. The method of claim 16, wherein the subject is a human.

24. The method of claim 16, wherein the method prevents nasopharyngeal colonisation, lung infection, and/or bacteraemia.

* * * * *